(12) United States Patent
Miyamoto et al.

(10) Patent No.: US 8,444,547 B2
(45) Date of Patent: May 21, 2013

(54) MEDICAL TREATMENT ENDOSCOPE

(75) Inventors: Manabu Miyamoto, Tokyo (JP); Takahiro Kogasaka, Tokyo (JP); Takumi Dejima, Tokyo (JP); Kiyotaka Matsuno, Tokyo (JP); Ken Yamatani, Tokyo (JP); Saori Takeuchi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 782 days.

(21) Appl. No.: 11/652,880

(22) Filed: Jan. 12, 2007

(65) Prior Publication Data

US 2007/0249897 A1    Oct. 25, 2007

Related U.S. Application Data

(63) Continuation-in-part of application No. 11/435,183, filed on May 16, 2006, which is a continuation-in-part of application No. 11/331,963, filed on Jan. 13, 2006, now Pat. No. 8,092,371.

(51) Int. Cl.
*A61B 1/00* (2006.01)

(52) U.S. Cl.
USPC .................. 600/104; 600/106; 600/142

(58) Field of Classification Search
USPC ............. 600/104, 106, 114, 139–142, 144, 600/146; 606/1; 604/523–528
See application file for complete search history.

(56) References Cited

U.S. PATENT DOCUMENTS

| | | | |
|---|---|---|---|
| 4,245,624 A * | 1/1981 | Komiya | 600/106 |
| 4,577,621 A | 3/1986 | Patel | |
| 4,873,965 A * | 10/1989 | Danieli | 600/141 |
| 5,173,716 A | 12/1992 | Tetsuka | |
| 5,299,559 A | 4/1994 | Bruce et al. | |
| 5,318,013 A | 6/1994 | Wilk | |
| 5,395,367 A | 3/1995 | Wilk | |
| 5,448,989 A * | 9/1995 | Heckele | 600/142 |
| 5,683,349 A | 11/1997 | Makower et al. | |

(Continued)

FOREIGN PATENT DOCUMENTS

| CN | 1602166 A | 3/2005 |
|---|---|---|
| CN | 1886087 A | 12/2006 |

(Continued)

OTHER PUBLICATIONS

U.S. Office Action dated Mar. 24, 2010, received in related U.S. Appl. No. 11/435,183.

(Continued)

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

The medical treatment endoscope according to the present invention includes a sheath having a flexibility; at least one arm member having a bending part that projects out from a front end of the sheath and performs bending actions; an open/close mechanism which directs the arm member from a direction along a central axis of the sheath to a direction deviated from the central axis of the sheath, and from a direction deviated from the central axis of the sheath to a direction along the central axis of the sheath; and a viewing device and an illuminating member that are disposed to the front end side of the sheath.

11 Claims, 67 Drawing Sheets

U.S. PATENT DOCUMENTS

| | | | |
|---|---|---|---|
| 5,855,569 A | 1/1999 | Komi | |
| 5,916,147 A * | 6/1999 | Boury | 600/146 |
| 5,976,075 A | 11/1999 | Beane et al. | |
| 6,013,024 A | 1/2000 | Mitsuda et al. | |
| 6,352,503 B1 | 3/2002 | Matsui et al. | |
| 6,780,151 B2 * | 8/2004 | Grabover et al. | 600/146 |
| 7,833,156 B2 | 11/2010 | Williams et al. | |
| 2002/0087048 A1 | 7/2002 | Brock et al. | |
| 2004/0044270 A1* | 3/2004 | Barry | 600/142 |
| 2004/0117032 A1 | 6/2004 | Roth | |
| 2004/0138525 A1 | 7/2004 | Saadat et al. | |
| 2004/0138529 A1* | 7/2004 | Wiltshire et al. | 600/144 |
| 2004/0193212 A1 | 9/2004 | Taniguchi et al. | |
| 2005/0065397 A1 | 3/2005 | Saadat et al. | |
| 2005/0075538 A1* | 4/2005 | Banik et al. | 600/141 |
| 2005/0090709 A1 | 4/2005 | Okada et al. | |
| 2005/0119522 A1 | 6/2005 | Okada | |
| 2005/0222495 A1 | 10/2005 | Okada et al. | |
| 2005/0228224 A1 | 10/2005 | Okada et al. | |
| 2005/0234294 A1 | 10/2005 | Saadat et al. | |
| 2005/0234296 A1 | 10/2005 | Saadat et al. | |
| 2005/0250989 A1 | 11/2005 | Suzuki | |
| 2005/0273085 A1 | 12/2005 | Hinman et al. | |
| 2006/0111615 A1* | 5/2006 | Danitz et al. | 600/141 |
| 2006/0189845 A1* | 8/2006 | Maahs et al. | 600/146 |
| 2007/0004967 A1 | 1/2007 | Ueno et al. | |
| 2007/0043338 A1 | 2/2007 | Moll et al. | |
| 2007/0156019 A1 | 7/2007 | Larkin et al. | |
| 2007/0167679 A1 | 7/2007 | Miyamoto et al. | |
| 2007/0167680 A1 | 7/2007 | Miyamoto et al. | |
| 2007/0232856 A1 | 10/2007 | Ueno et al. | |
| 2007/0270640 A1 | 11/2007 | Dimitriou et al. | |
| 2007/0299387 A1 | 12/2007 | Williams et al. | |
| 2008/0051631 A1 | 2/2008 | Dejima et al. | |
| 2008/0065109 A1 | 3/2008 | Larkin | |
| 2008/0221391 A1 | 9/2008 | Weitzner et al. | |

FOREIGN PATENT DOCUMENTS

| | | |
|---|---|---|
| EP | 1582138 A2 | 10/2005 |
| EP | 1 872 709 A | 1/2008 |
| EP | 1 967 123 A1 | 9/2008 |
| JP | 55-45436 | 3/1980 |
| JP | 56-104501 | 8/1981 |
| JP | 63-102401 | 7/1988 |
| JP | S63-242217 | 10/1988 |
| JP | 5-5105 U | 1/1993 |
| JP | 5-49594 | 3/1993 |
| JP | 8-131441 | 5/1996 |
| JP | 10-258022 | 9/1998 |
| JP | 11-318815 A | 11/1999 |
| JP | 2001-46393 A | 2/2001 |
| JP | 2002-253563 A | 9/2002 |
| JP | 2004-180781 | 7/2004 |
| JP | 2004-290569 | 10/2004 |
| JP | 2005-287963 | 10/2005 |
| JP | 2005-296412 | 10/2005 |
| JP | 2006-141624 | 6/2006 |
| JP | 2006-516910 | 7/2006 |
| JP | 2006-516910 A | 7/2006 |
| JP | 2007-151595 | 6/2007 |
| JP | 2007-175070 | 7/2007 |
| JP | 2007-275624 A | 10/2007 |
| WO | WO 2004/064600 A2 | 8/2004 |
| WO | WO 2007/057880 A2 | 5/2007 |
| WO | WO 2007/074571 A1 | 7/2007 |
| WO | WO 2007/080974 A1 | 7/2007 |
| WO | WO 2007/127119 A1 | 11/2007 |

OTHER PUBLICATIONS

U.S. Office Action mailed Mar. 16, 2011 in related U.S. Appl. No. 11/435,183.

U.S. Office Action mailed Feb. 1, 2011 in related U.S. Appl. No. 11/809,488.

U.S. Office Action dated Nov. 30, 2011 of related received in related U.S. Appl. No. 12/057,990.

U.S. Office Action mailed Mar. 28, 2012 in related U.S. Appl. No. 13/212,610.

U.S. Office Action mailed May 31, 2012 in related U.S. Appl. No. 12/024,704.

U.S. Office Action mailed Jun. 6, 2012 in related U.S. Appl. No. 12/127,449.

U.S. Office Action mailed Jun. 26, 2012 in related U.S. Appl. No. 12/058,029.

U.S. Office Action mailed Jul. 2, 2012 in related U.S. Appl. No. 12/057,990.

U.S. Office Action mailed Jul. 3, 2012 in related U.S. Appl. No. 12/035,535.

Chinese Office Action dated Jul. 3, 2012 in related Chinese Patent Application No. 200780008372.7.

Japanese Office Action dated Feb. 19, 2013 together with an English Translation issued in corresponding Japanese Application No. 2009-058066.

Japanese Office Action (Notice of Reasons for Rejection) dated Dec. 18, 2012 from corresponding Japanese Patent Application Publication No. JP 2009-013615, together with an English language translation.

Japanese Office Action (Notice of Reasons for Rejection) dated Dec. 18, 2012 from corresponding Japanese Patent Application Publication No. JP 2009-027835, together with an English language translation.

Japanese Office Action (Notice of Reasons for Rejection) dated Dec. 18, 2012 from corresponding Japanese Patent Application Publication No. JP 2009-033278, together with an English language translation.

U.S. Office Action dated Mar. 19, 2013 in related U.S. Appl. No. 12/058,029.

* cited by examiner

View Along Direction A

View Along Direction B

View Along Direction C

View Along Direction D

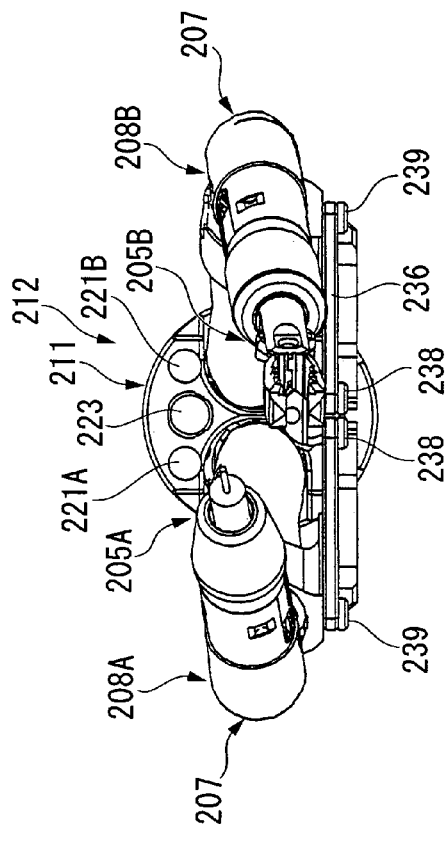
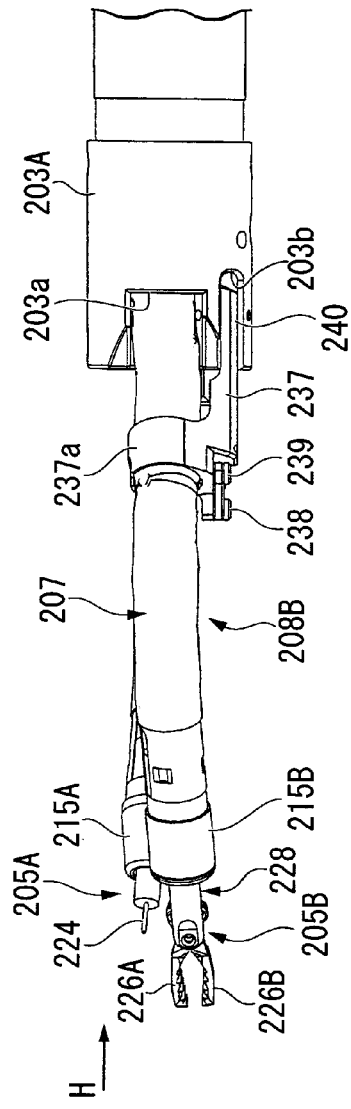
FIG. 24A
FIG. 24B

MEDICAL TREATMENT ENDOSCOPE

CROSS REFERENCE TO RELATED APPLICATIONS

This is a Continuation In-part Application (CIP) based on U.S. patent application Ser. No. 11/435183, titled "MEDICAL TREATMENT ENDOSCOPE", filed May 16, 2006, which is a CIP based on U.S. patent application Ser. No. 11/331963, titled "MEDICAL TREATMENT ENDOSCOPE", filed Jan. 13, 2006 now U.S. Pat. No. 8,092,371.

BACKGROUND OF THE INVENTION

1. Field of the Invention

The present invention relates to an endoscope apparatus.

2. Background Art

Laparoscopic surgery is a conventionally known technique that has been employed when performing a medical procedure such as observation or treatment of the internal organs of the human body. Rather than making a large abdominal incision, laparoscopic surgery provides for the procedure to be carried out by making several openings in the abdominal wall, and inserting a laparoscope and surgical instruments such as forceps into these respective openings. This type of surgery offers the benefit of being less invasive on the patient, since only small openings are made in the abdominal wall.

As a method of even further reducing stress on the patient, it has been proposed in recent years to carry out medical procedures by inserting a flexible endoscope into the patient via a natural opening such as the mouth, nostrils or anus. An example of a medical treatment endoscope used in such procedures is disclosed in U.S. Patent Application Publication No. 2005/0065397.

In the medical treatment endoscope disclosed in this reference, arm members that have a bendable end are respectively inserted into a plurality of lumens disposed within a flexible inserted part that is inserted into the body via the mouth of the patient. By inserting respective instruments through these arm members, the procedure site of interest can be approached from different directions with the various instruments. Accordingly, a plurality of procedures can be carried out in continuum by means of a single endoscope inserted into the body.

SUMMARY OF THE INVENTION

The medical treatment endoscope according to a first aspect of the present invention includes a sheath having flexibility; at least one arm member having a bending part that projects out from a front end of the sheath and performs bending actions; an open/close mechanism which directs the arm member from a direction along a central axis of the sheath to a direction that deviates from the central axis of the sheath, and from a direction that deviates from the central axis of the sheath to a direction along the central axis of the sheath; and a viewing device and an illuminating member that are disposed at the front end side of the sheath.

The medical treatment endoscope according to a second aspect of the present invention includes a sheath having flexibility, in which a first lumen with an open end is formed; at least one arm member having a second lumen with an open-end extending in the axial direction into which a procedure device for performing a procedure in an organ is insertable, and a bending part for performing bending actions, a front end of the arm member projecting out from the open end of the first lumen; an open/close mechanism which directs the arm member projecting out from the first lumen from a direction along the central axis of the sheath to a direction that deviates from the central axis of the sheath, and from a direction that deviates from the central axis of the sheath to a direction along the central axis of the sheath; and a viewing device and an illuminating member that are disposed at a front end side of the sheath.

The medical treatment endoscope according a third aspect of the present invention includes a first sheath having flexibility and an open end; a second sheath that is provided with a first arm member that has a front end and a base end and is inserted so that the front end area projects out from the first sheath, and that has a bending part that is freely bendable through manipulation by an operator; a third sheath provided with a second arm member that has a front end and a base end and is inserted so that the front end region projects out from the first sheath, and that has a bendable part that is freely bendable through manipulation by the operator; a viewing device that is independently disposed at the front end of the first sheath from the second sheath and the third sheath, and is for viewing a target image; and an illuminating member that is independently disposed at the front end of the first sheath from the viewing device, the second sheath and the third sheath, and is for radiating illuminating light on the target image.

The medical treatment endoscope according to a third aspect of the present invention includes a sheath having a flexibility; an arm means that projects out from the end of the sheath and is for performing bending actions; an open/close means which directs the arm means from a direction along a central axis of the sheath to a direction deviated from the central axis of the sheath, and from a direction deviated from the central axis of the sheath to the direction of the central axis of the sheath; a viewing means for viewing an area further toward the front end than the sheath; and an advance/retract means for advancing or retracting the arm means with respect to the sheath.

BRIEF DESCRIPTION OF DRAWINGS

FIG. 24A is a view of the front end of the medical treatment endoscope according to the third embodiment, along the H direction.

FIG. 24B is a side view of the medical treatment endoscope according to the third embodiment.

DETAILED DESCRIPTION OF THE INVENTION

Embodiments according to the present invention will now be described in detail below. Structural elements that are equivalent in the following will be assigned the same numeric symbols and redundant explanations thereof will be omitted.
[First Embodiment]

Figure 1:
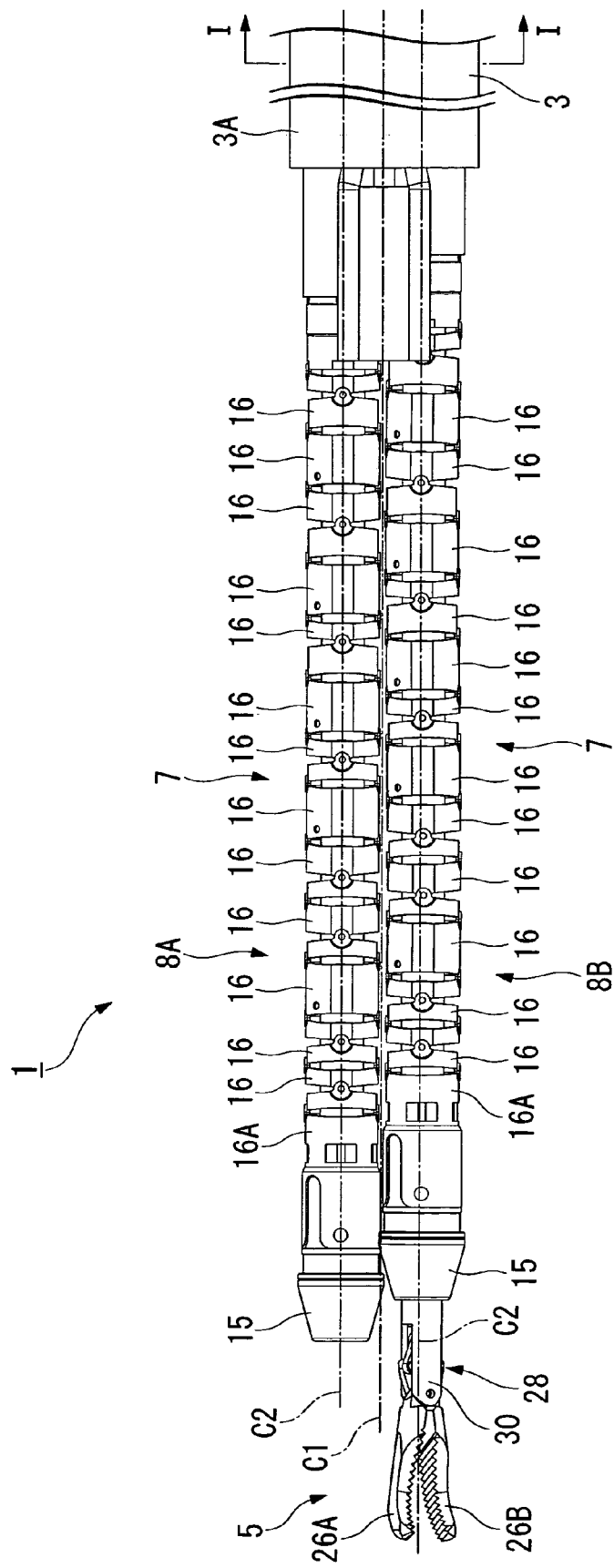
FIG. 1 shows the configuration of a tip end of the endoscope apparatus according to a first embodiment of the present invention.
Figure 2A:
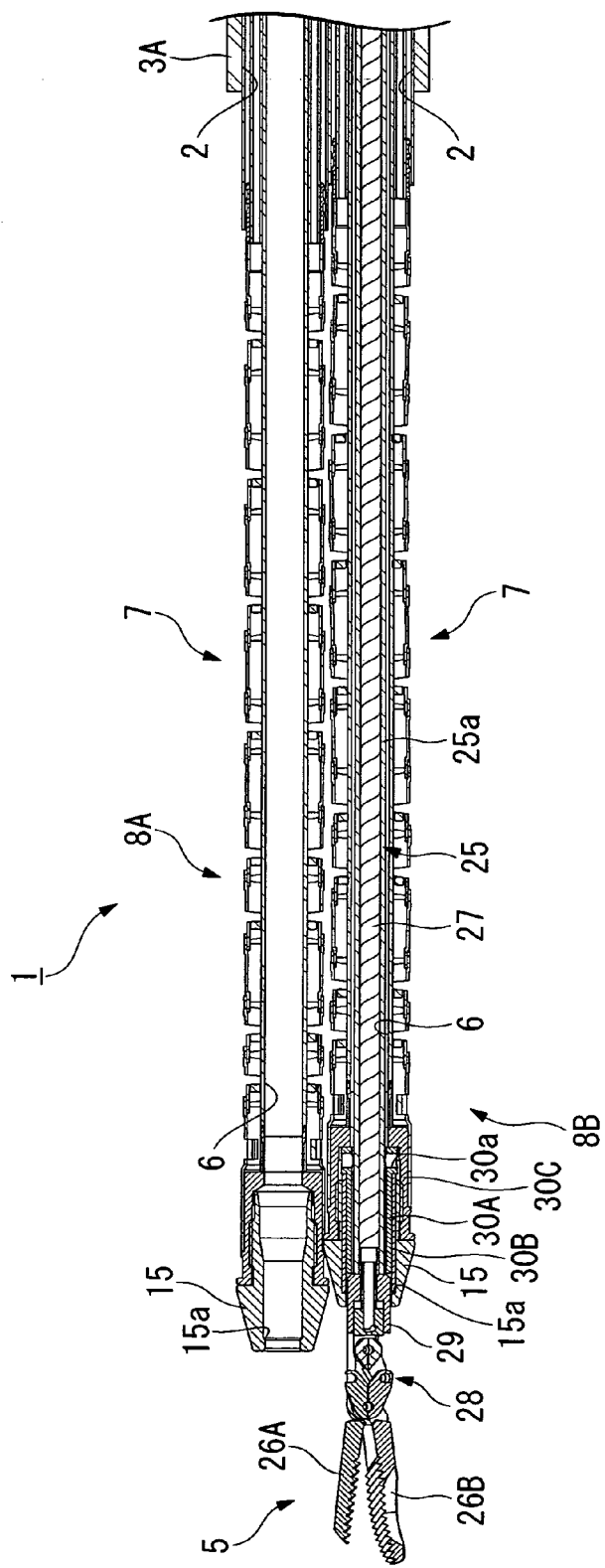
FIG. 2A shows the configuration of a tip end of the endoscope apparatus according to the first embodiment of the present invention.
Figure 2B:
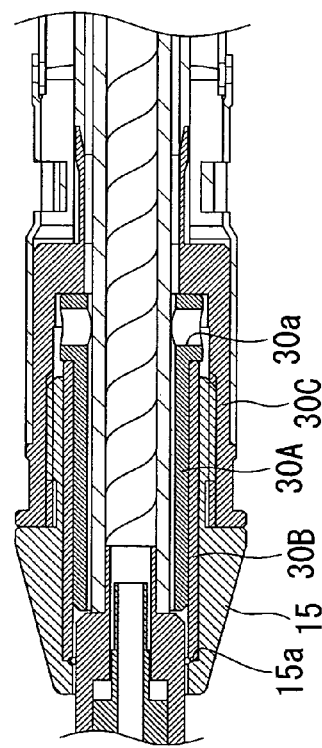
FIG. 2B is a partially enlarged diagram of FIG. 2A.
Figure 3:
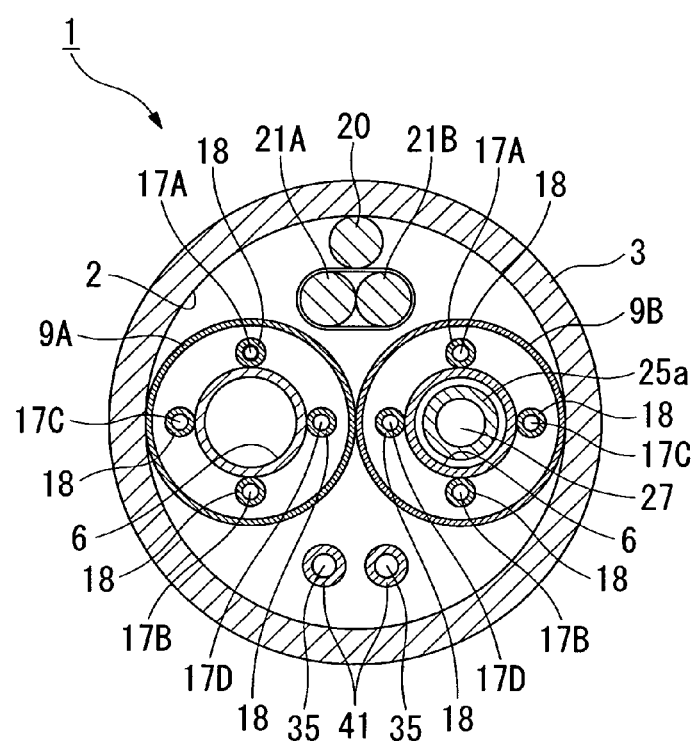
FIG. 3 is a cross-section viewed along line I-I of FIG. 1.
Figure 4:
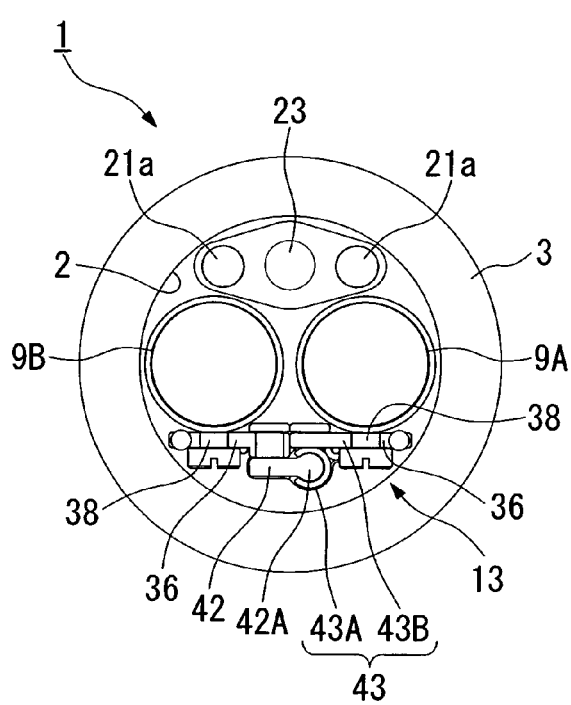
FIG. 4 is a view of the front end of the medical treatment endoscope according to the first embodiment.

As shown in FIGS. 1 through 3, the medical treatment endoscope 1 according to this embodiment is provided with a flexible first sheath (sheath) 3 in which an open-ended first lumen 2 is formed; a second sheath 9A having a first arm member 8A to which is disposed an open-ended instrument insertion channel (second lumen) 6 into which instruments such as gripping forceps 5 are inserted, and a bending part 7 that projects out from the first sheath 3 and carries out bending actions; and a third sheath 9B having a second arm member 8B to which the instrument insertion channel 6 and the bending part 7 are disposed. Moreover, as shown in FIGS. 4 through 8B, the medical treatment endoscope 1 according to this embodiment is further provided with an open/close mechanism 10 for changing the inclination of the first arm member 8A and the second arm member 8B that project out from the first sheath 3, from the central axis C1 of the first sheath 3 to a direction away from the central axis C1, and from this direction away from the central axis C1 toward the direction of the central axis C1 (separation release); a viewing device 12 that is disposed at the front end side of the first sheath 3; and an advance/retract mechanism 13 for advancing and retracting the first arm member 8A with respect to the first sheath 3.

The second sheath 9A has a front end and a base end, the front end region forming the first arm member 8A. The second sheath 9A is inserted into the first lumen 2 so as to project out from the first sheath 3, at a position in the first lumen 2 so as to appear on the right side of the viewing screen. The third sheath 9B has a front end and a base end, the front end region forming the second arm member 8B. The third sheath 9B is inserted into the first lumen 2 adjacent to the second sheath 9A, so as to project out from the first sheath 3.

As shown in FIGS. 1 and 2, rigid front end parts 15 are disposed at the front ends of the first arm member 8A and the second arm member 8B. A bumper 15a is provided at the front end part 15 for limiting movement in the forward direction when gripping forceps 5 or the like are inserted from the base end side of the instrument insertion channel 6.

As in the case of the typical flexible endoscope, the bending part 7 is designed such that a plurality of joint wheels 16 are mutually axially supported to enable rotation, and are connected along the direction of the central axis C2 of the first arm member 8A and the second arm member 8B. Furthermore, bending wires 17A, 17B, 17C, and 17D such as shown in FIG. 3, are connected to the joint wheel 16A disposed farthest from the front end. Bending wires 17A, 17B, 17C, and 17D are each inserted into and pass through the joint wheels 16 at positions so as to divide the circumferential periphery of the joint wheels 16 into quarters.

Figure 7A:
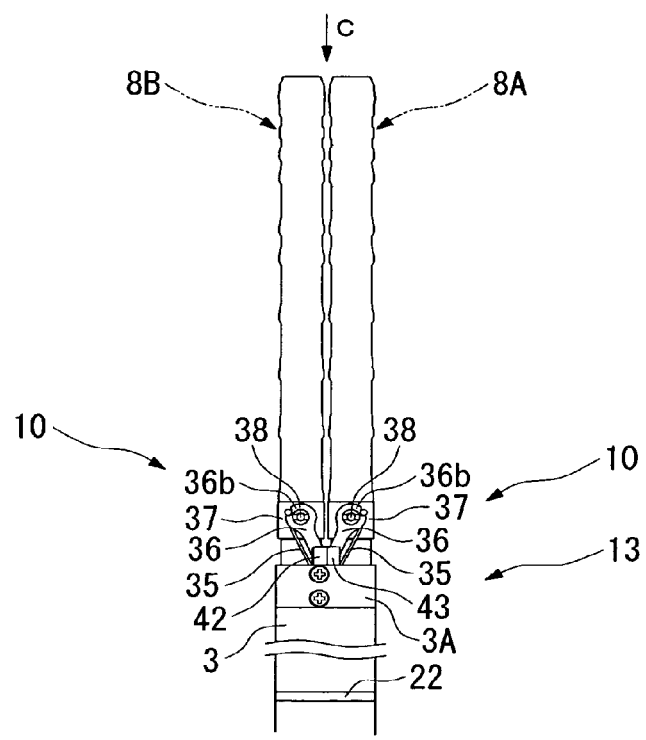
FIG. 7A is a plan view showing the starting state of the arm member of the medical treatment endoscope according to the first embodiment.
Figure 7B:
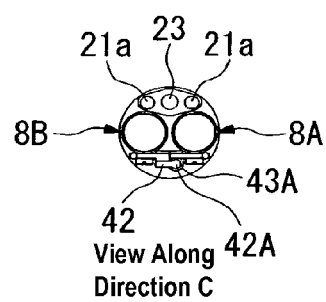
FIG. 7B is a view along direction C in FIG. 7A.

Bending wires 17A and 17B, and bending wires 17C and 17D are paired respectively, and positioned so as to be symmetrical about the center of bending part 7. Each bending wire 17A, 17B, 17C, and 17D is inserted into a bending wire coil 18 within the first sheath 3. A video cable 20, which is connected to a viewing device 12 which includes an image pick-up unit 11 and an objective lens (optical member for viewing) 23, and two light guides (illuminating members) 21A and 21B which emit illuminating light onto illuminating lenses (illuminating optical members) 21a, which are structural components of the illuminating members and are for lighting the object to be illuminated by forming the illuminating light bundles into a desired light bundle profile, are inserted into the first sheath 3 so as not to interfere with the second sheath 9A, the third sheath 9B and the various bending wires. A rigid sheath front end part 3A is disposed to the front end of the first sheath 3. An objective lens 23, and illuminating lenses 21a which are on either side of the objective lens so as to interpose the objective lens 23 therebetween, are disposed to the sheath front end part 3A. In other words, the illuminating members are disposed on either side of the viewing device. As shown in FIG. 7A, a plurality of markings 22, for understanding the length of the inserted portion when the endoscope is inserted into the patient, are provided at predetermined intervals along the surface of the first sheath 3 on the hand-held side thereof.

As shown in FIGS. 1, 2A, 2B, and 10, a gripping forceps 5 is provided with a forceps insertion part 25 that has a long narrow coil sheath 25a. A pair of forceps pieces 26A and 26B are disposed to the front end of the forceps insertion part 25. This pair of forceps pieces 26A and 26B is connected to a forceps manipulating wire 27, which is inserted into the coil sheath 25a to enable free advancing and retracting, via a forceps linking part 28 which converts the advancing/retracting operation of the forceps manipulating wire 27 into the opening/closing operation of the paired forceps pieces 26A and 26B. A forceps linking part 28 is disposed to a front end cover 29 which is attached to the coil sheath 25a.

As shown in FIGS. 2A and 2B, this gripping forceps 5 is fixed in place via a first connecting member 30A, a second connecting member 30B and a third connecting member 30C to the second arm member 8B to enable free rotation. The first connecting member 30A is tubular, with its inner peripheral surface fixed in place near the front end of the gripping forceps 5 by a screw, adhesive agent or the like. The second connecting member 30B is in the form of a short pipe, and is interposed between the bumper 15a of the front end part 15 and the first connecting member 30A. The third connecting member 30C is in the form of a short pipe, and is formed so that the base end projects inward in the radial direction. This third connecting member 30C engages with the front end part 15, and pushes the first connecting member 30A in the forward direction. As a result, the second connecting member 30B is pushed further forward than the first connecting member 30A, coming into contact with the bumper 15a of the front end part 15, thereby restricting movement of the gripping forceps 5 in the advancing or retracting direction. On the other hand, the gripping forceps 5 are attached in a freely rotating manner with respect to the instrument insertion channel 6. Note that the third connecting member 30C may also be attached to the front end part 15 by screwing, or by an adhesive agent or the like.

The gripping forceps 5 are provided with a forceps operating part (procedure operating part) 31. The forceps operating part 31 is provided with a forceps operating part main body 32 to which the coil sheath 25a is connected, and a forceps handle 33 to which a forceps manipulating wire 27 is connected and which is disposed in a freely retracting and advancing manner with respect to the forceps operating part main body 32.

The open/close mechanisms 10 are respectively provided corresponding to the number of the first arm members 8A and the second arm members 8B. Note that since the structure is almost entirely the same, the following explanation will be directed to the open/close mechanism 10 of the first arm member 8A.

As shown in FIGS. 4 through 8B, the open/close mechanism 10 is provided with a bending opening/closing wire (open/close operating member) 35, which is capable of advancing and retracting with respect to the first sheath 3; a linking part 36 to which the end of the bending opening/closing wire 35 is connected, which converts the advancing/retracting operation of the bending opening/closing wire 35 into the opening/closing operation of the first arm member 8A with respect to the first sheath 3; and a support 37 which is in the form of a short pipe that is axially supported to enable rotation about the linking part 36, or, alternatively, is connected to the linking part 36 in a manner so as to prevent rotation. This short pipe-shaped support 37 is fixed in place along the bending part 7 of the arm member 8A. Note that it is also acceptable to fix this short pipe-shaped support 37 further toward the base end than the bending part 7.

The linking part 36 is formed extending in the form of a long plate, and one end 36a is axially supported by a guide member 42 of the first sheath 3, explained below, to enable rotation. Note that in the case of the second arm member 8B, one end 36a of the linking part 36 is axially supported by a sliding member 43, explained below, that can advance and retract along the central axis C1.

The support 37 is supported by another end 36b of the linking part 36 via a support axis 38, to enable rotation thereof, or alternatively, is connected so that rotation is not possible. The other end 36b of the linking part 36 is formed in the shape of a disk centered about the position of attachment to the support axis 38, with bending opening/closing wires 35 supported by the periphery thereof. The bending opening/closing wires 35 are disposed inside the first sheath 3, inserted into respective bending opening/closing wire coils 41.

An advance/retract mechanism 13 is provided with a guide member 42 extending in the direction of the central axis C1 of the first sheath 3 and fixed in place to the first sheath 3, and a sliding member 43 that can be freely advanced and retracted with respect to the guide member 42. The guide member 42 is formed in the shape of a flat plate extending a predetermined length in one direction, and, with respect to the central axis C1 of the first sheath 3, is disposed at a position opposite where the light guides 21A and 21B and the video cable 20 are inserted (i.e., the area opposite where the light guides 21A and 21B and the video cable 20 are inserted, such that the second sheath 9A and the third sheath 9B are interposed therebetween). An engaging convexity 42A, approximately cylindrical in shape, is provided to one end in the width direction of the guide member 42 on the first arm member 8A side. The sliding member 43 is provided with a roughly C-shaped engaging concavity 43A that engages with the engaging convexity 42A to enable sliding, and a connector 43B that links the engaging concavity 43A and the first arm member 8A. The amount of movement of the sliding member 43 with respect to the guide member 42 is restricted to predetermined limits. Note that it is also acceptable to enable advancing and retracting of the second arm member 8B, rather than the first arm member 8A, using the same type of advance/retract mechanism.

Figure 9:
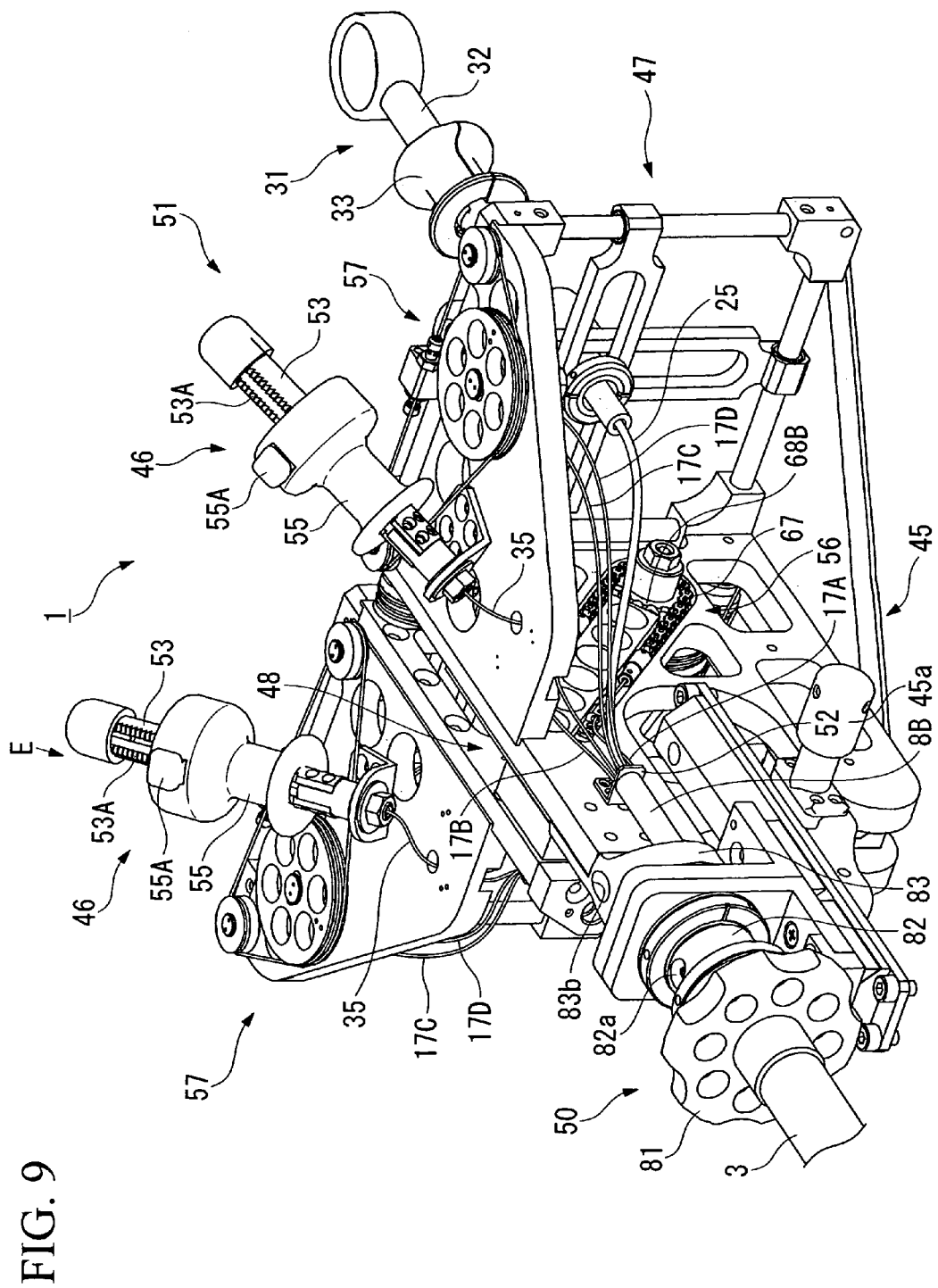
FIG. 9 is a perspective view showing the operating part of the medical treatment endoscope according to the first embodiment.
Figure 10:
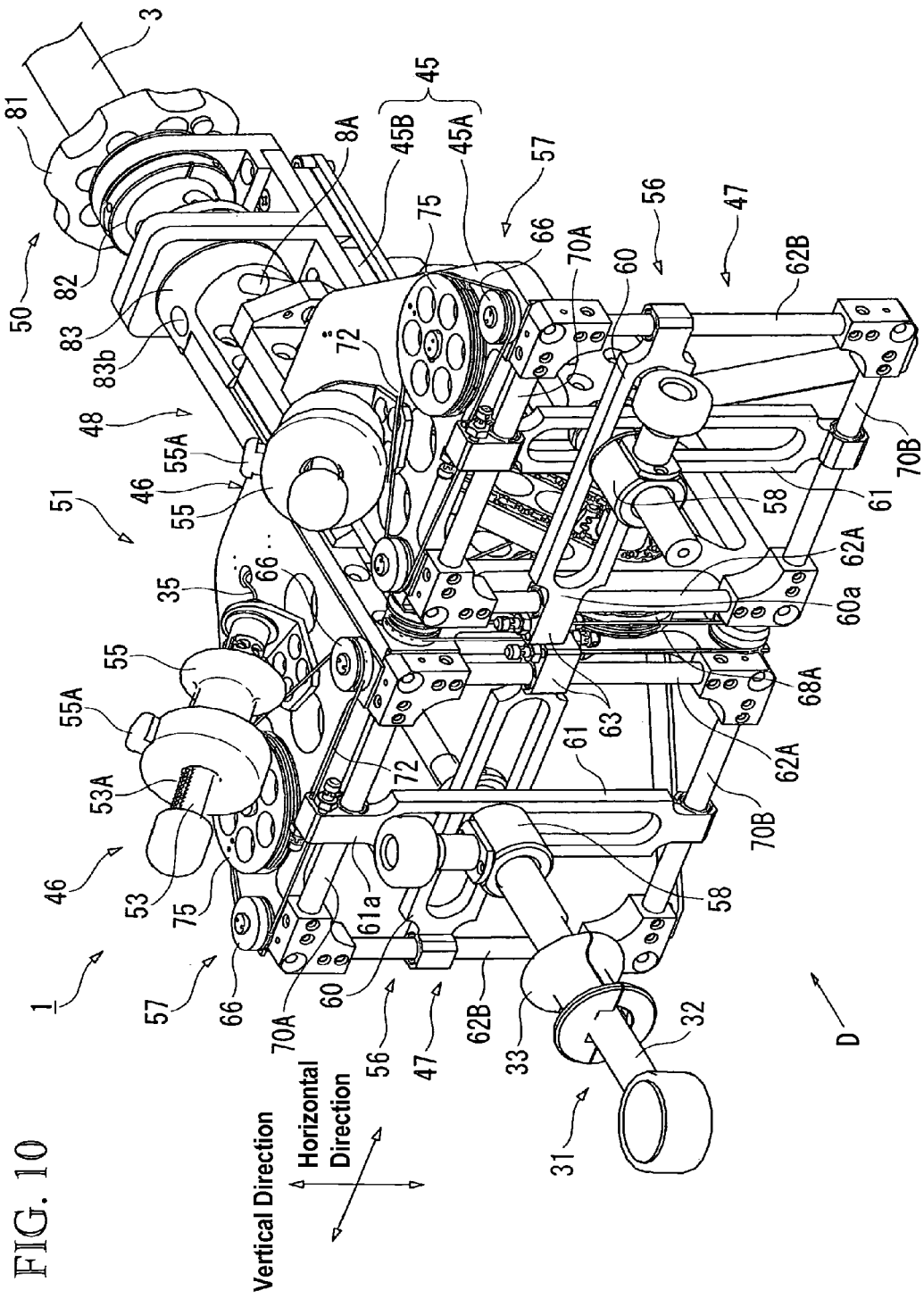
FIG. 10 is a view along direction E in FIG. 9.
Figure 11:
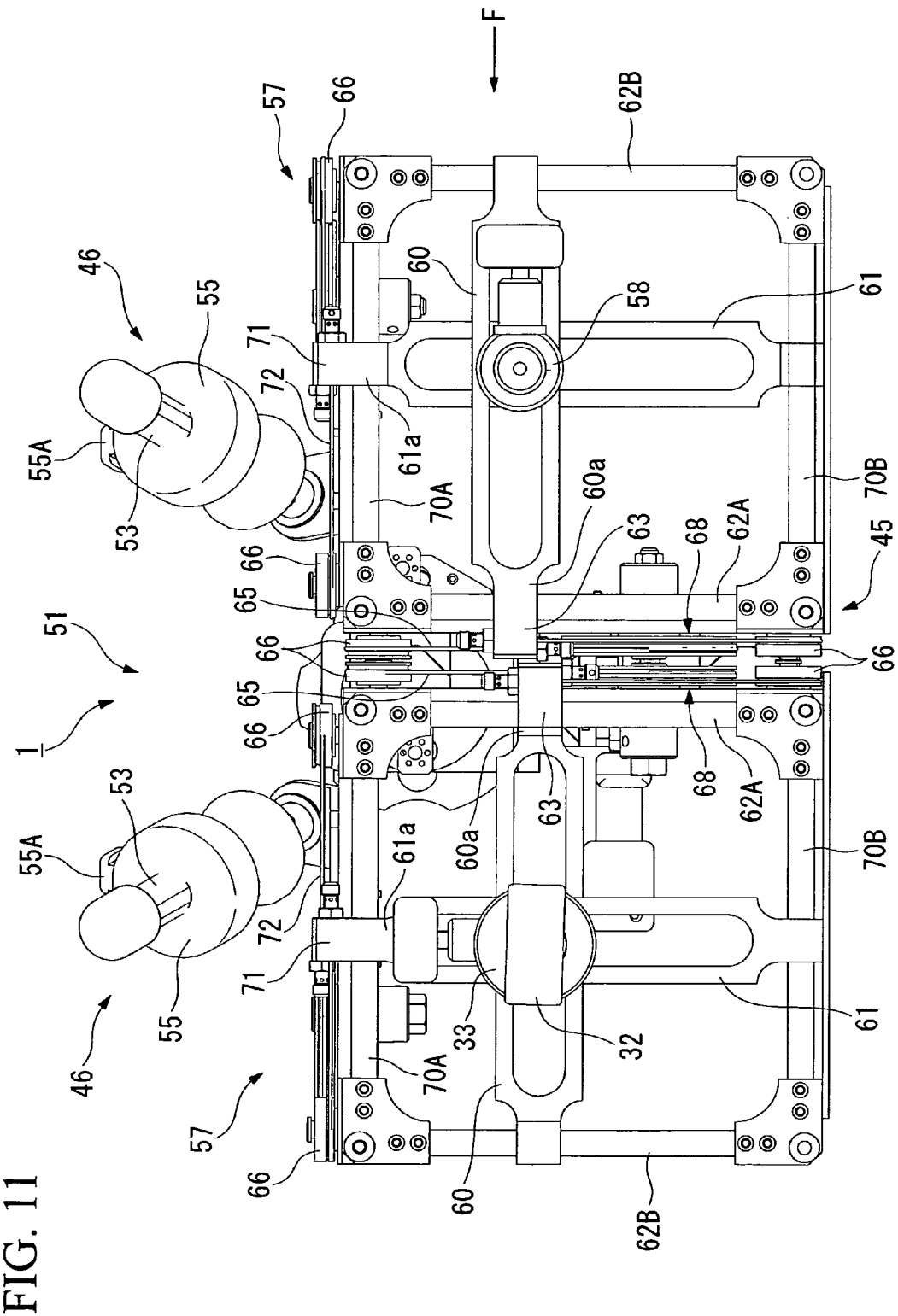
FIG. 11 is a view along direction E in FIG. 10.
Figure 12:
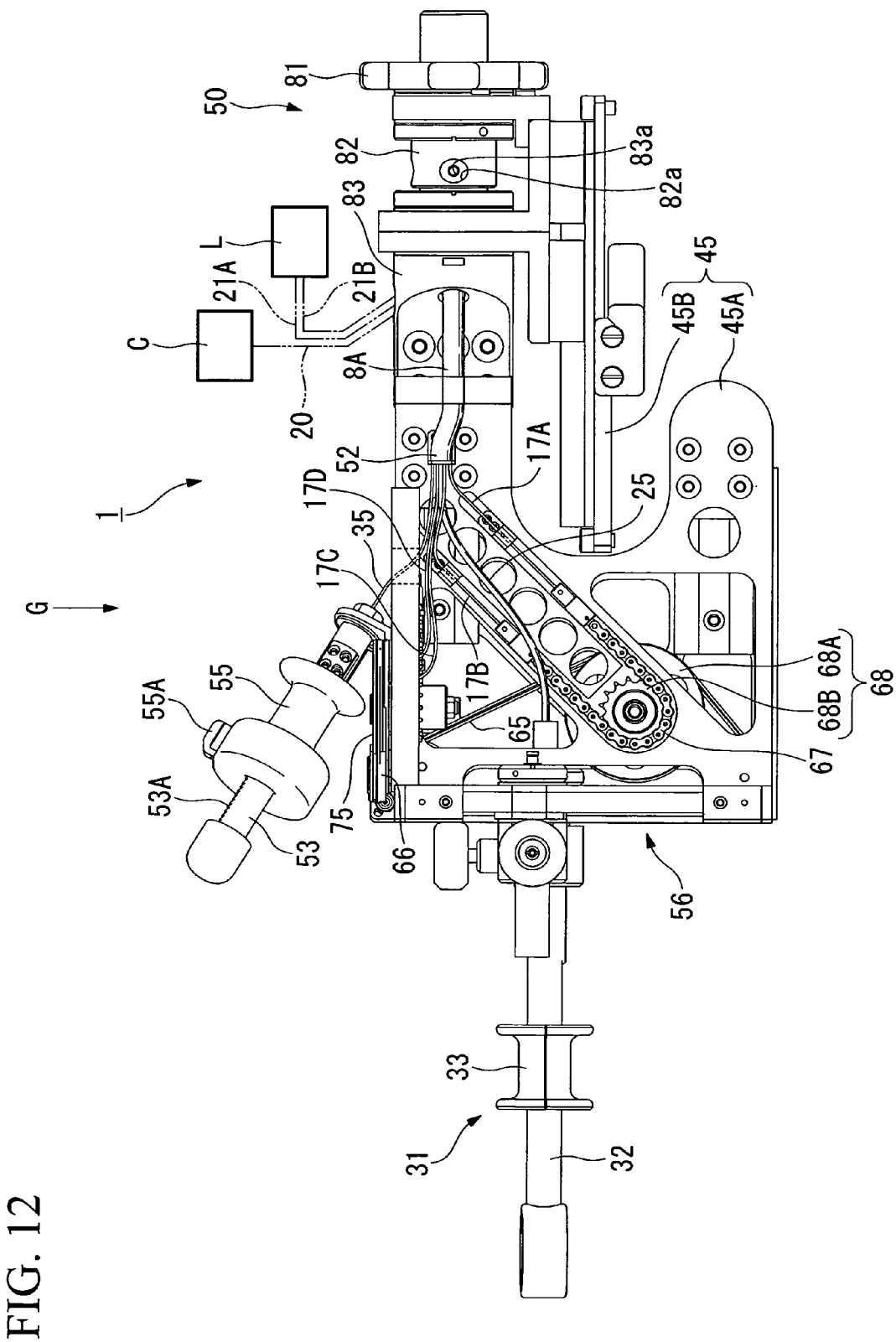
FIG. 12 is a view along direction F in FIG. 11.
Figure 13:
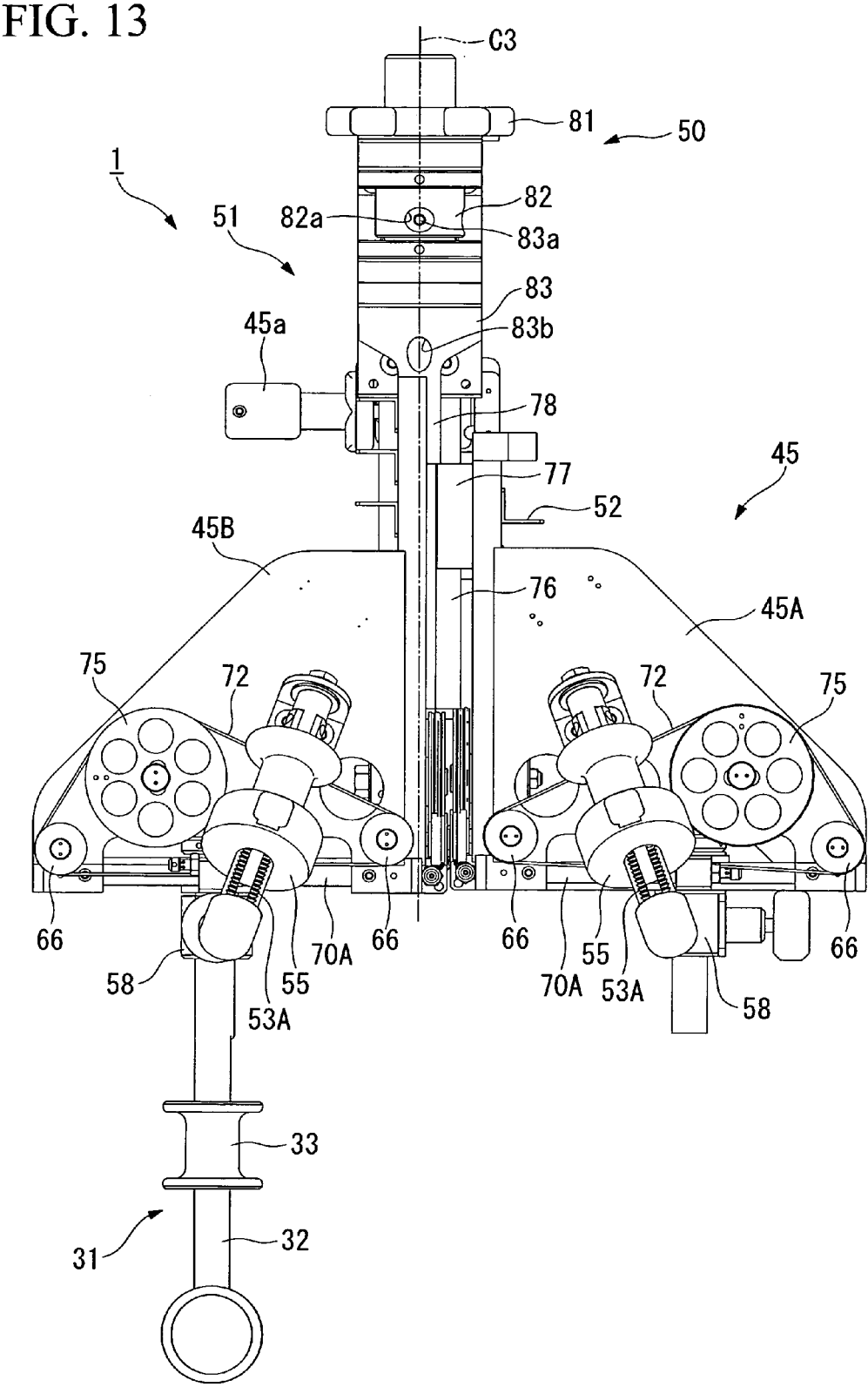
FIG. 13 is a view along direction G in FIG. 12.

As shown in FIGS. 9 though 12, the medical treatment endoscope 1 is provided with an operating part 51 having a frame 45; an open/close operating part 46 that is connected to the base end of the bending opening/closing wire 35 of the open/close mechanism 10, for carrying out advancing and retracting manipulation of the bending opening/closing wire 35; a bending operating part 47, to which the forceps operating part 31 of the gripping forceps 5 can be attached, for advancing and retracting manipulation of the bending wires 17A, 17B, 17C, and 17D that are connected to the respective bending parts 7 of the first arm member 8A and the second arm member 8B by movement of the forceps operating part 31; an advance/retract operating part 48 for advancing and retracting the sliding member 43 of the advance/retract mechanism 13 with respect to the guide member 42; and a rotation operating part 50 for connecting the base end of the first sheath 3 to the frame 45 in a manner to enable rotation.

The frame 45 is provided with a moving frame 45A where the open/close operating part 46 and the bending operating part 47 of the arm member 8A are disposed; and a fixed frame 45B where the open/close operating part 46 and the bending operating part 47 of the arm member 8B, and the rotation operating part 50 of the first sheath 3, are disposed. Arm clamps 52 for supporting the first arm member 8A and the second arm member 8B projecting from the base end of the first sheath 3 farther toward the hand-held side are respectively disposed along the central axis C3 to moving frame 45A and fixed frame 45B. In addition to the first arm member 8A and the second arm member 8B, the light guides 21A and 21B and the video cable 20 project out from the base end of the first sheath 3, and are connected respectively to a light source device L and a controller C. A fixing screw 45a for connecting and fixing in place a scope holder 86, explained below, is disposed to the bottom of the fixed frame 45B. Note that with respect to fixing with the scope holder 86, it is also acceptable to enable free sliding so that it is possible to adjust the position of the front end of the medical treatment endoscope 1 inside the body cavity by advancing and retracting the entire operating part.

The open/close operating part 46 is provided with an open/close operating part main body 53 and an open/close handle 55 to which the base end of the bending opening/closing wire 35 is connected and which can advance and retract with respect to the open/close operating part main body 53. The open/close operating part main body 53 is respectively fixed in place to the fixed frame 45B and the moving frame 45A. A rack 53A is formed at the open/close operating part main body 53 for restricting movement toward the front end side when the open/close handle 55 is pulled toward the hand-held side. The advance of the open/close handle 55 with respect to the open/close operating part main body 53 is restricted as a result of engagement of this rack 53A with a gear, not shown in the figures, that is provided inside the open/close handle 55. In this restricted state, the above-mentioned gear can be moved away and released from the rack 53A by pressing a release button 55A that is provided at the open/close handle 55. When a starting state for the open/close mechanism 10 is defined as the state in which the first arm member 8A and the second arm member 8B are closed at a position along the direction of the central axis C1 of the first sheath 3, then, in this starting state, the open/close handle 55 is set so as to be positioned toward the front end of the open/close operating part main body 53.

The bending operating part 47 is provided with a vertical bending operating part 56 for moving bending part 7 in the vertical direction, for example; a horizontal bending operating part 57 for moving the bending part 7 in a direction perpendicular to the aforementioned, i.e., moving the bending part 7 in the horizontal direction, for example; and an attachment part 58 for attaching the forceps operating part main body 32 of the forceps operating part 31 in a manner so as to enable its rotation. The attachment part 58 is connected to enable movement in the respective directions inside the each of the frames at the area of intersection between a first movement restricting member 60, which is in the form of a rectangular frame provided for causing relative displacement of the attachment part 58 in the horizontal direction only, and a second movement restricting member 61, which is in the form of a rectangular frame disposed perpendicular to the first movement restricting member 60 and provided for causing relative displacement of the attachment part 58 in the vertical direction only. Note that the bending operating parts 47 are disposed to each of the first arm member 8A and the second arm member 8B.

A vertical bending operating part 56 is provided with a pair of rod-shaped first bending guides 62A and 62B in which the longitudinal ends of the first movement restricting member 60 are engaged in a manner to enable sliding, in order to cause parallel displacement of the first movement restricting member 60 in the vertical direction; a first die part 63 that is connected to the end 60a of the first movement restricting member 60, and moves along the first bending guide 62A; a first belt member 65, in which both ends are connected to the first die part 63 so as to be in opposition to one another from the direction along the first bending guide 62A; two adjusting wheels 66 for adjusting the tension by winding the first belt member 65; a first chain belt 67 in which the bases of the bending wires 17A and 17B are connected at either end; and a first gear 68 having a small diameter part 68b in which the first chain belt 67 engages and a large diameter part 68a around which the first belt member 65 is wound.

The horizontal bending operating part 57 is provided with the same construction as the vertical bending operating part 56. In other words, the horizontal bending operating part 57 is equipped with a pair of rod-shaped second bending guides 70A and 70B in which the longitudinal ends of the second movement restricting member 61 are engaged in a manner to enable sliding, in order to cause parallel displacement of the second movement restricting member 61 in the horizontal direction; a second die part 71 that is connected to the end 61a of the second movement restricting member 61, and moves along the second bending guide 70A; a second belt member 72, in which both ends are connected with respect to the second die part 71 so as to be in opposition to one another from the direction along the second bending guide 70A; adjusting wheels 66 for adjusting the tension by winding the second belt member 72; a second chain belt, not shown in the figures, in which the bases of the bending wires 17C and 17D are connected at either end; and a second gear 75 in which the second chain belt engages and around which the second belt member 72 is wound.

The advance/retract operating part 48 is provided with a slide rail 76 for moving the moving frame 45A, to which the open/close operating part 46 and the bending operating part 47 connected to the arm member 8A are disposed, with respect to the fixed frame 45B; and a base 77 which is disposed to the moving frame 45A and engages in a sliding manner with the slide rail 76. An advance/retract restricting member 78 is disposed to the front end side of the slide rail 76. The amount of sliding of the moving frame 45A is restricted to a predetermined range as a result of the base 77 coming into contact with this advance/retract restricting member 78. This advance/retract restricting member 78 is positioned at a predetermined location so that the sliding member 43 of the advance/retract mechanism 13 does not come free from the guide member 42.

The rotation operating part 50 is disposed further toward the front end side of the frame 45 than the arm clamp 52, and is provided with a sheath connector 82, to which a rotation knob 81 is disposed and the base end of the first sheath 3 is connected; and a rotation support 83 for supporting the sheath connector 82 in a manner to enable rotation. A screw hole 83a is formed in the rotation support 83, and a through-hole 82a is formed in the sheath connector 82. The rotation of the sheath connector 82 with respect to the rotation support 83 is restricted as a result of the engagement of a stopping screw or the like at the position where the screw hole 83a and the through-hole 82a are overlapped. The amount of rotation is preferably on the order of 180 degrees to either side. Note that a through-hole 83b is disposed to the rotation support 83 for insertion of the light guides 21A and 21B and the video cable 20.

Next, the operation of the embodiment of the present invention will be explained.

Figure 5A:
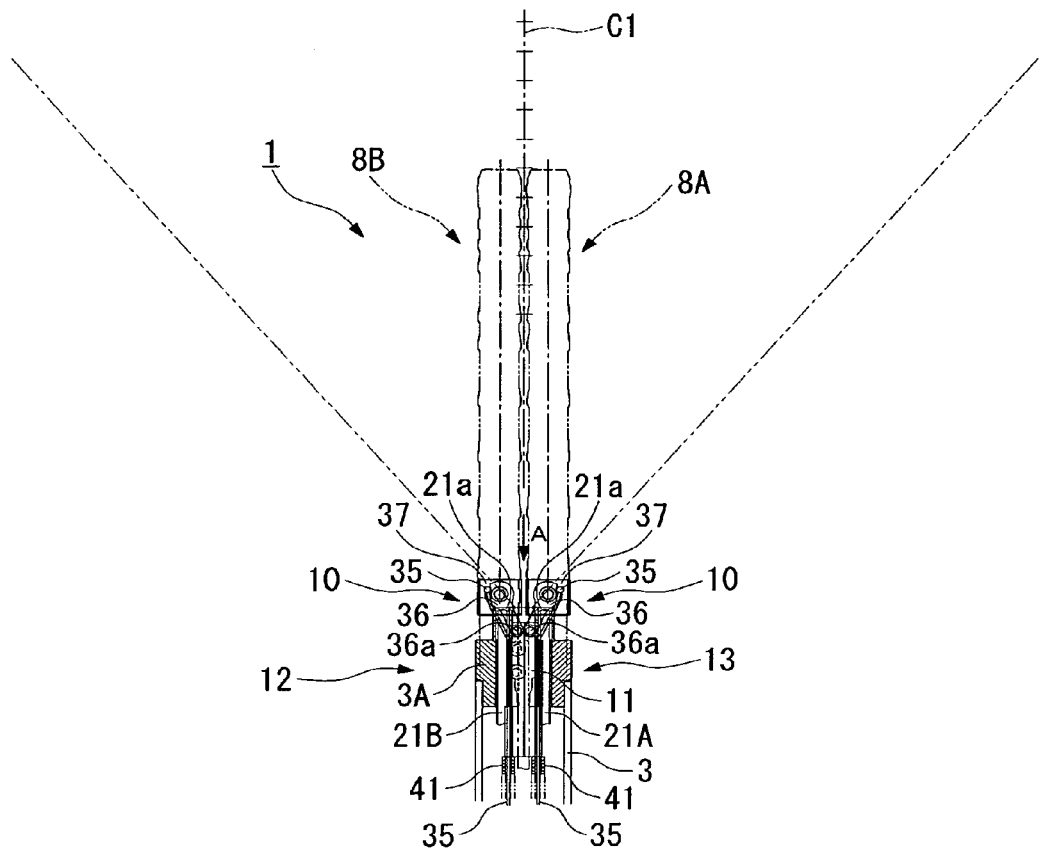
FIG. 5A is a perspective view showing the starting state of the arm member of the medical treatment endoscope according to the first embodiment.
Figure 5B:
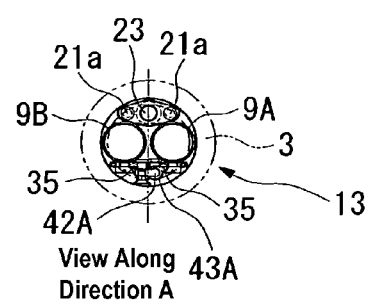
FIG. 5B is a view along direction A in FIG. 5A.
Figure 6A:
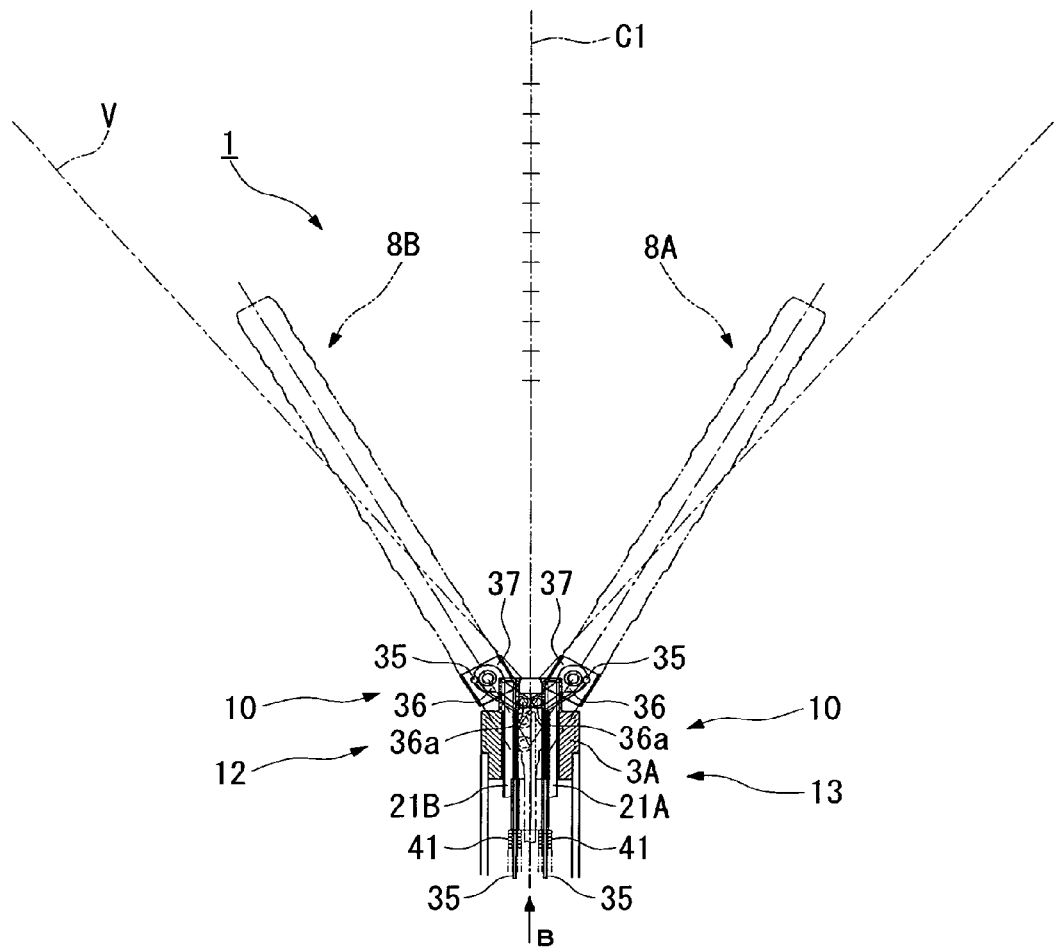
FIG. 6A is a perspective view of the front end showing the arm member of the medical treatment endoscope according to the first embodiment in the open state.
Figure 6B:
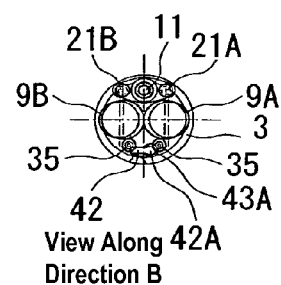
FIG. 6B is a view along direction B in FIG. 6A.
Figure 8A:
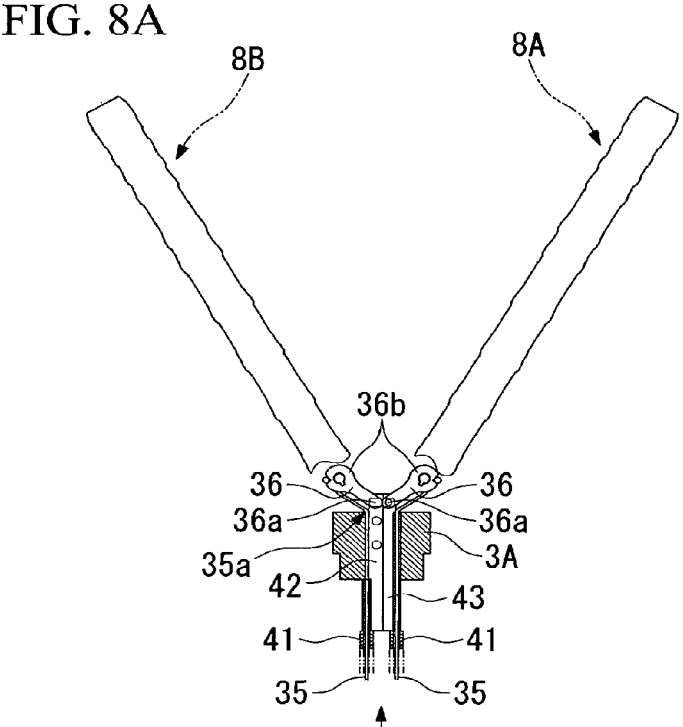
FIG. 8A is a plan view showing the open/close mechanism when the arm member of the medical treatment endoscope according to the first embodiment is in the open state.
Figure 8B:
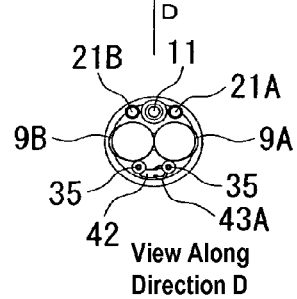
FIG. 8B is a view along direction D in FIG. 8A.

When opening the first arm member 8A and the second arm member 8B with respect to the first sheath 3 from the starting state shown in FIGS. 5A and 7A, the open/close handle 55 is slid with respect to the open/close operating part main body 53 a predetermined distance toward the hand-held side. The bending opening/closing wire 35 is thus retracted with respect to the first sheath 3 toward the hand-held side. Accompanying this, the other end 36b of the linking part 36 receives a rotational torque toward the base end side of the first sheath 3. The other end 36b side of the linking part 36 is rotated about the one end 36a by a predetermined angle in the direction away from the central axis C1 of the first sheath 3. As shown in FIGS. 6A and 8A, the support 37 rotates with respect to the first sheath 3, and opens. In this case, the position of the open/close handle 55 is fixed in place by the rack 53A of open/close operating part main body 53, and the position of the bending opening/closing wire 35 is thus fixed in place with respect to the first sheath 3.

When closing the first arm member 8A and the second arm member 8B with respect to the first sheath 3, the open/close handle 55 is advanced forward with respect to the open/close operating part main body 53, while pressing on the release button 55A of the open/close handle 55. At this time, the bending opening/closing wire 35 is advanced forward with respect to the front end side of the first sheath 3. Accompanying this, the rotational torque applied on the linking part 36 is released, and the other end 36b of the linking part 36 is rotated about the one end 36a of the linking part 36 in a direction toward the central axis C1 of the first sheath 3. As a result, the support 37 rotates with respect to the first sheath 3 and closes, i.e., resumes the starting state.

Figure 14:
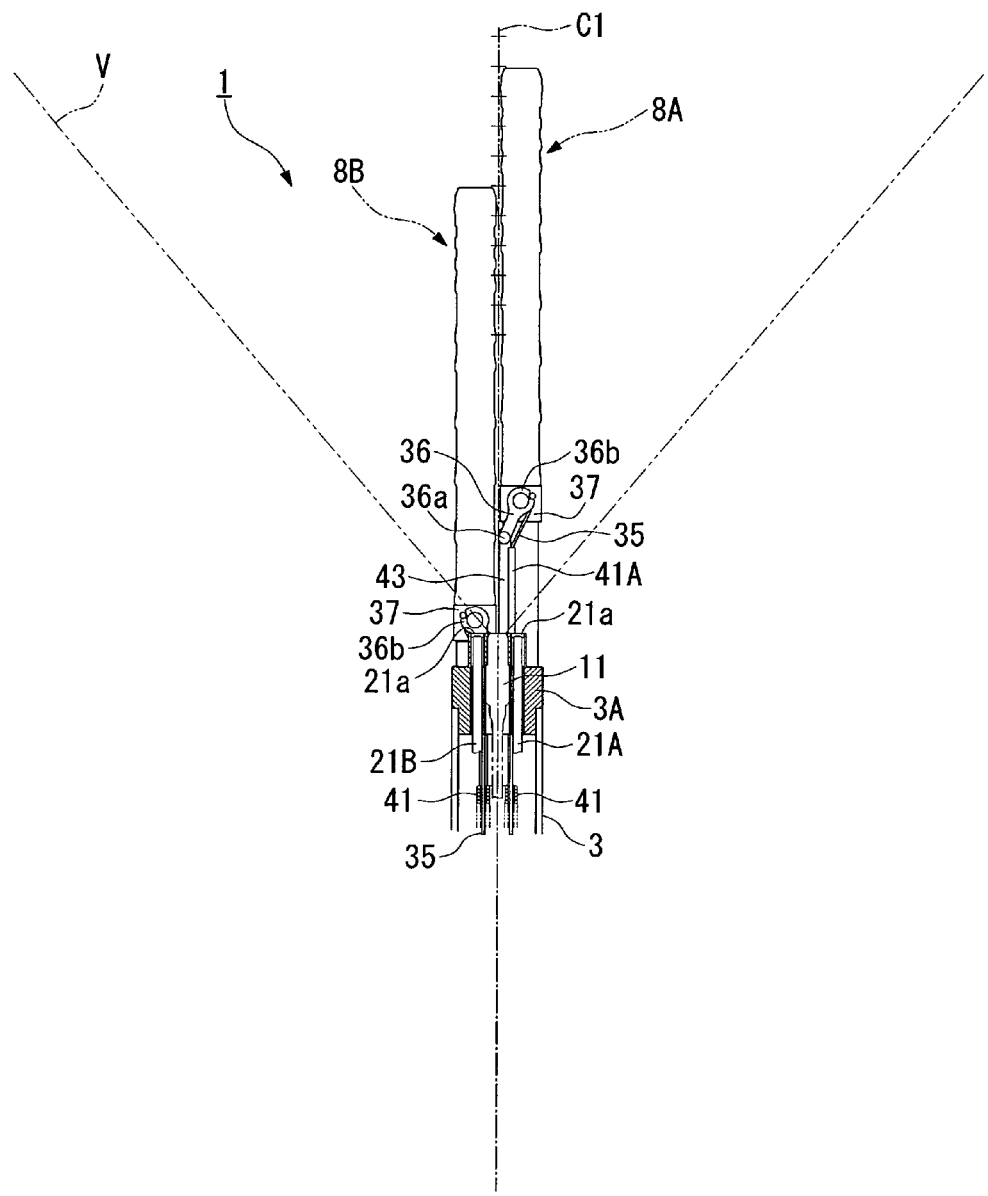
FIG. 14 is a view showing the state in which one of the arm members of the medical treatment endoscope according to the first embodiment has been moved forward with respect to the sheath.
Figure 15:
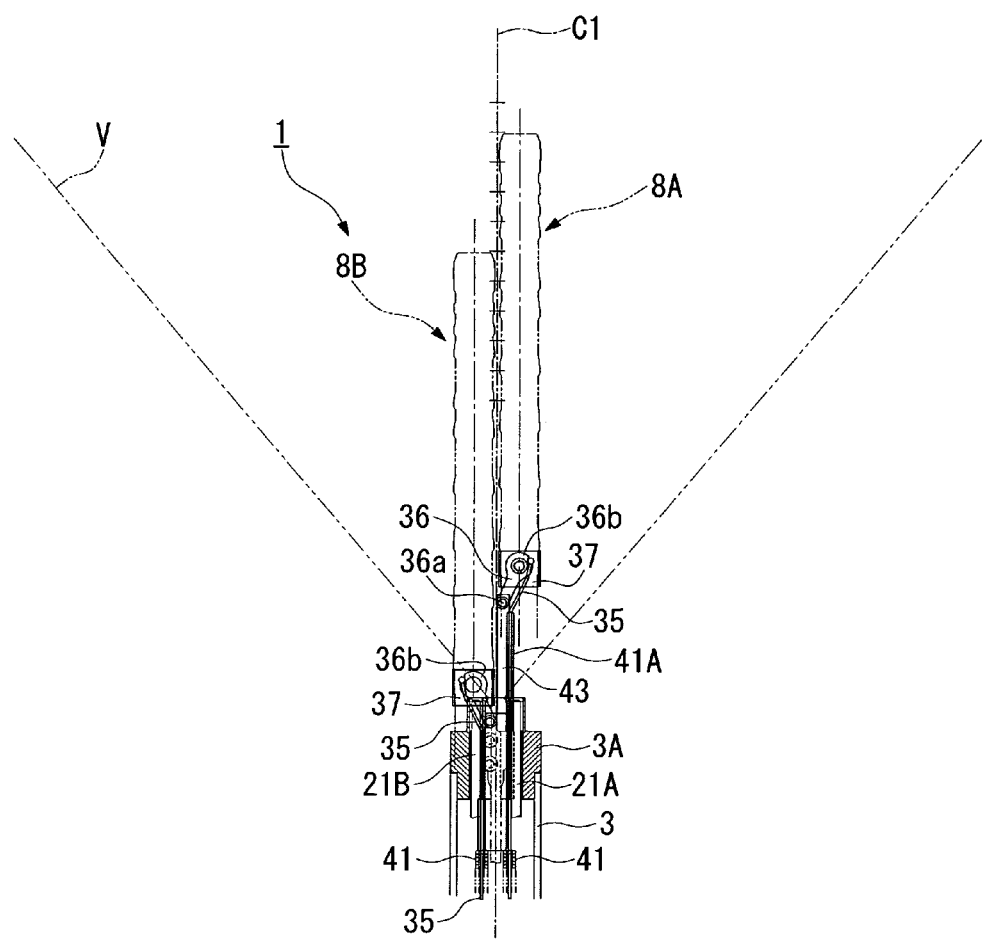
FIG. 15 is a partial perspective view of FIG. 14.
Figure 16:
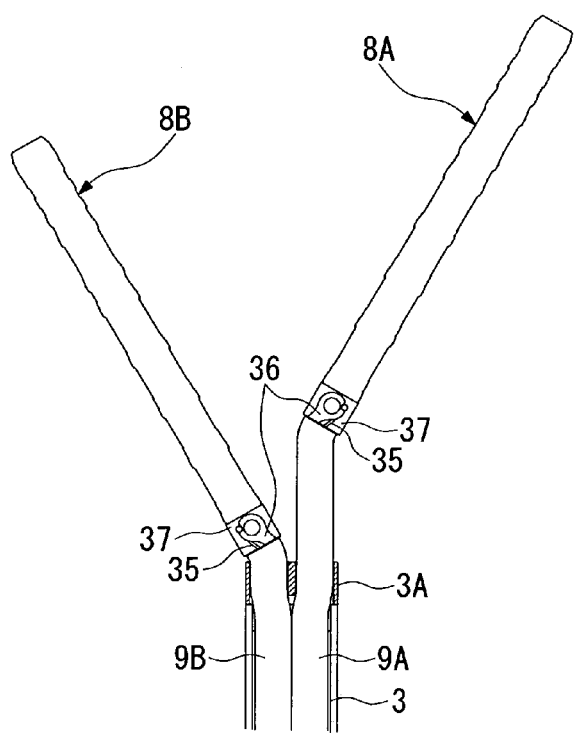
FIG. 16 is a view showing the state in which one of the arm members of the medical treatment endoscope according to the first embodiment has been moved forward with respect to the sheath, and further opened.
Figure 17:
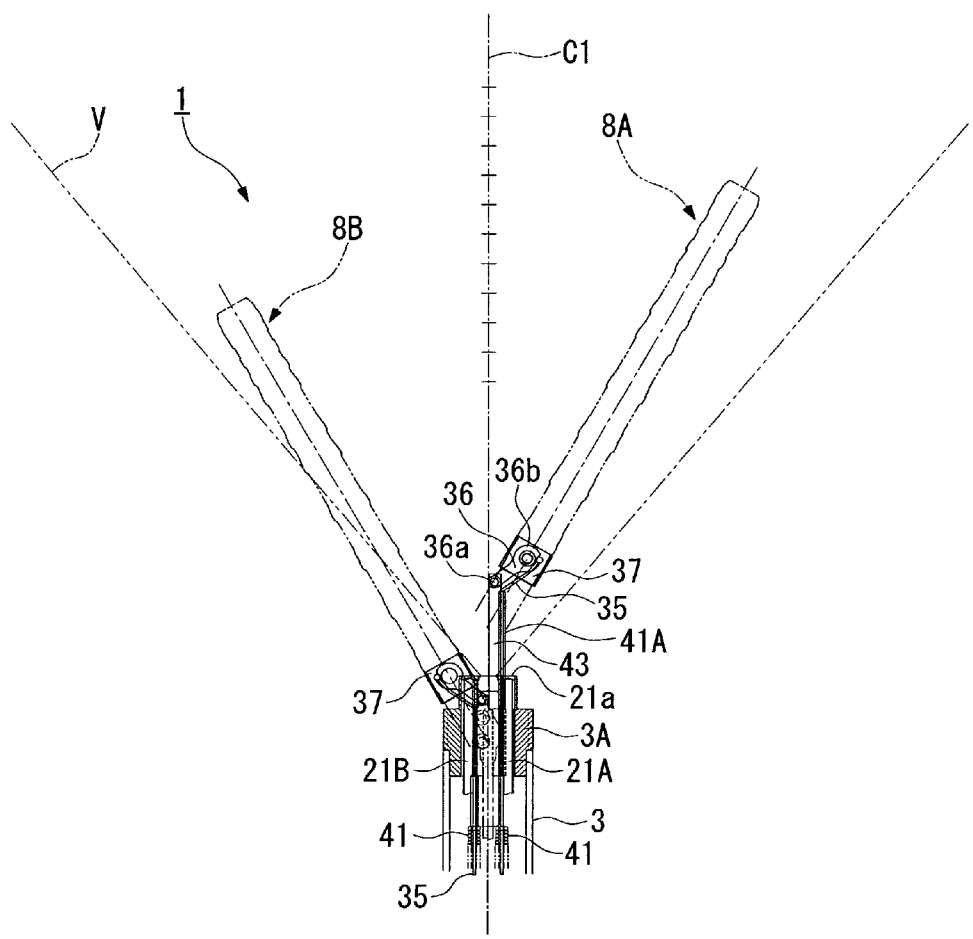
FIG. 17 is a partial perspective view of FIG. 16.

The moving frame 45A of the operating part 51 is advanced with respect to the fixed frame 45B, from the starting state shown in FIGS. 5A and 7A, when moving the first arm member 8A further toward the front end side of the first sheath 3. At this time, the base 77 advances along the slide rail 76, while the sliding member 43 of the open/close mechanism 10 moves forward with respect to the guide member 42. In this case, the entirety of the moving frame 45A moves, so that both the bending operating part 47 and the open/close operating part 46 move. Accordingly, there is no change in the open/close state and the bending state of the first arm member 8A. In this way, as shown in FIGS. 14 and 15, the first arm member 8A enters a state where it is advanced with respect to the first sheath 3.

In contrast, the moving frame 45A of the operating part 51 is retracted with respect to the fixed frame 45B when moving the first arm member 8A toward the hand-held side of the first sheath 3. At this time, the base 77 is retracted along the slide rail 76, while the sliding member 43 of the open/close mechanism 10 is retracted with respect to the guide member 42. As a result, the first arm member 8A is again disposed at the starting state position.

When bending the first arm member 8A and the second arm member 8B in the vertical direction, the vertical bending operating part 56 is manipulated. In other words, the forceps operating part 31 which is attached to the attachment part 58 is gripped and moved in the vertical direction. In this case, the attachment part 58 moves vertically within the limits of the second movement restricting member 61, while at the same time, the first movement restricting member 60 moves together with the attachment part 58 along the paired first bending guides 62A and 62B. Here, the first die part 63 also moves in the vertical direction, so that the first belt member 65 moves accompanying this, and the first gear 68 is rotated in either direction. At this time, the first chain belt 67 is rotated in either direction, and, accompanying this, one of the bending wires 17A and 17B is advanced with respect to the first sheath 3, while the other is retracted. In this way, the joint wheels 16 of the bending part 7 are inclined accompanying the movement of the bending wires 17A and 17B, and bend vertically.

In contrast, when bending the first arm member 8A and the second arm member 8B in the horizontal direction, the horizontal bending operating part 57 is manipulated. In other words, the forceps operating part 31 which is attached to the attachment part 58 is gripped and moved in the horizontal direction. In this case, the attachment part 58 moves horizontally within the limits of the first movement restricting member 60, while at the same time, the second movement restricting member 61 moves together with the attachment part 58 along the paired second bending guides 70A and 70B. Here, the second die part 71 also moves in the horizontal direction, so that the second belt member 72 moves accompanying this, and the second gear 75 is rotated in either direction. At this time, the second chain belt 73 is rotated in either direction, and, accompanying this, one of the bending wires 17C and 17D is advanced with respect to the first sheath 3, while the other is retracted. In this way, the joint wheels 16 of the bending part 7 are inclined accompanying the movement of the bending wires 17C and 17D, and bend horizontally.

When rotating the first sheath 3 with respect to the operating part 51, the rotation knob 81 of the rotation operating part 50 is gripped and rotated in the desired direction. As a result, the sheath connector 83 rotates relative to the rotation support 82, causing the first sheath 3 to rotate in the desired direction relative to operating part 51.

Figure 18:
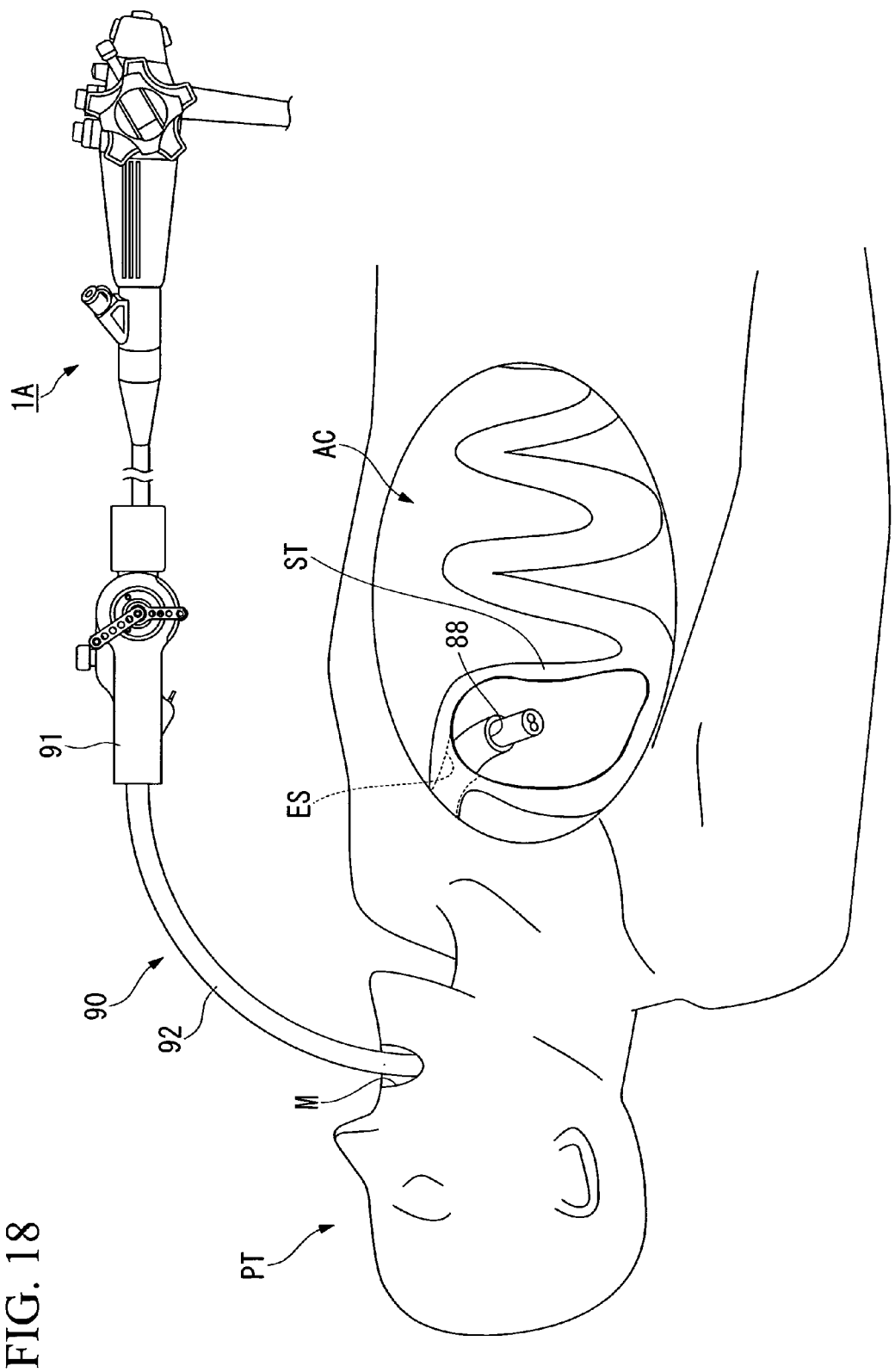
FIG. 18 is a view explaining the state in which the endoscope has been inserted into an over-tube, and then inserted into the stomach, in an operative procedure using the medical treatment endoscope according to the first embodiment.

Next, an explanation will be made with reference to FIGS. 18 through 20 of an operative procedure performed via a natural orifice using the medical treatment endoscope 1. Note that the following explanation concerns the technique of inserting the medical treatment endoscope 1 from the mouth M of a patient PT into the stomach ST, opening a hole in the wall of the stomach, and then carrying out a procedure by inserting the first sheath 3 of the medical procedure endoscope 1 into the abdominal cavity AC. In the case of the present embodiments, a predetermined procedure is performed by inserting a high frequency knife 85 into the first arm member 8A, and a gripping forceps 85 into the second arm member 8B.

The patient PT is placed on his/her back, and a typical endoscope 1A is introduced into the open-ended lumen 88 of an over-tube 90 from the base end 91 of the over-tube 90. This open-ended lumen 88 extends along the axial direction of the over-tube 90. The over-tube 90 is then inserted from the mouth M of the patient PT into the esophagus ES, and positioned in the stomach ST as shown in FIG. 18.

Next, the stomach ST is inflated by relaying air into it, after which an opening SO is formed in the stomach wall by excision. The insertion part 92 of the over-tube 90 and the endoscope 1A are introduced into the abdominal cavity AC via the opening SO. Next, the endoscope 1A is withdrawn from the over-tube 90, and the first sheath 3 of the medical treatment endoscope 1 is inserted in its place into the lumen 88 of the over-tube 90, so as to project out from the front end of the over-tube 90.

As an example here, the case will be explained where a high-frequency knife 85 is inserted into the second sheath 9A and the first arm member 8A. First, the high-frequency knife 85 is inserted into the instrument insertion channel 6, and the front end of the high-frequency knife 85 comes into contact with the bumper 15a that is provided at the front end part 15 of the first arm member 8A. The front end of the high-frequency knife 85 is urged toward the bumper 15a by pushing the high-frequency knife 85 further in from the base end side, so that the knife operating part, not shown, of the high-frequency knife attaches into the attachment part 58 of the operating part 51. In this way, advancing and retracting of the high-frequency knife 85 with respect to the first arm member 8A is restricted. Note that the high-frequency knife 85 is supported to enable free rotation with respect to the first arm member 8A and the operating part 51.

Figure 19:
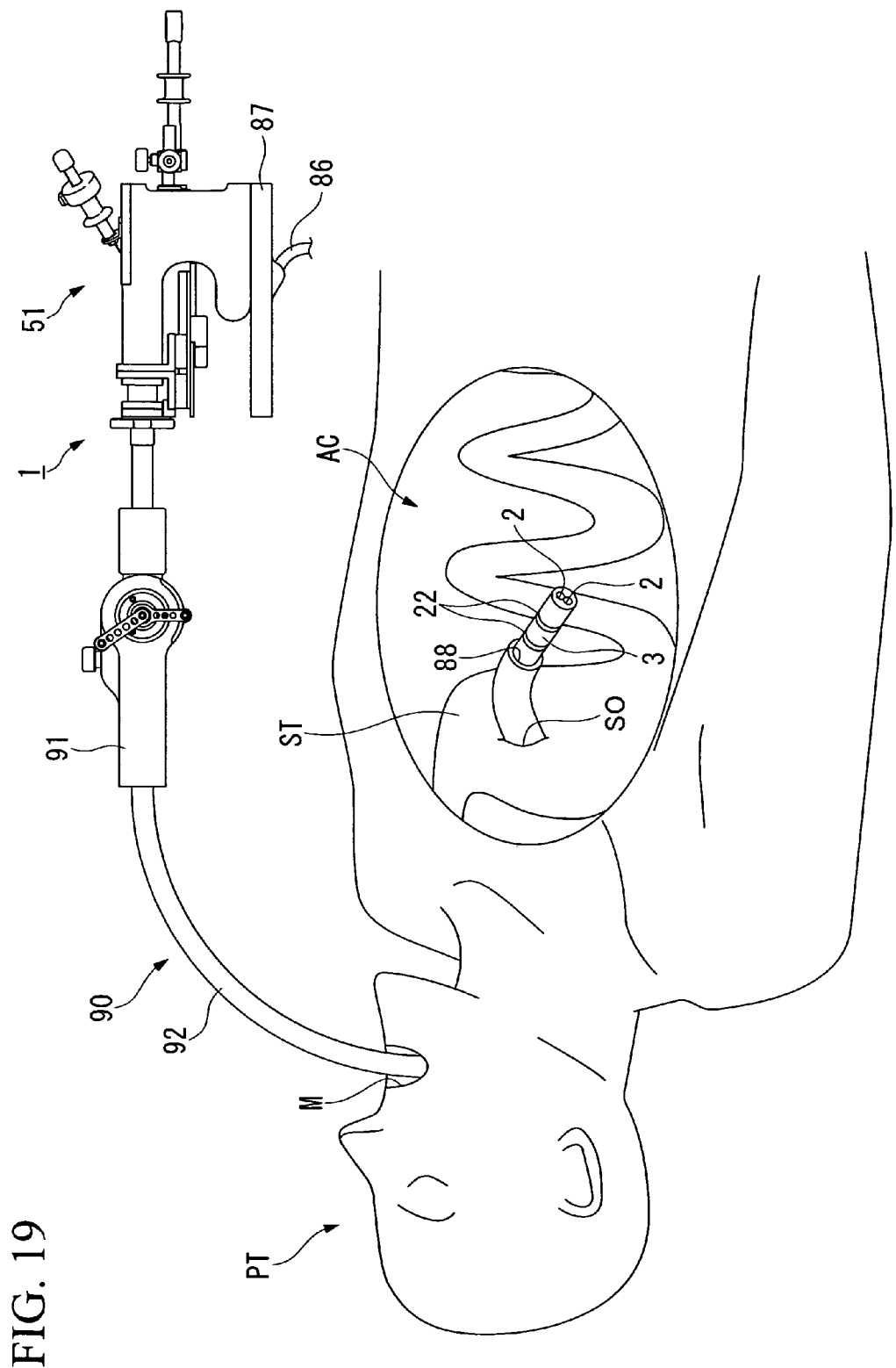
FIG. 19 is a view explaining the state in which the endoscope has been inserted into an over-tube, and then inserted from the stomach into the abdominal cavity, in an operative procedure using the medical treatment endoscope according to the first embodiment.

As shown in FIG. 19, the operating part 51 of the medical treatment endoscope 1 is mounted in a manner to enable sliding to a mount 87 that is disposed at a scope holder 86 which is attached to a bed not shown in the figures.

Figure 20:
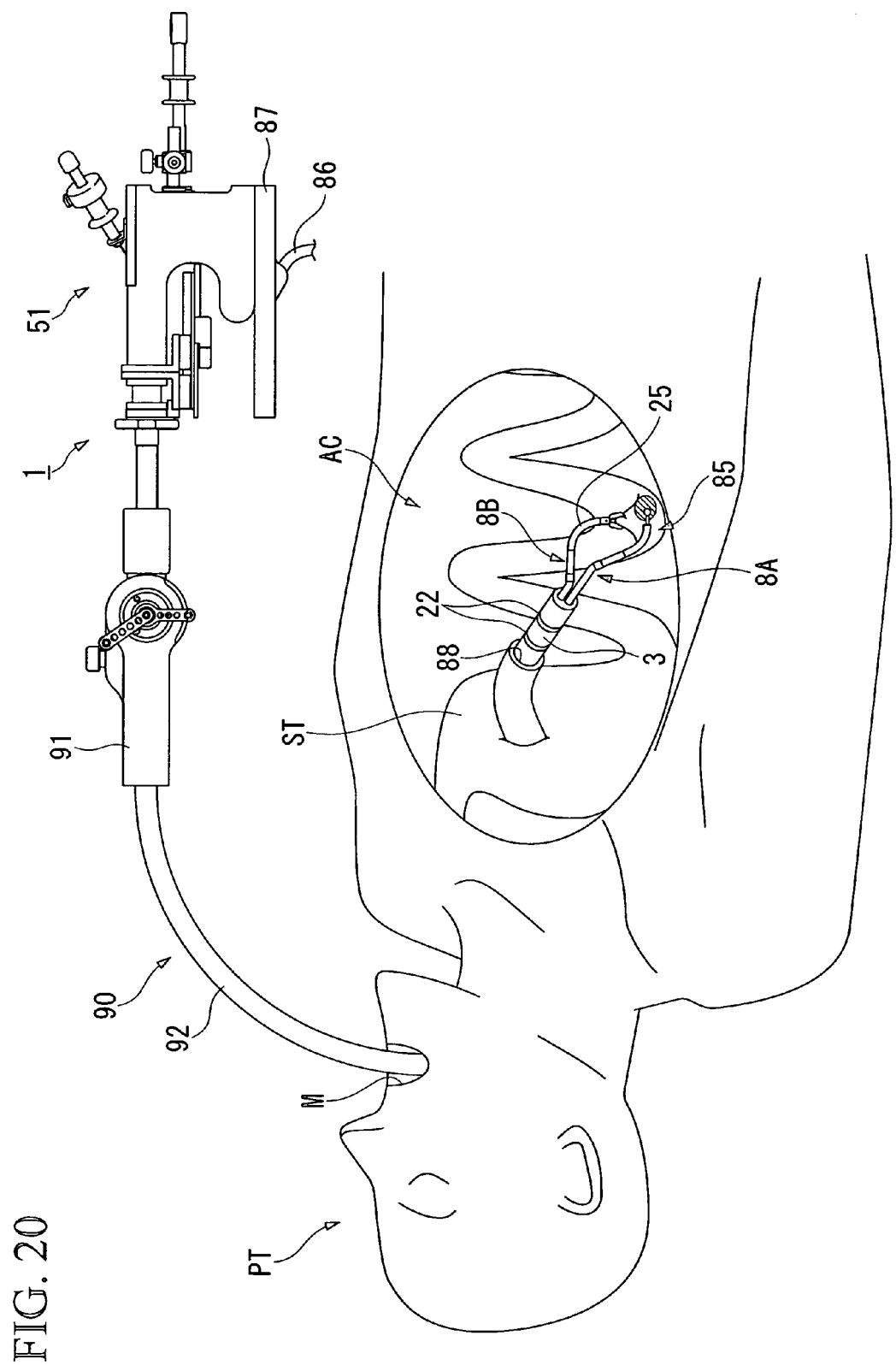
FIG. 20 is a view explaining the state in which the procedure is carried out inside the abdominal cavity, in an operative procedure using the medical treatment endoscope according to the first embodiment.

After positioning, the operations of opening/closing, bending, and advancing/retracting of the first arm member 8A and the second arm member 8B are carried out according to the desired procedures, to perform a predetermined procedure, as shown in FIG. 20. After the procedure is carried out, the medical treatment endoscope 1 is withdrawn back into the stomach ST from the opening SO in the stomach wall, and then removed from the mouth M of the patient PT.

For example, a case for gallbladder extraction will be explained.

A cervical part or bottom part of a gallbladder is grasped and retracted with a grasping forceps 5 inserted through the second arm member 8B to expose a Calot trigone.

The serous membrane of the cervical part of the gallbladder is excised a little at a time with a high frequency knife 85 inserted through the first arm member 8A. A retracting direction exerted by the grasping forceps 5 inserted through a second arm member 8B is adjusted in order to apply appropriate tensions to the excised part. Meanwhile, adipose tissue and fiber tissue including the serous membrane are peeled with the high frequency knife 85 from the cervical part of the gallbladder to the cystic duct.

After identifying the cystic duct, the periphery is totally peeled. Similarly, arteria cystica is identified and its periphery is totally peeled. Consequently, the treatment instruments used in the first arm member 8A are exchanged for a clip, which is not shown in the drawings, and the cystic duct in the vicinity of the cervical part of the gallbladder is clipped.

After replacing the treatment instruments at the first arm member 8A with the high frequency knife 85 or a pair of scissors which is not shown in the drawings, a half of the cystic duct is incised so as to observe bile outflow. Consequently, the treatment instruments used in the first arm member 8A are exchanged for an imaging tube, which is inserted into the cystic duct. After confirming the absence of a stone in the bile duct, the clip is re-applied to the first arm member 8A to double-clip the bile duct. The clip at the first arm member 8A is replaced by the high frequency knife 85 to incise the cystic duct.

A portion in the vicinity of the gallbladder and two portions in the vicinity of the nerve center are clipped by a similar method of incising the arteria cystica and the cystic duct. The arteria cystica is thus incised. The margin of the cystic duct is grasped and retracted by the grasping forceps 5 at the second arm member 8B, and the gallbladder is peeled from a gallbladder bed by operating the high frequency knife 85 attached to the first arm member 8A.

While grasping the gallbladder between the grasping forceps attached to the second arm member 8B, the medical treatment endoscope 1 is extracted from the overtube 90 to take out the liberated gallbladder. In the case of a somewhat a larger gallbladder, the bile in the gallbladder may be sucked into a smaller volume with a hollow needle which is not shown in the drawings. In addition, prior to taking out the gallbladder from the body, the medical treatment endoscope 1 may be extracted from the overtube 90, and an organ-container pouch, not shown in the drawings, grasped by the grasping forceps 5 attached to the second arm member 8B may be reinserted to contain the gallbladder.

In addition to the previously explained gallbladder extraction, the medical treatment endoscope according to the present invention can be used for various manipulations, e.g., appendectomy, gastroduodenal bypass, liver biopsy, biopsy of the pancreas, tubal interruption, and hysterectomy. After the abdominal cavity having been treated is suitably irrigated, the medical treatment endoscope 1 is retracted into the stomach ST via the wall of the opening SO. After releasing the pressure applied to the abdominal cavity AC, the medical treatment endoscope 1 is taken out of the mouth M of the patient PT.

The opening SO formed on the wall of the stomach is sutured, and the overtube 90 and the medical treatment endoscope 1 are subsequently extracted from the patient; thus, the manipulation is completed.

According to the medical treatment endoscope 1, the open/close mechanism 10 can be used to move the central axis C1 of the first arm member 8A and the second arm member 8B, which are respectively inserted into the first lumen 2 of the first sheath 3, away from the central axis C1 of the first sheath 3, further bending the bending part 7 of the first arm member 8A and the second arm member 8B. As a result, even if an instrument device such as the gripping forceps 5 is inserted into the instrument insertion channel 6, the hand-held side of the first arm member 8A and the second arm member 8B bend with respect to the front end side of the first sheath 3. Thus, the inclination of the instrument device can be deviated from the line of vision V of the image pick-up unit 11 that is disposed to the sheath front end part 3A of the first sheath 3. Accordingly, it is possible to visually confirm the front end side of the first arm member 8A and the second arm member 8B with sufficient confirmation of the line of vision V of the image pick-up unit 11. As a result, the medical procedure can be carried out safely and assuredly.

In this case, the axial force generated by advancing and retracting the bending opening/closing wire 35 with respect to the first sheath 3 can be converted through the linking part 36 of the open/close mechanism 10 into the force for opening and closing the first arm member 8A and the second arm member 8B. As a result, the first arm member 8A and the second arm member 8B can be opened or closed with respect to the central axis C1 of the first sheath 3. In particular, when opening the first arm member 8A and the second arm member 8B, the bending opening/closing wire 35 is pulled toward the hand-held side. Accordingly, it is possible to adjust the transmission of force to the bending part 7, and to finely adjust the opening angle of the first sheath 3 with respect to the central axis C1. In addition, in the case where it has been designed that the first arm member 8A and the second arm member 8B will have a suitable angle of opening with respect to the central axis C1 by means of at once pulling the open/close handle 55 toward the hand-held side until it comes into contract with the open/close operating part main body 53, it is possible to simplify the open/close operation of the first arm member 8A and the second arm member 8B.

In addition, it is possible to operate the open/close mechanism 10 by operating the open/close operating part 46 of the operating part 51 to advance and retract the bending opening/closing wire 35 with respect to the first sheath 3. In addition, by performing operations with the forceps operating part 31 for the gripping forceps 5 in a state of attachment to the bending operating part 47, it is possible to carry out not only the opening/closing operation of the pair of forceps pieces 26A and 26B of the gripping forceps 5, but also carry out the bending operation of the bending part 7, thus facilitating the procedure.

Furthermore, by sliding the moving frame 45A with respect to the fixed frame 45B in the advance/retract operating part 48, it is possible to carry out the advance/retract operation of the first arm member 8A and the second arm member 8B with respect to the first sheath 3 by advancing or retracting the sliding member 43 with respect to the guide member 42. Accordingly, the treatment scope of the gripping forceps 5 with respect to the first sheath 3 can be expanded.

Furthermore, by rotating the rotation knob 81 of the rotation operating part 50, the first sheath 3 can be rotated along with the first arm member 8A and the second arm member 8B from the base end side of the first sheath 3, and the opening/closing direction of the first arm member 8A and the second arm member 8B with respect to the first sheath 3 can be changed. Note that when it is desired to rotate a single instrument, then rotation to the desired state can be achieved by rotating the forceps operating part 31 with respect to the attachment part 58.

Because it is possible to use the support 37 of the open/close mechanism to support the first arm member 8A and the second arm member 8B farther toward the base end side than the bending part 7, the entirety of the bending part 7 can be used in the bending action, regardless of whether performing the open/close operation or the bending operation. Thus, the degree of freedom of the arm can be improved. Conversely, when the support 37 is provided along the bending part 7, the degree of freedom of each of the arm members is decreased, however, a greater force can be delivered. In addition, by manipulating the bending part 7 of the first arm member 8A and the second arm member 8B, which has a larger diameter than the diameter of the instrument insertion channel 6, the instrument can be more easily bent, and the procedure performed, than in the case where inserting a single instrument having bending capabilities through the instrument insertion channel 6 and then bending the instrument.

In addition, since the bending part 7 is employed only for bending an instrument such as the gripping forceps 5 or the like, it is possible to achieve greater bending, and output a greater force, as compared to a design that requires bending of a plurality of objects such as instruments, video cables (image guides in optical endoscopes), light guides and the like, such as seen in conventional endoscopes.

[Second Embodiment]

A second embodiment will now be explained with reference to the figures.

The second embodiment differs from the first embodiment with respect to the point that both the first arm member 8A and the second arm member 8B of a medical treatment endoscope 100 according to this embodiment are designed to advance and retract with respect a sheath 101.

Figure 21:
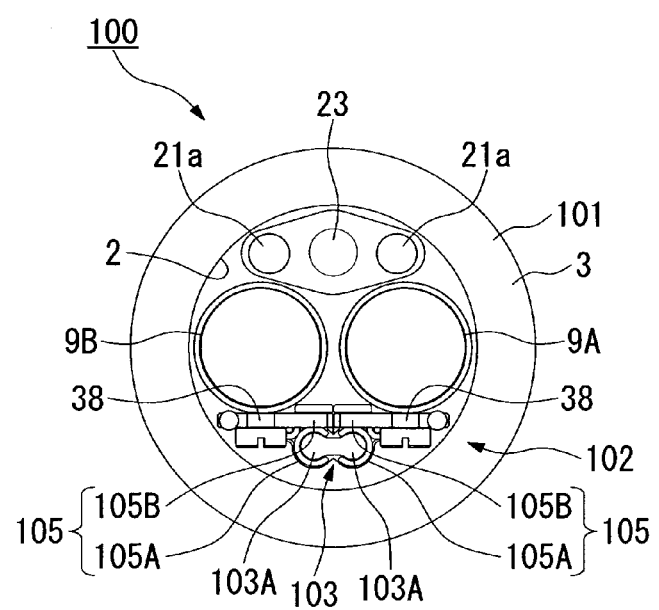
FIG. 21 is a view of the front end of the medical treatment endoscope according to the first embodiment.

Namely, as shown in FIG. 21, roughly cylindrical engaging convexities 103A are disposed at either end of a guide member 103 for an advance/retract mechanism 102, along the width direction of the guide member 103. The first arm member 8A and the second arm member 8B are connected to a sliding member 105 that has an engaging concavity 105A for engaging in a freely sliding manner with the engaging convexities 103A via a connector 105B.

As in the case of the moving frame 45A of the operating part 51 according to the first embodiment, this operating part is designed so that the open/close operating part 46 and the bending operating part 47 of not only the first arm member 8A, but also the second arm member 8B, are capable of movement with respect to the fixed frame.

Next, the effects of this embodiment will be explained. Note that the case when opening and closing the first arm member 8A and the second arm member 8B with respect to the sheath 101, the case when bending the first arm member 8A and the second arm member 8B, and the case when rotating the sheath 101, provide the same effects as those of the first embodiment.

The case when advancing or retracting the first arm member 8A and the second arm member 8B with respect to the sheath 101, as well, provides the same effects as in the case when advancing or retracting the first arm member 8A with respect to the fixed frame 45B in the first embodiment. In other words, when moving both the first arm member 8A and the second arm member 8B farther toward the front end side of the sheath 101, each of the moving frames of the operating part to which the first arm member 8A and the second arm member 8B are respectively connected is advanced with respect to the fixed frame. At this time, as in the first embodiment, the base at the operating part is advanced along the slide rail, while the sliding members 105 of the advance/retract mechanism 102 each advance with respect to the guide member 103. In this way, the first arm member 8A and the second arm member 8B are advanced with respect to the sheath 101.

On the other hand, when moving the first arm member 8A and the second arm member 8B toward the hand-held side of the sheath 101, the respective moving frames are retracted with respect to the fixed frame. At this time, the base is retracted along the slide rail, while the sliding members 105 are retracted with respect to the guide member 103. In this way, the first arm member 8A and the second arm member 8B are once again disposed at the starting state position.

The medical treatment endoscope 100 of this embodiment offers the same actions and effects as described in the first embodiment. In particular, since the first arm member 8A and the second arm member 8B are advanced and retracted with respect to the sheath 101, it is possible to ensure a wider line of vision V for the image pick-up unit 11. Furthermore, the approach angle for instruments such as gripping forceps and the like can be adjusted to a more suitable position. In addition, it is possible to increase the operating stroke for the gripping forceps, etc.

The technical scope of the present invention is not limited to the embodiments described above. Rather, various modifications may be added provided that they do not depart from the spirit of the invention.

For example, the arm members are not limited to two; rather, three or more arm members may be provided. It is also acceptable to design the front end of the second arm member so as to enable relative displacement of the gripping forceps in the advancing/retracting direction with respect to the second arm member. In addition, while an illuminating member for radiating illuminating light on the target object was formed using the light guides 21A and 21B and an illuminating lens 21a, it is also acceptable to provide an illuminating member by disposing a light emitting element, an LED for example, to the sheath front end part 3A.

[Third Embodiment]

An eighth embodiment will now be explained with reference to the figures. The medical treatment endoscope according to this embodiment represents a further improvement over the medical treatment endoscope according to the first embodiment.

Figure 22:
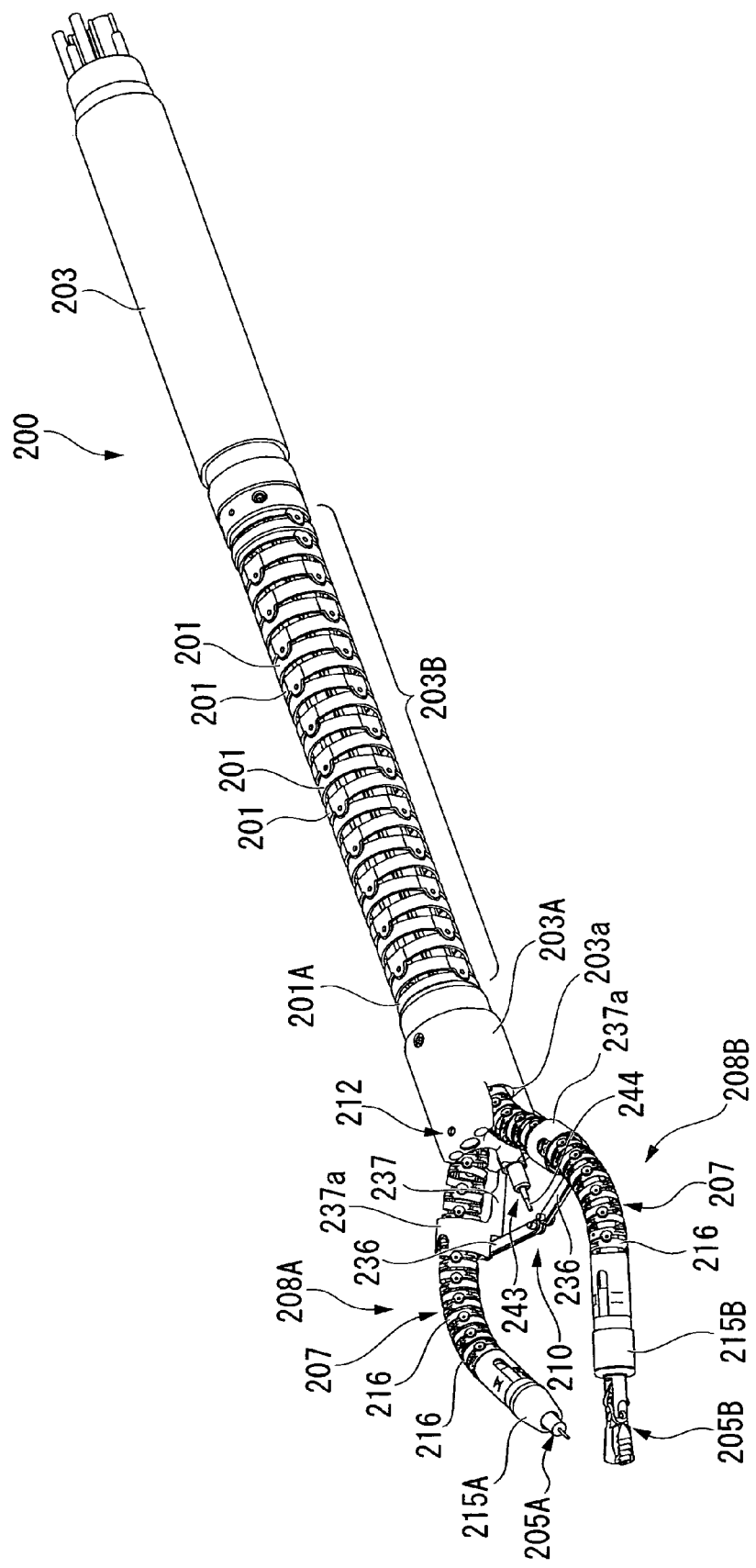
FIG. 22 is a view showing the structure of the medical treatment endoscope according to the third embodiment.

As shown in FIG. 22, and similar to the medical treatment endoscope 1 according to the first embodiment, a medical treatment endoscope 200 is provided with a first arm member 208A and a second arm member 208B that can be opened and closed. Instruments are provided at the front end parts of these first and second arm members 208A and 208B. FIGS. 22 through 25 are views showing the front end part of the endoscope in the case where the arm members 208A and 208B are spread open. FIGS. 26 through 29 are views showing the front end part of the endoscope in the case where the arm members 208A, 208B are closed. Note that in FIGS. 23 through 28, the bending parts 203B and 207 are shown with the joint wheels 201 and 216 that form these bending parts 203B and 207 covered by cover members.

Figure 30:
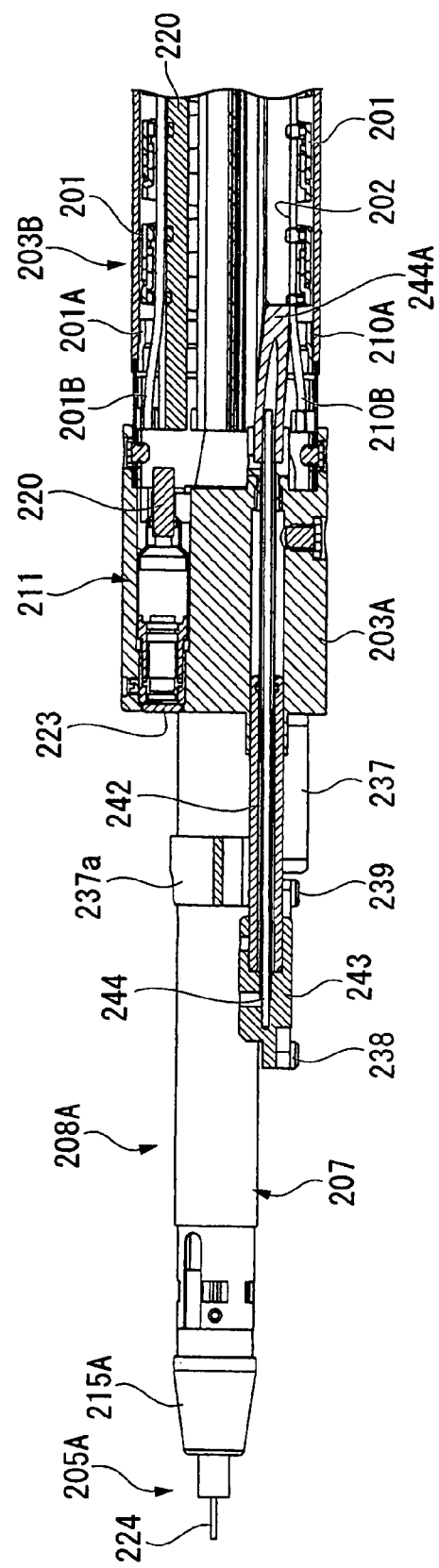
FIG. 30 is a cross-sectional view along line II-II in FIG. 26.
Figure 31:
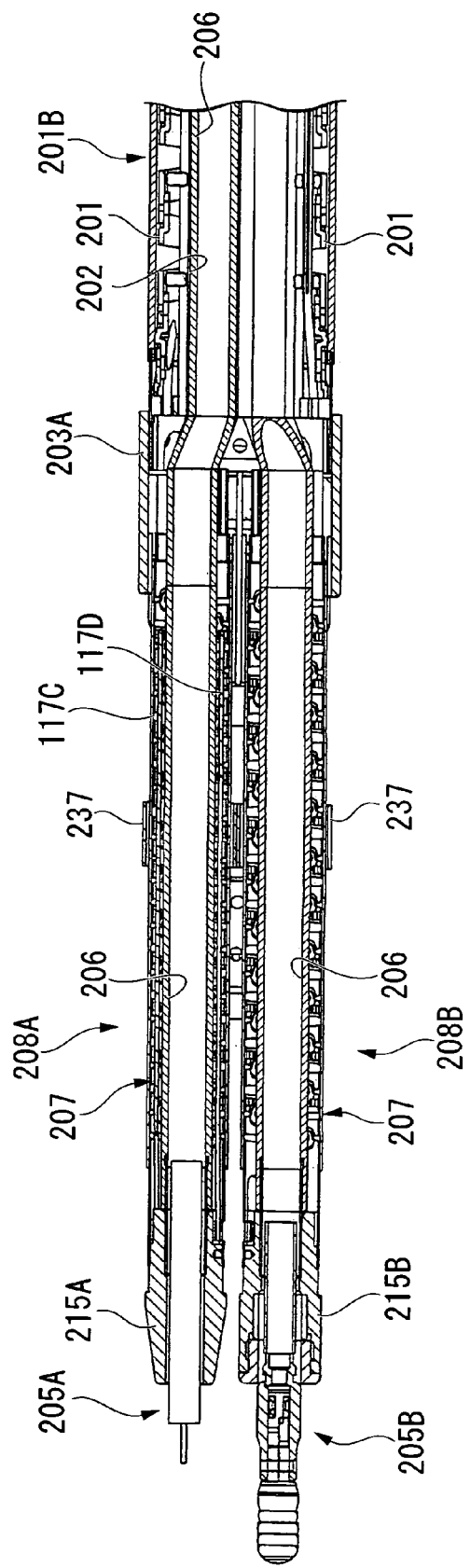
FIG. 31 is a cross-sectional view along line III-III in FIG. 27.
Figure 32:
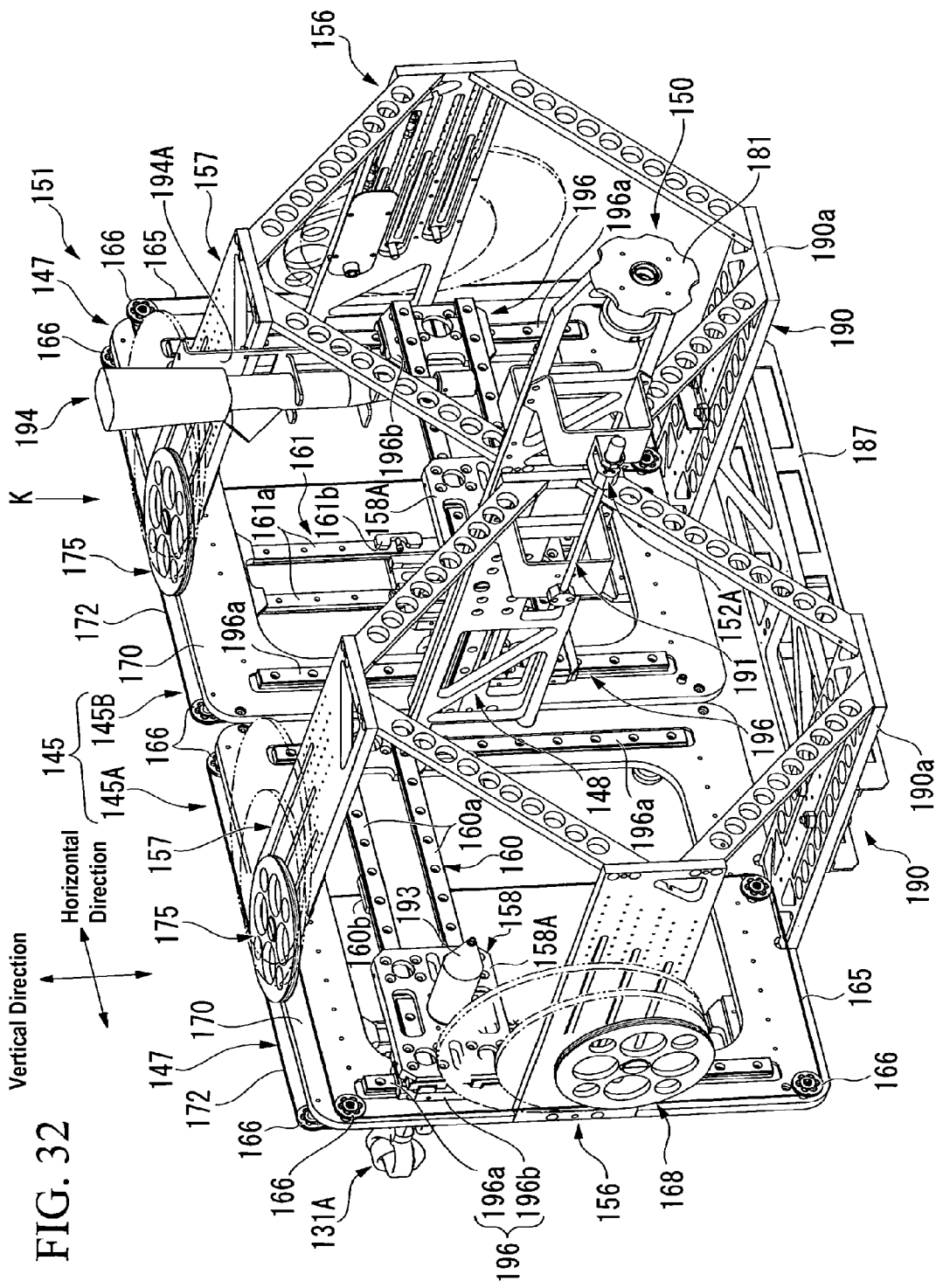
FIG. 32 is a perspective view showing the operating part of the medical treatment endoscope according to the first embodiment.
Figure 33:
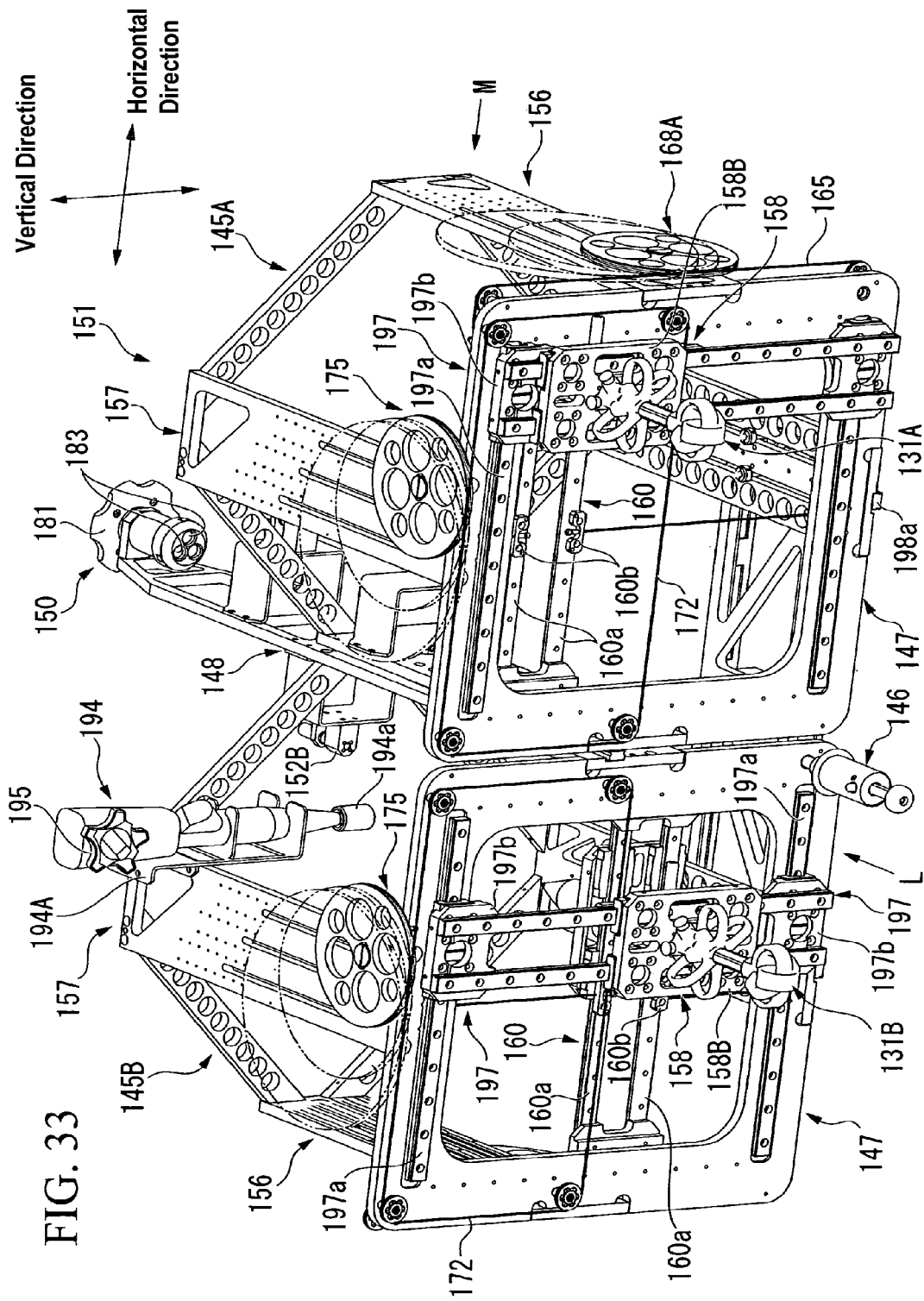
FIG. 33 is a perspective view showing the operating part of the medical treatment endoscope according to the first embodiment.

The medical treatment endoscope 200 according to this embodiment is provided with a first sheath 203 having flexibility, a sheath front end part 203A having rigidity which is provided at the front end of the first sheath 203, and a bending part 203B that is provided at a base end of the sheath front end part 203A. Openings are provided at front ends of the first sheath 203 and the bending part 203B. As shown in FIGS. 30 and 31, these openings form a first lumen 202 through which the first arm member 208A (a second sheath), the second arm member 208B (a third sheath), a video cable 220 and the like, are inserted. Furthermore, the sheath front end part 203A which is provided at the open end of the bending part 203B has an opening 203a through which the first arm member 208A and the second arm member 208B are respectively passed.

As in the case of the typical flexible endoscope, the bending part 203B is constructed such that a plurality of joint wheels 201 are continuous along the direction of the central axis of the first sheath 203 and are axially supported to enable mutual rotation, and four bending wires 201B are connected to the most distal joint wheel 201A and extend along the inside of the bending part 203B. These four bending wires 201B are each passed through the joint wheels 201 at positions so as to divide a circumferential periphery of the joint wheels 201 into quarters, and are passed through a bending wire coil that is provided inside the first sheath 203.

As shown in FIG. 31, the first arm member 208A and the second arm member 208B are provided at the sheath front end part 203A. An instrument insertion channel (a second lumen)

206, through which instruments such as gripping forceps 205B are inserted and which is open at the distal end, and a bending part 207, which projects out from the sheath front end part 203A and carries out bending operations, are disposed at each of these arm members 208A and 208B respectively. Openings 203a for enabling advance of the bending parts 207 in the lateral direction are provided on each side of the sheath front end part 203A where the first arm member 208A and the second arm member 208B are disposed. The bending part 207 is equipped with the same structure as the bending part 7 shown in FIG. 1. Namely, a plurality of joint wheels 216 are mutually axially supported to enable rotation, and are connected along the direction of the central axes of the first arm member 208A and the second arm member 208B. Furthermore, as in the case of the preceding bending part 7, bending wires 117A, 117B, 117C, and 117D extended along the inside of the bending part 207 are connected to the joint wheel 216 that is disposed farthest toward the front end. The bending wires 117A, 117B, 117C, and 117D are each inserted into and pass through the joint wheels 216 at positions so as to divide a circumferential periphery of the joint wheels 216 into quarters.

A tubular front end part 215A is attached to the front end of the bending part 207 of the first arm member 208A. The front end part 215A having an opening communicates with the instrument insertion channel 206. A high-frequency scalpel 205A projects out from the open end of the front end part 215A. And a gripping forceps 205B projects out from the open end of the front end part 215B that is attached to the second arm member 208B. The base ends of the high-frequency scalpel 205A and the gripping forceps 205B are connected to an instrument insertion part 125 which is inserted inside the instrument insertion channel 206. The high-frequency scalpel 205A is provided with a needle-shaped high-frequency knife 224 at its end that is capable of impressing high frequency power. The gripping forceps 205B has the same construction as the gripping forceps 5 according to the preceding first embodiment, and is provided with a pair of forceps pieces 226A and 226B capable of opening and closing operations via a forceps linking part 228.

In the case of this embodiment, the high frequency scalpel 205A and the gripping forceps 205B are not restricted from advancing and retracting at the front end parts 215A and 215B. Accordingly, the high frequency scalpel 205A and the gripping forceps 205B can be advanced and retracted with respect to the front end parts 215A and 215B by the advancing/retracting operation of the instrument insertion part 125 that is inserted into the instrument insertion channel 206. According to this mechanism, instruments such as the high-frequency scalpel 205A, gripping forceps 205B, etc. can be advanced or retracted with respect to an affected part regardless of the bending state of the first arm member 208A and the second arm member 208B.

Figure 23:
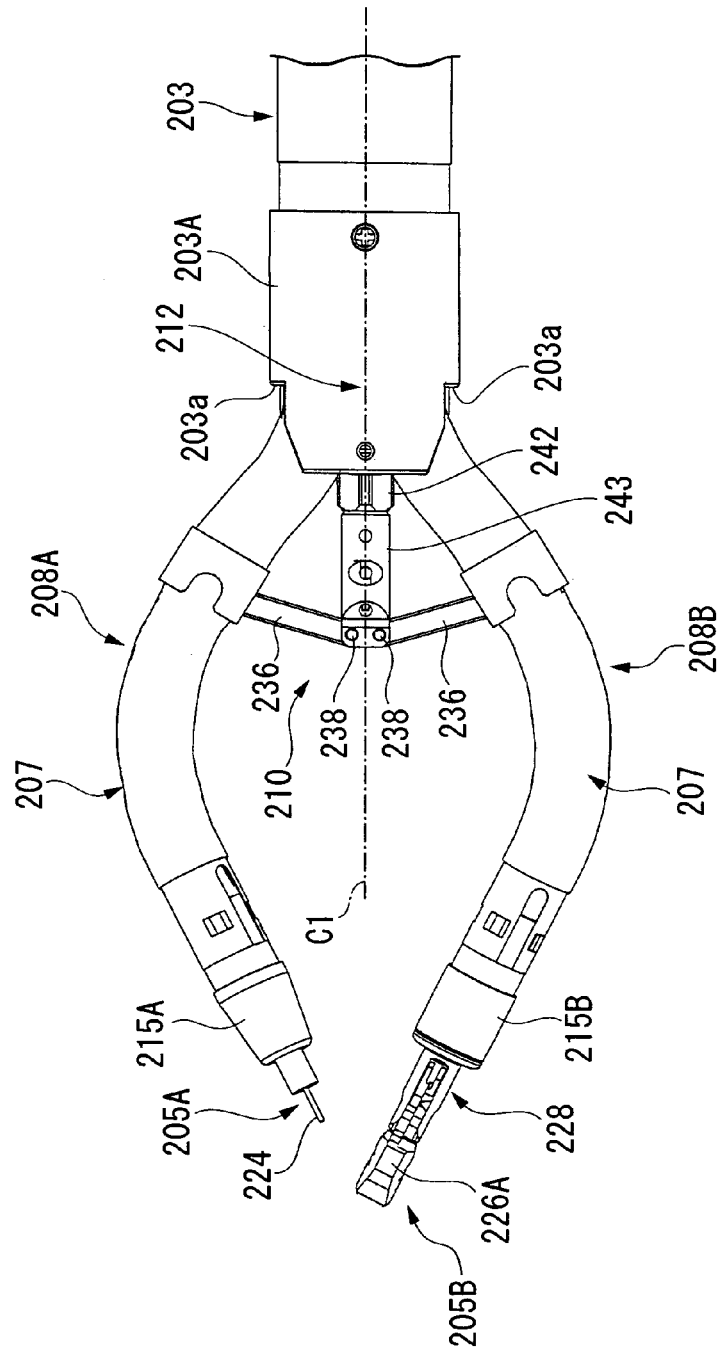
FIG. 23 is a plan view showing the structure of the front end of the medical treatment endoscope according to the third embodiment.
Figure 25:
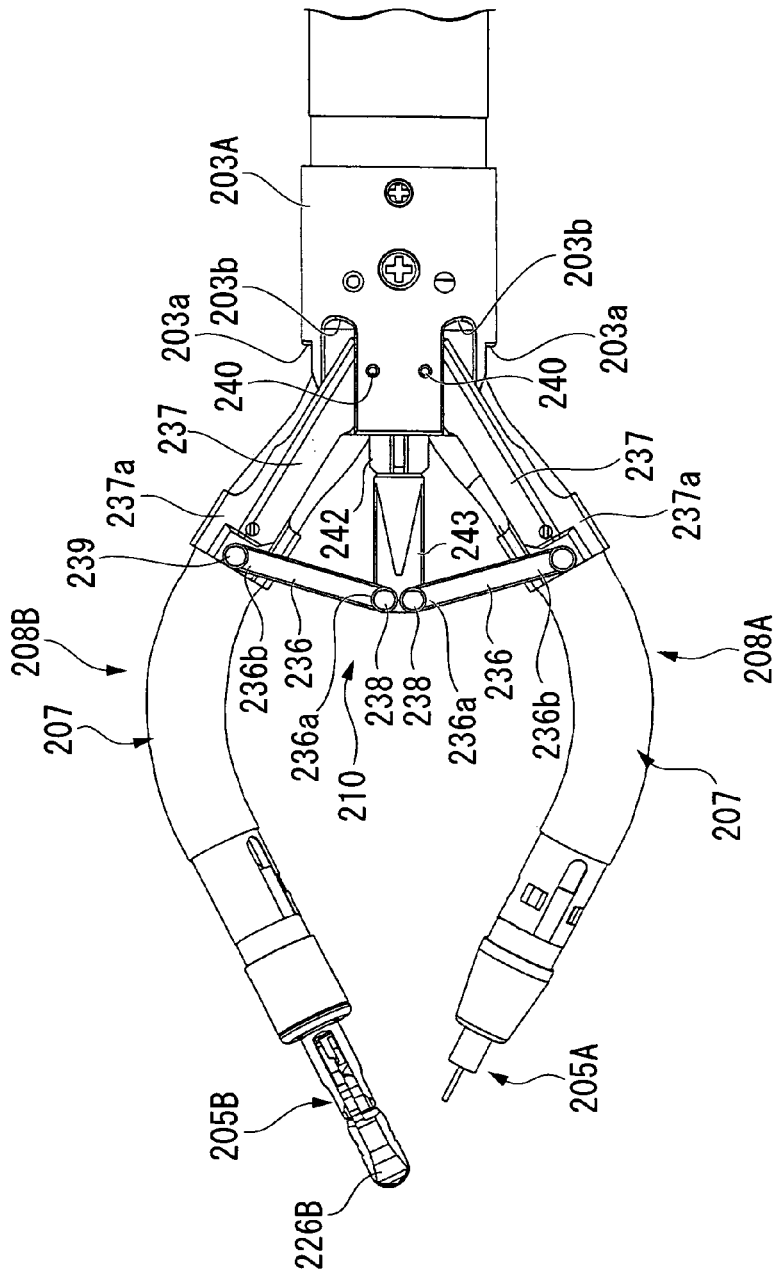
FIG. 25 is an underside view showing the structure of the front end of the medical treatment endoscope according to the third embodiment.

As shown in FIGS. 23 through 25, an open/close mechanism 210 for moving the first arm member 208A and the second arm member 208B in the directions that cause them to mutually separate or to mutually come closer together, and a viewing device 212, are provided at the sheath front end part 203A.

As shown in FIGS. 22, 23 and 25, the open/close mechanism 210 is provided with an open/close operating part 243 (a portion of which has been omitted in FIG. 22 to facilitate viewing of the figure), which is capable of advancing and retracting with respect to the first sheath 203; a sliding member 242 which supports the open/close operating part 243 and slides inside the sheath front end part 203A; two linking parts 236 to which the open/close operating part 243 is connected; and a support 237 which is connected to each of the linking parts 236 while at the same time supporting the first arm member 208A and the second arm member 208B.

The linking part 236 is formed as a plate-shaped member, the thickness and width dimensions thereof being determined so as to obtain the desired rigidity. The support 237 is constructed so that its base end side is supported to enable free rotation about a support axis 240 at the sheath front end part 203A, and to grip the first arm member 208A with link-shaped gripping members 237a that are provided at its front end side. In this way, both the first arm member 208A and the second arm member 208B are fixed in place by the gripping parts 237a of the supports 237 extending from the sheath front end part 203A, and cannot advance or retract with respect to the first sheath 203. An opening 203b is formed in the sheath front end part 203A that supports the base end side of the supports 237, for enabling advance of the supports 237 in the lateral direction.

One end 236a of the linking part 236 is supported to enable free rotation about a support axis 238 at the front end of the open/close operating part 243, and the other end is supported to enable free rotation about a support axis 239 of the gripping part 237a. A front end of the open/close operating part 243 that is connected to the one end 236a of the linking part 236 is positioned farther toward the front end of the arm members 208A and 208B than the other end 236b of the linking member 236 that is connected to support 237. In other words, the construction is provided in which the two linking parts 236 and the two supports 237 form a pantograph structure at the front end of the first sheath 203, and modification of this pantograph structure is carried out by advance and retraction of the open/close operating part 243, thereby pushing apart or pulling closed the first arm member 208A and the second arm member 208B.

As shown in FIGS. 22 and 30, the open/close operating part 243 is inserted into the sliding member 242, and is fixed in place to the portion of the bending opening/closing wire 244, which is fixed in place, that projects out from the front end of the sliding member 242. As shown in FIG. 30, the bending opening/closing wire 244 is inserted into a bending opening/closing wire coil 244A that is disposed inside the first sheath 203. As shown in FIG. 24A, the open/close operating part 243 is disposed to an opposite side from the viewing device 212, interposing the first arm member 208A and the second arm member 208B therebetween. The open/close operating part 243 is disposed closer to the central axis of the first sheath 203 than to the central axis of the first arm member 208A and the second arm member 208B.

As shown in FIGS. 24A and 30, the viewing device 212 is provided with an image pick-up unit 211 and two illuminating members 221A and 221B which are disposed on either side of the image pick-up unit 211. The image pick-up unit 211 is provided with an objective lens (optical member for viewing) 223 that is disposed at the front end surface of the sheath front end part 203A, and is connected to a video cable 220 that is inserted into the first sheath 203. The illuminating members 221A and 221B include an illuminating lens (optical member for illumination) that is disposed lateral to the objective lens 223. The objective lens 223 and the illuminating lens are disposed farther toward the front end of the bending part 207 than the position where the base end of the bending part 207 is fixed in place to the sheath front end part 203A.

Next, the operating part of the medical treatment endoscope 200 will be explained. As shown in FIGS. 32 through 36, this medical treatment endoscope 200 is provided with an operating part 151 that has a frame 145, which includes a moving frame 145A and a fixed frame 145B, and a mount 187 on which the frame 145 is mounted. The moving frame 145A and the fixed frame 145B are connected to the mount 187 via a slide mechanism 190 that is provided at their respective underbodies. The slide mechanism 190 includes slide rails 198a that are provided at a mount 187 side of base wall members 190a of the moving frame 145A and the fixed frame 145B, and a slide block 198b that is provided at the frame 145 side of the mount 187 and engages with the two slide rails 198a in a manner that enables sliding. The moving frame 145A and the fixed frame 145B are connected via a sliding mechanism 148 in which a slide rail 148a, provided at a lateral surface of the fixed frame 145B, and a slide block 148b, provided at a lateral surface of the moving frame 145A, engage in a manner to enable sliding. The slide rail 148a is disposed parallel to the slide rail 198a of the slide mechanism 190.

The moving frame 145A and the fixed frame 145B are each provided with the slide mechanism 190, and are connected via the slide mechanism 148. As a result, the moving frame 145A and the fixed frame 145B can both be made to slide with respect to the mount 187. However, in the case of this embodiment, the base wall member 190a of the fixed frame 145B is fixed to the mount 187, and only the moving frame 145A is able to slide with respect to the fixed frame 145B and the mount 187 via the slide mechanisms 148 and 198.

Figure 34:
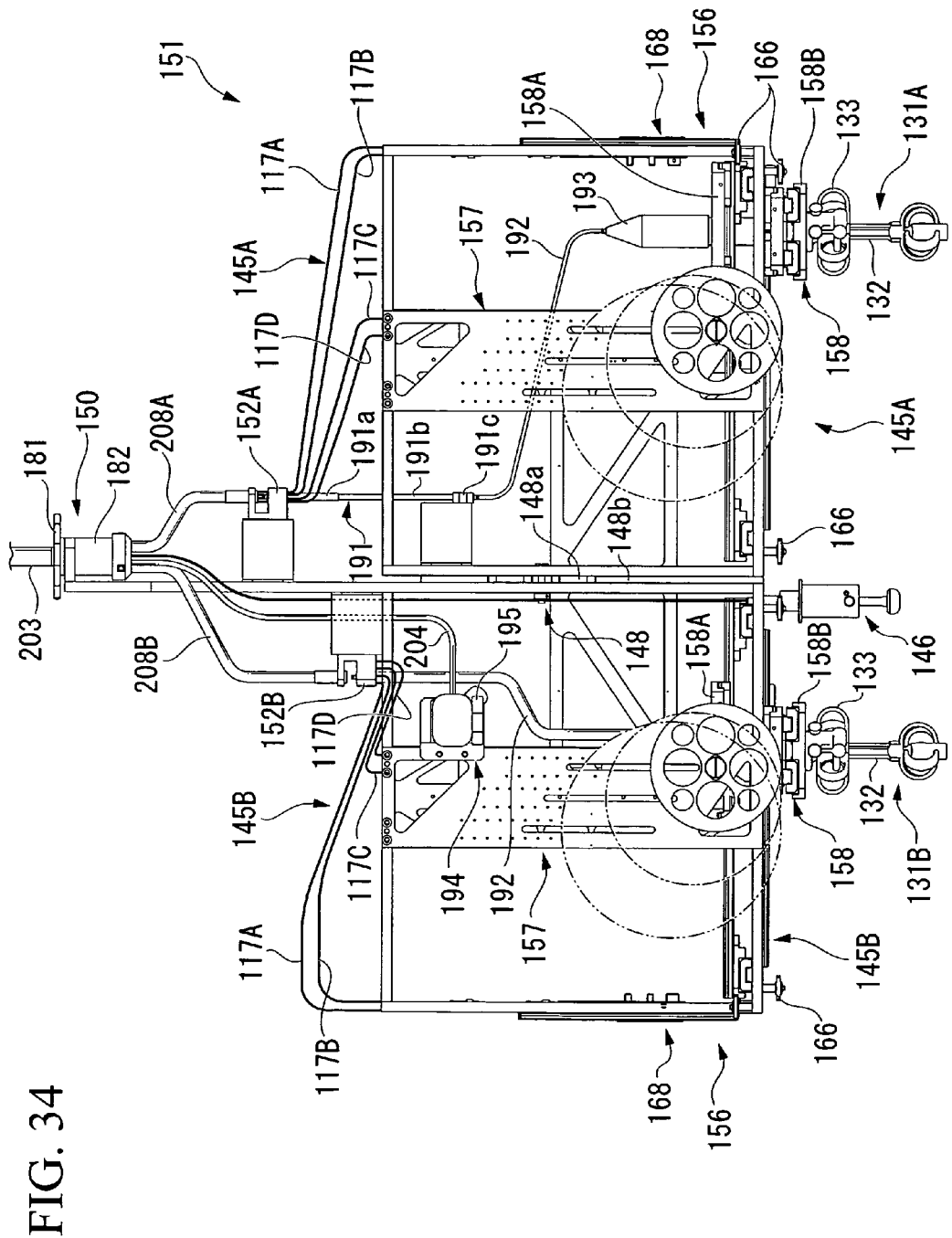
FIG. 34 is a view along direction K in FIG. 32.
Figure 35:
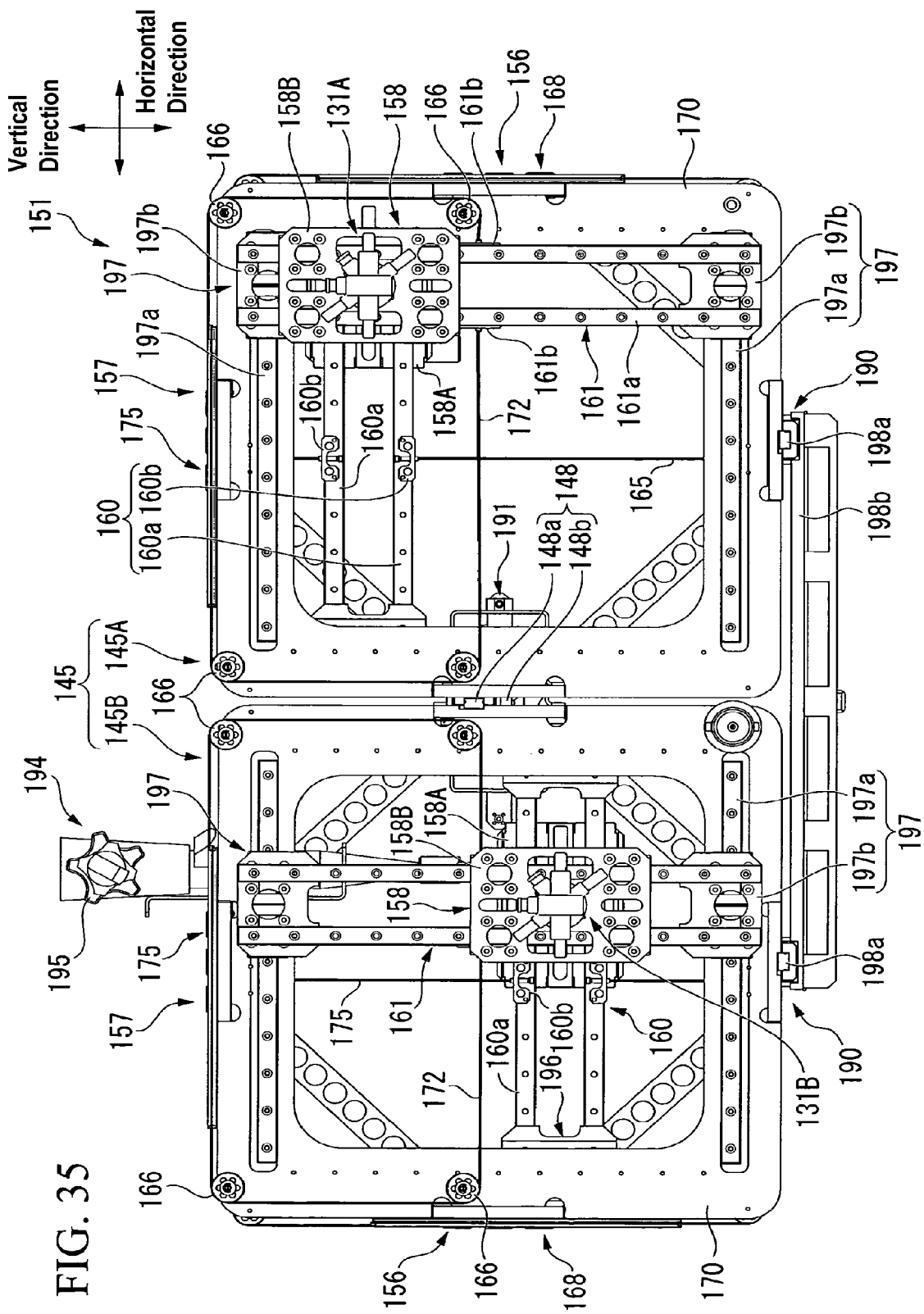
FIG. 35 is a view along direction L in FIG. 33.
Figure 36:
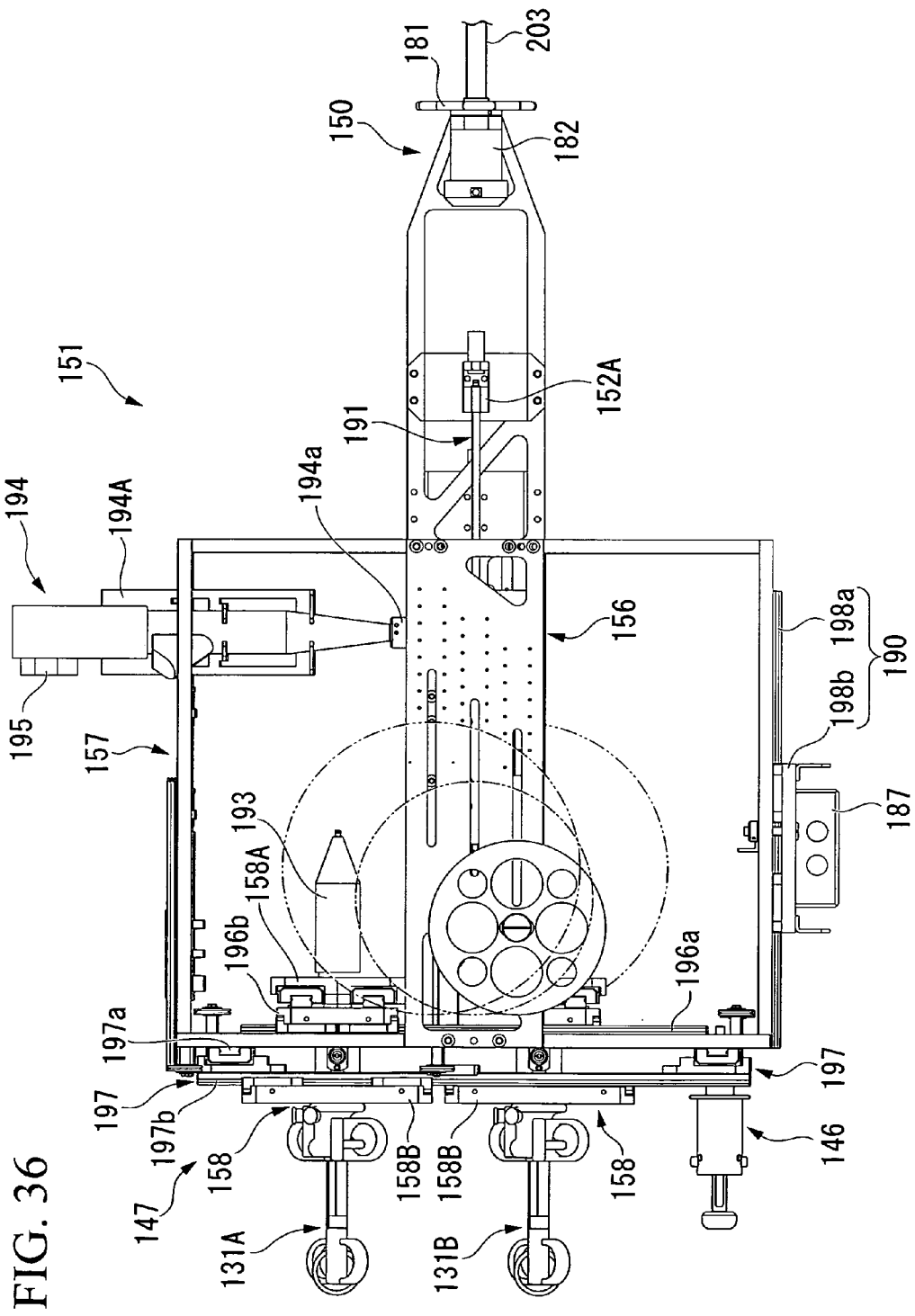
FIG. 36 is a view along direction M in FIG. 33.

The moving frame 145A is provided with a bending operating part 147 for carrying out bending operation of the first arm member 208A. The instrument operating part 131A of the high frequency scalpel 205A can be attached to and released from this bending operating part 147. On the other hand, the fixed frame 145B is provided with an open/close operating part 146 for operating the open/close mechanism 210; a bending operating part 147 for carrying out bending operation of the second arm member 208B; a sheath operating part 194 for carrying out bending operation of the bending part 203B; a rotation operating part 150 which connects the base end of the first sheath 203 to the frame 145 in a manner to enable free rotation; a first arm clamp 152A for supporting the first arm member 208A that extends out from the base end of the first sheath 203; a sheath advance/retract part 191 that is connected on the side of the first arm clamp 152A that is opposite the rotation operating part 150; and a second arm clamp 152B for supporting the second arm member 208B that extends out from the base end of the first sheath 203. Note that while a plurality of sheaths and wires are pulled around the operating part 151 of the medical treatment endoscope 200 shown in FIGS. 32 through 36, these are shown in FIG. 34, but omitted from the other figures for easier review of these drawings.

Respective bending operating parts 147 are provided corresponding to the first arm member 208A and the second arm member 208B. The bending operating part 147 is provided with a roughly rectangular frame member 170; a vertical bending operating part 156 for moving the bending part 207 in a vertical direction, for example; a horizontal bending operating part 157 for moving the bending part 207 in a direction perpendicular to the moving direction of the vertical bending operating part 156, i.e., a horizontal direction, for example; and an attachment part 158 for attaching the instrument operating parts 131A and 131B in a manner so as to enable rotation. The attachment part 158 is constructed such that the two slide blocks 158A and 158B are disposed opposite one another, and so as to be fixed in place by a tubular member 193 which passes through these slide blocks 158A and 158B. The slide block 158A is constructed to be able to slide in the horizontal direction after engaging with the two slide rails 160a that form the first movement restricting member 160 which is provided to permit relative displacement of the attachment part 158 in the horizontal direction only. The slide block 158B is constructed to be able to slide in the vertical direction after engaging with the two slide rails that form the second movement restricting member 161 which is provided to permit relative displacement of the attachment part 158 in the vertical direction only.

The instrument operating parts 131A and 131B are provided with an instrument operating part main body 132 to which the instrument insertion part 125 is connected, and an instrument handle 133 which is disposed to freely advance and retract with respect to the instrument operating part main body 132.

The vertical bending operating part 156 is provided with first bending guides 196 for causing relative displacement of the first movement restricting member 160 in the vertical direction; a first belt member 165 connected to first die parts 160b that are provided at the center along the longitudinal direction of the two slide rails 160a that form the first movement restricting member 160; four adjusting wheels 166 for adjusting the tension by winding the first belt member 165; a first gear 168 that is connected to the first belt member 165; and a first chain belt 167 which is connected to the first gear 168.

The first bending guide 196 is provided with two slide rails 196a that are equipped at the frame body of the frame member 170, and slide blocks 196b that engage with the two slide rails 196a respectively in a manner to enable sliding, and which are connected at either end of the two slide rails 160a of the first movement restricting member 160.

Figure 41:
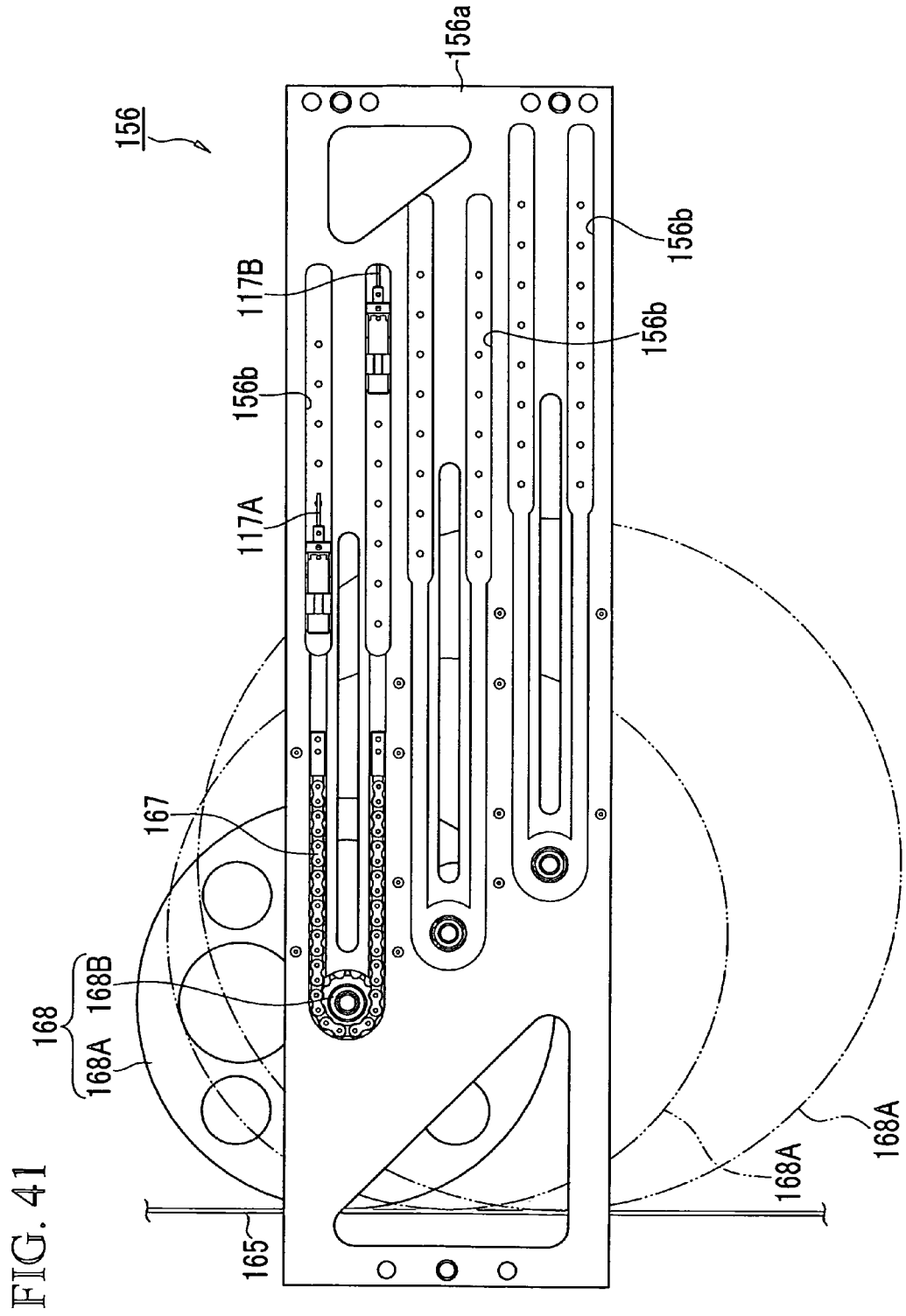
FIG. 41 is a view showing the essential part of the vertical bending operating part.

The ends of the first belt member 165 are each connected to the first die parts 160b via four adjusting wheels 166. The first chain belt 167 and the first gear 168 are attached to a plate-shaped gear box 156a, as shown in FIG. 41. The large diameter parts 168A of the first gear 168 that are connected to the first belt member 165 are attached to one surface side of the gear box 156a, and the small diameter parts 168B, which have the same axes as the large diameter parts 168A, are disposed inside grooves 156b that are formed in the other surface side of the gear box 156a. The first belt member 165 is fixed in place at the outer peripheral surface of the large diameter parts 168A. When the first movement restricting member 160 moves due to an operational input at the bending operating part 131, the first belt member 165 is pulled in one direction accompanying this, and the large diameter parts 168A begin to rotate. The first chain belt 167 which is housed inside the groove 156b engages with the small diameter part 168B. The bending wires 117A and 117B which extend from the first sheath 203 are each connected to an end of the first chain belt 167.

In the case of this embodiment, three sets of grooves 156b for housing the first chain belt 167 and the small diameter parts 168B in the gear box 156a are prepared. By pairing these with the different diameter large diameter parts 168A, it is possible to select a reduction gear ratio at the vertical bending operating part 156. This reduction gear ratio is determined based on a force required at the bending part 207 which performs the bending operation through bending wires 117A and 117B, and a force required for an operation of the bending operating part 147, these required forces being values that can be known in advance.

The horizontal bending operating part 157 is provided with the same construction as the vertical bending operating part 156. In other words, the horizontal bending operating part 157 is provided with second bending guides 197 that are connected to two ends of a longitudinal direction of the second movement restricting member 161 for causing movement of the second movement restricting member 161 in the horizontal direction; a second belt member 172 connected to second die parts 161b that are respectively provided at the center along the longitudinal direction of the two slide rails 161a that form the second movement restricting member 161; four adjusting wheels 166 for adjusting the tension by winding of the second belt member 172; a second gear 175 that is connected to the second belt member 172; and a second chain belt 173.

The second bending guide 197 is provided with two slide rails 197a that are provided at the frame body of the frame member 170, and slide blocks 197b that engage with the two slide rails 197a respectively in a manner to enable sliding, and which are connected at either end of the two slide rails 161a of the second movement restricting member 161.

Figure 42:
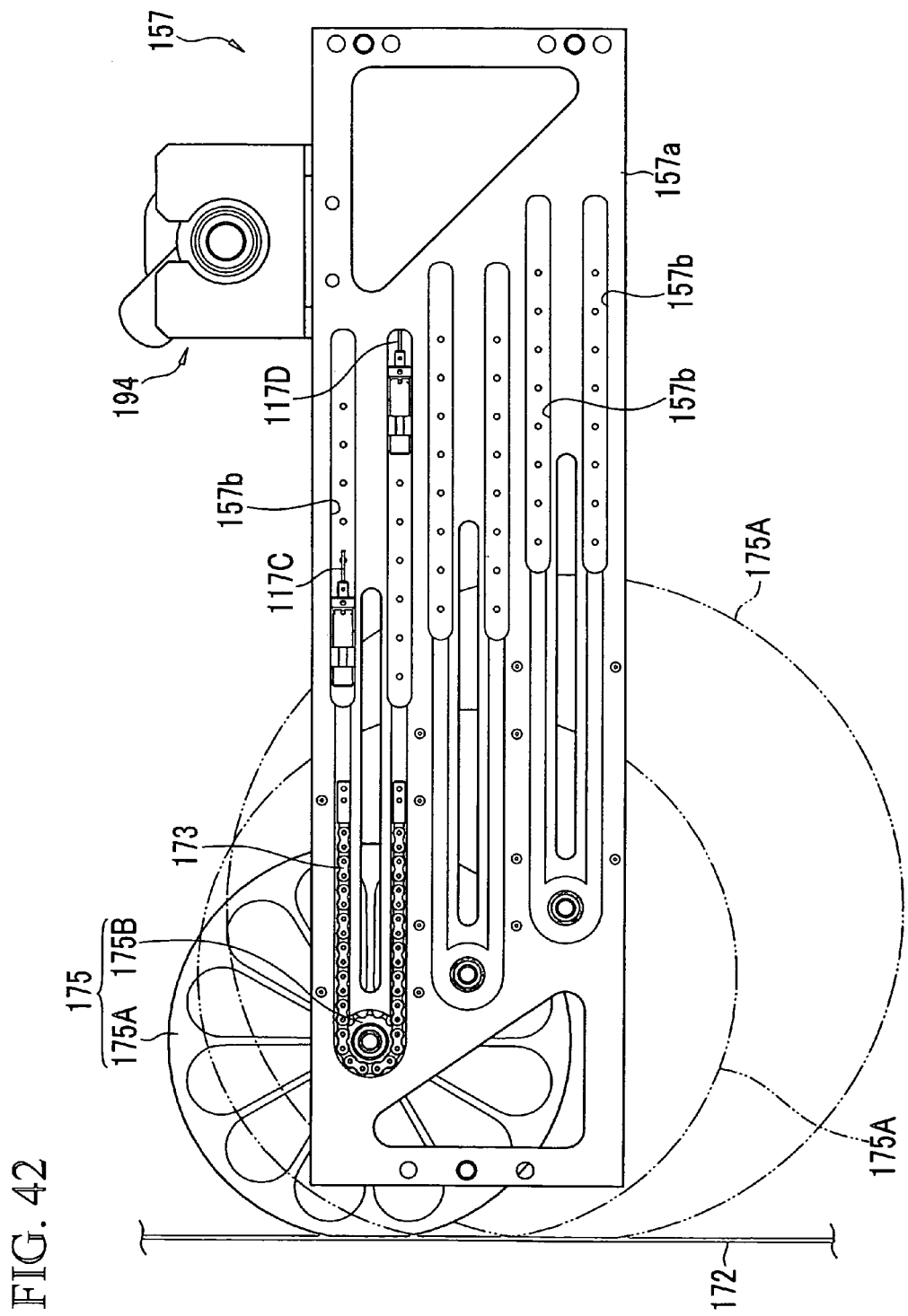
FIG. 42 is a view showing the essential part of the horizontal bending operating part.

Each end of the second belt member 172 is connected to the second die parts 161b via four adjusting wheels 166. The second chain belt 173 and the second gear 175 are attached to a plate-shaped gear box 157a, as shown in FIG. 42. Large diameter parts 175A of the second gear 175 which are connected to the second belt member 172 are attached on one surface side of the gear box 157a, and small diameter parts 175B, which have the same axes as the large diameter parts 175A, are disposed inside grooves 157b that are formed in the other surface side of the gear box 157a. The second belt member 172 is fixed in place at the outer peripheral surface of the large diameter parts 175A. When the second movement restricting member 161 moves due to an operational input at the instrument operating parts 131 A and 131 B, the second belt member 172 is pulled in one direction accompanying this, and the large diameter part 175A begins to rotate. The second chain belt 173 that is housed inside the grooves 157b engages with the small diameter parts 175B. The bending wires 117C and 117D which extend from the first sheath 203 are each connected to an end of the second chain belt 173. Furthermore, three sets of grooves 157b are prepared in the gear box 157a. By pairing these with the different diameter large diameter parts 175A, it is possible to select a reduction gear ratio at the horizontal bending operating part 157.

The rotation operating part 150 is disposed further toward the front end side than the first arm clamp 152A and the second arm clamp 152B of the fixed frame 145B, and is provided with a sheath connector 181, which has a rotation knob and to which the base end of the first sheath 203 is connected; and a rotation support 182 for supporting the sheath connector 181 in a manner to enable rotation. Through-holes 183 are disposed in the rotation support 182 through which the first arm member 208A and the second arm member 208B, which are respectively connected to the first arm clamp 152A and the second arm clamp 152B, the video cable 220, and the like, are inserted.

Figure 37:
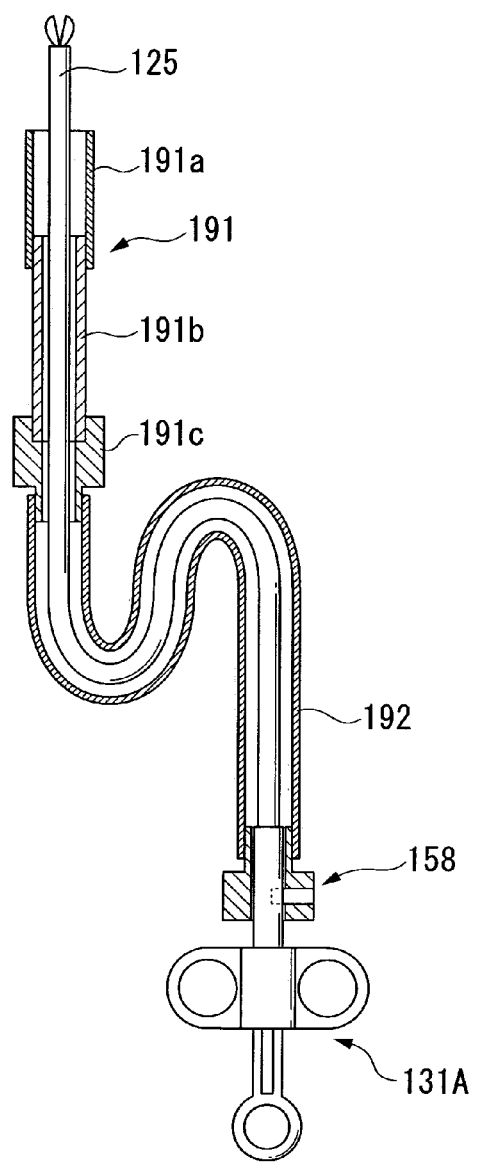
FIG. 37 is a schematic view showing the essential parts of the sheath advance/retract mechanism.

As shown in the schematic cross-sectional view in FIG. 37, the sheath advance/retract part 191, which is connected to the first arm clamp 152A, is provided with a first tubular member 191a, a second tubular member 191b which is disposed nested inside the first tubular member 191a, and a die part 191c that supports the base end of the second tubular member 191b. An instrument sheath 192 is installed between the die part 191c on the base end side and the attachment part 158, this instrument sheath 192 connecting an opening of the die part 191c and an opening of the tubular member 193 of the attachment part 158. The instrument insertion part 125 having a coil sheath that is connected to gripping forceps or the like at the front end is inserted into the sheath advance/retract part 191 and the instrument sheath 192. Of the two tubular members 191a and 191b that are disposed in nesting form, the first tubular member 191a is supported by the first arm clamp 152A and is fixed in place to the fixed frame 145B, while the second tubular member 191b is connected to the die part 191c and is fixed in place to the moving frame 145A. Accordingly by advancing and retracting the moving frame 145A with respect to the fixed frame 145B, it is possible to advance and retract the second tubular member 191b with respect to the first tubular member 191a, and thereby advance and retract the instrument insertion part 125 which is inserted inside the second tubular member 191b with respect to the first sheath 203. As a result, the high-frequency scalpel 205A that is disposed at the front end of the first arm member 208A can be made to project out from the front end of the front end part 215A, and to be retracted back from this projecting position.

Figure 38:
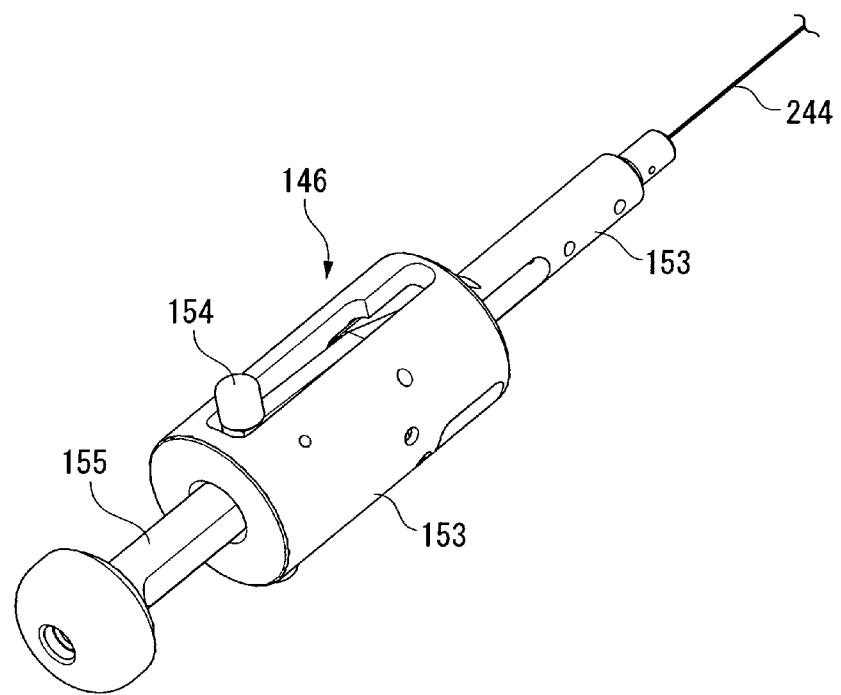
FIG. 38 is a perspective view showing the open/close operating part.
Figure 39:
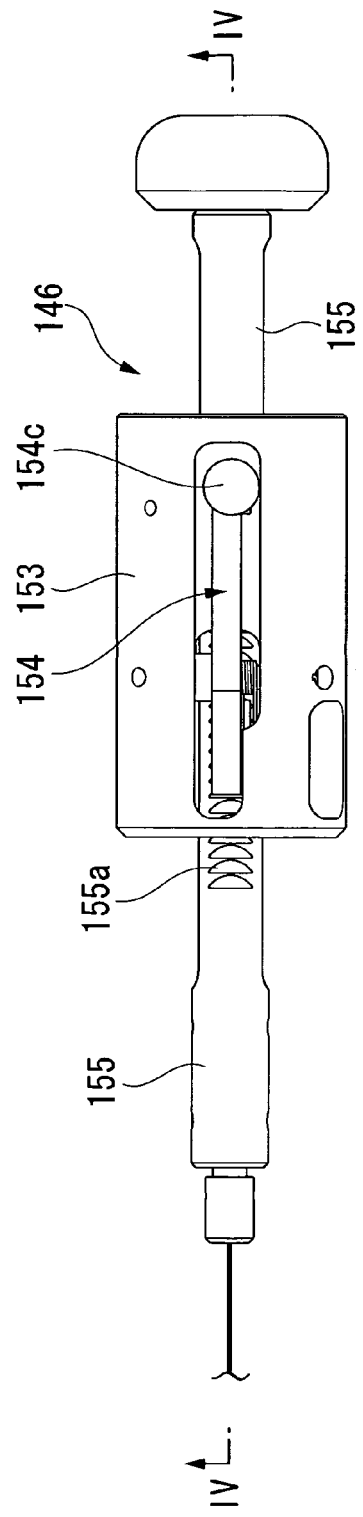
FIG. 39 is a side view showing the open/close operating part.
Figure 40:
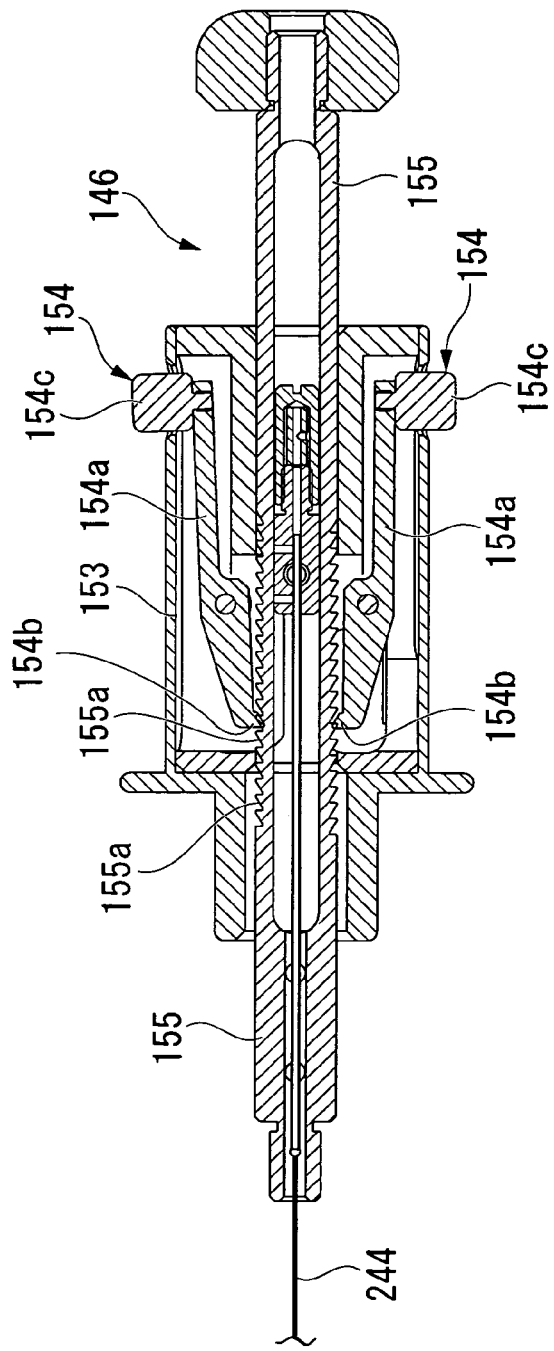
FIG. 40 is a cross-sectional view along line IV-IV in FIG. 39.

The open/close operating part 146 is attached to the frame member 170 of the fixed frame 145B. As shown in FIGS. 38 through 40, the open/close operating part 146 is provided with an open/close operating part main body 153; an open/close handle 155 to which the base end of the bending opening/closing wire 244 is connected and which can advance and retract with respect to the open/close operating part main body 153; and a gear 154 for restricting the position of the open/close handle 155 with respect to the open/close operating part main body 153. A rack 155a is formed at the open/close handle 155 for restricting movement toward the front end side when the open/close handle 155 is pulled toward the hand-held side. This rack 155a is for restricting the advance of the open/close handle 155 with respect to the open/close operating part main body 153 through engagement with a claw 154b of a gear 154 that is provided inside the open/close operating part main body 153. In this restricted state, the claw 154b of the above-mentioned gear 154 can be moved away and released from the rack 155a by pressing a release button 154c that is provided opposite the claw 154b via a gear main body 154a of the gear 154. When a starting state for the open/close mechanism 210 is defined as the state in which the first arm member 208A and the second arm member 208B are closed at a position along the direction of the central axis C1 of the first sheath 203, then, in this starting state, the open/close handle 155 is set so as to be positioned toward the front end of the open/close operating part main body 153.

The sheath operating part 194 is disposed vertically positioned to a stand part 194A that is attached to the gear box 157a of the fixed frame 145B. The sheath operating part 194 can be freely attached to or released from the stand part 194A. The sheath operating part 194 is provided with a bending knob 195 for bending operation of the bending part 203B provided at the front end side of the first sheath 203. The operating sheath 204 which extends from the first sheath 203 is connected to a front end part 194a of the sheath operating part 194. Four bending wires 201B, which are inserted into each of the joint wheels 201 of the bending part 203B are inserted into the operating sheath 204. As in the case of the typical medical treatment endoscope, the four bending wires 201B can be advanced or retracted by turning the bending knob 195 that is provided at the sheath operating part 194, enabling bending operation of the bending part 203B to be carried out by the aforementioned advance/retract operation.

Next, the operation of the embodiment of the present invention will be explained.

Figure 26:
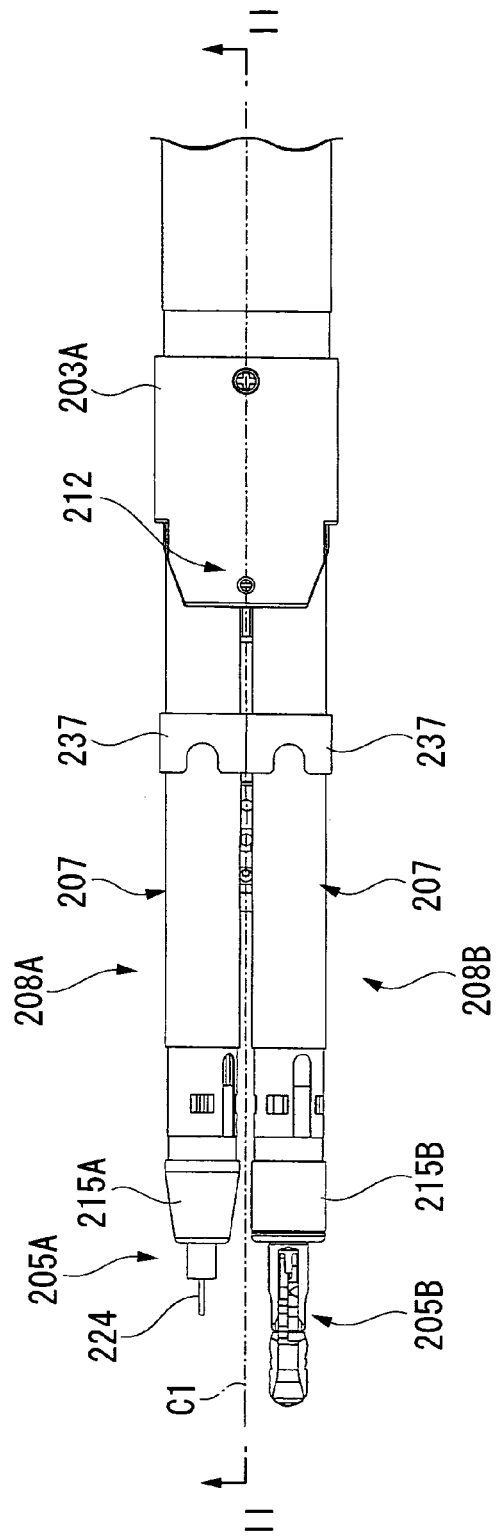
FIG. 26 is a plan view of the front end of the medical treatment endoscope showing the case where the arm member is closed.
Figure 27:
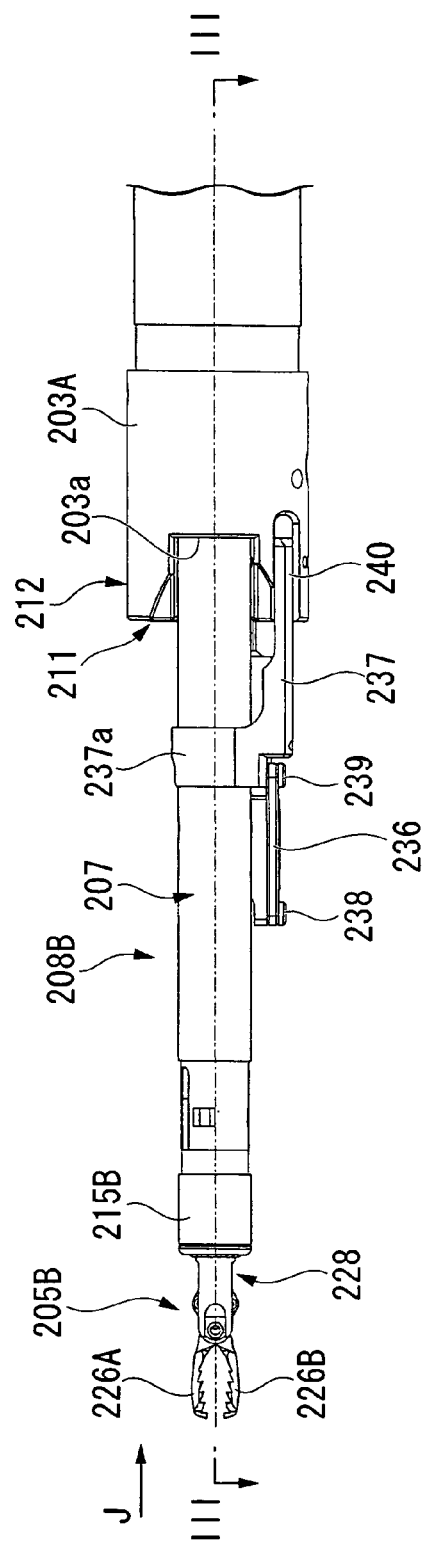
FIG. 27 is a side view of the front end of the medical treatment endoscope showing the case where the arm member is closed.
Figure 28:
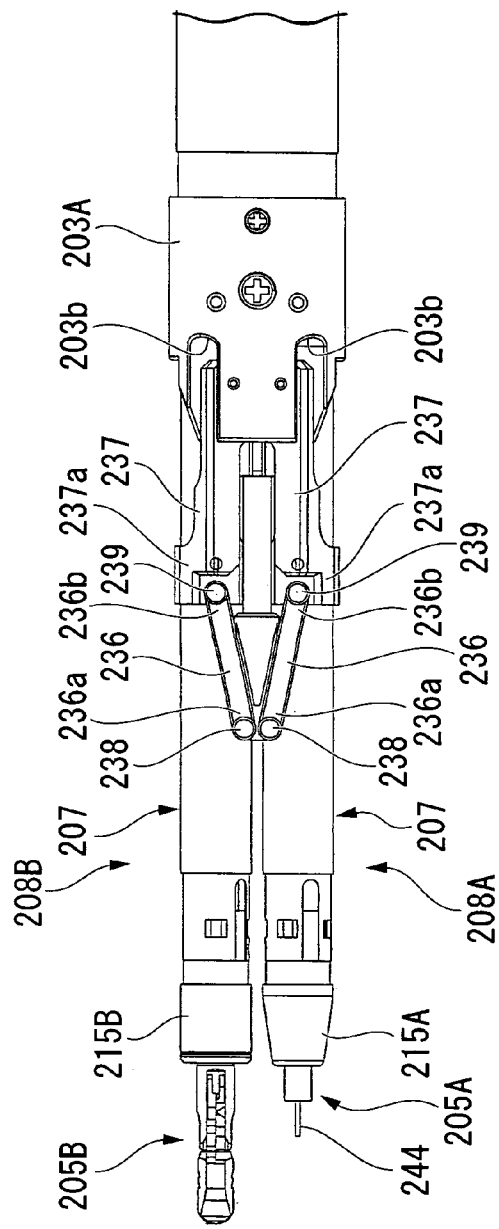
FIG. 28 is an underside view of the front end of the medical treatment endoscope showing the case where the arm member is closed.
Figure 29:
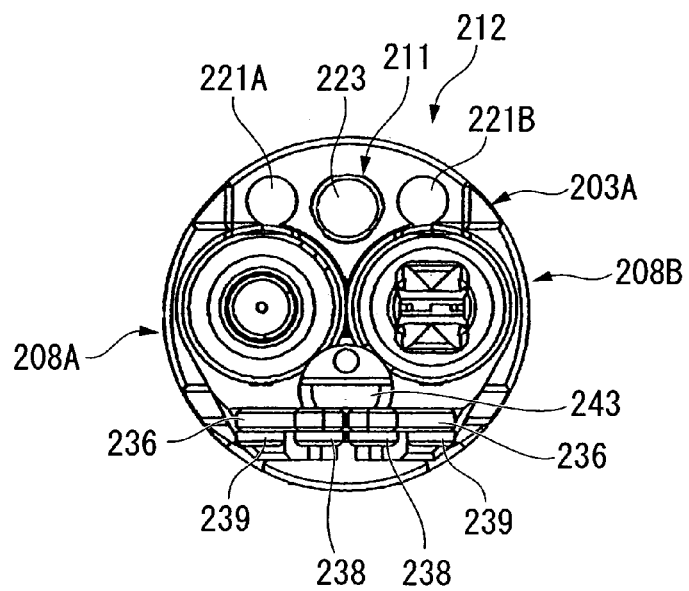
FIG. 29 is a view along direction J in FIG. 27.

When opening the first arm member 208A and the second arm member 208B with respect to the first sheath 203 from the starting state shown in FIGS. 26 and 27, the open/close handle 155 is slid with respect to the open/close operating part main body 153 a predetermined distance toward the hand-held side. At this time, the bending opening/closing wire 244 is thus retracted with respect to the sheath front end part 203A toward the hand-held side, and the open/close operating part 243 is retracted. Accompanying this, the linking part 236 receives a rotational torque directed away from the central axis of the first sheath 203, and, as a result, the other end 236b of the linking part 236 is rotated by a specific angle in the direction away from the central axis C1 of the first sheath 203, with the one end 236a of the linking part 236 serving as the rotational center. As shown in FIGS. 23 through 25, the support 237 rotates with respect to the first sheath 203. In this state, the position of the open/close handle 155 is fixed in place by the rack 155a of the open/close operating part 146, and the position of the bending opening/closing wire 244 is thus fixed in place with respect to the first sheath 203.

In contrast, when closing the first arm member 208A and the second arm member 208B with respect to the front end side of the first sheath 203, the open/close handle 155 is advanced forward with respect to the open/close operating part main body 153, while pressing on the release button 154c. At this time, the bending opening/closing wire 244 is advanced forward with respect to the front end side of the first sheath 203. Accompanying this, the rotational torque applied on the linking part 236 is released, and the other end 236b of the linking part 236 is rotated in a direction toward the central axis C1 of the first sheath 203, employing the one end 236a of the linking part 236 as the rotational center. As a result, the support 237 rotates with respect to the first sheath 203 and the first arm member 208A and the second arm member 208B close, i.e., resumes the starting state.

In the case where the high frequency scalpel 205A projecting out from the front end of the first arm member 208A is to be projected out still further from the front end of the first arm member 208A, this is accomplished by advancing the moving frame 145A of the operating part 151 with respect to the fixed frame 145B. At this time, the entirety of the moving frame 145A moves in the direction that brings it closer to the first arm clamp 152A, and the members positioned in hand-held side from the second tubular member 191b of the sheath advance/retract part 191 which is supporting the instrument insertion part 125, move in a direction that brings it closer to the first tubular member 191a, and the instrument insertion part 125 is advanced inside the first sheath 203. In this case, the first arm member 208A is fixed in place to the first arm clamp 152A, so that only the high frequency scalpel 205A is projected further out from the front end part 215A of the first arm member 208A. Furthermore, since the bending wires 117A, 117B, 117C, and 117D are separated from the instrument insertion part 125 at the first arm clamp 152A, the bending state of the bending part 207 is not altered by the operation to advance the moving frame 145A.

In contrast, when moving the high frequency scalpel 205A toward the hand-held side of the first arm member 208A, the moving frame 145A of the operating part 151 is retracted with respect to the fixed frame 145B. At this time, the members positioned at the hand-held side from the second tubular member 191b of the sheath advance/retract part 191 which is supporting the instrument insertion part 125, are retracted with respect to the first tubular member 191a. In this way, the high frequency scalpel 205A is again disposed at its starting state position.

When bending the first arm member 208A and the second arm member 208B in the vertical direction, the vertical bending operating part 156 is manipulated. In other words, the instrument operating parts 131A and 131B which are attached to the attachment parts 158 are gripped and moved in the vertical direction. In this case, the attachment part 158 moves vertically with the limits of the second movement restricting member 161, while at the same time, the first movement restricting member 160 moves together with the attachment part 158 along the first bending guides 196 in the vertical direction. Here, the first die parts 160b of the first movement restricting member 160 also move in the vertical direction, so that the first belt member 165 moves accompanying this, and the first gear 168 is rotated in either direction. At this time, the first chain belt 167 is rotated in either direction, and, accompanying this, one of the bending wires 117A and 117B is advanced with respect to the first sheath 203, while the other is retracted. In this way, the joint wheels 216 of the bending part 207 are inclined accompanying the movement of the bending wires 117A and 117B, and bend vertically.

In contrast, when bending the first arm member 208A and the second arm member 208B in the horizontal direction, the horizontal bending operating part 157 is manipulated. In other words, the instrument operating parts 131A and 131B which are attached to the attachment parts 158 are gripped and moved in the horizontal direction. In this case, the attachment part 158 moves horizontally within the limits of the first movement restricting member 160, while at the same time, the second movement restricting member 161 moves together with the attachment part 158 along the paired second bending guides 197 in the horizontal direction. Here, the second die parts 161b of the second movement restricting member 161 also move in the horizontal direction, so that the second belt member 172 moves accompanying this, and the second gear 175 is rotated in either direction. At this time, the second chain belt 173 is rotated in either direction, and, accompanying this, one of the bending wires 117C and 117D is advanced with respect to the first sheath 203, while the other is retracted. In this way, the joint wheels 216 of the bending part 207 are inclined accompanying the movement of the bending wires 117C and 117D, and bend horizontally.

When rotating the first sheath 203 with respect to the operating 151, the rotation knob provided to the sheath connector 181 of the rotation operating part 150 is gripped and rotated in the desired direction. As a result, the sheath connector 182 rotates relative to the rotation support 181, causing the first sheath 203 to rotate in the desired direction relative to operating part 151.

In this medical treatment endoscope 200, the first arm member 208A and the second arm member 208B that are inserted into the first sheath 203 can be moved away from the central axis C1 of the first sheath 203 using the open/close mechanism 210, and can be further bent at the bending parts 207 of the first arm member 208A and the second arm member 208B. As a result, it is possible to visually confirm the distal ends of the first arm member 208A and the second arm member 208B when a sufficient visual field has been secured for the image pick-up unit 211. As a result, it is possible to reliably and safely carry out the medical procedure. In this case, the axial force generated by advancing or retracting the bending opening/closing wires 244 with respect to the first sheath 203 is converted into the opening/closing forces for the first arm member 208A and the second arm member 208B at the linking part 236 of the open/close mechanism 210. This point is equivalent to that of the first embodiment. However, in this embodiment, the opening/closing operation of the first arm member 208A and the second arm member 208B is carried out smoothly with a smaller operating force, so that the arm members can be opened even wider.

Namely, in the medical treatment endoscope 1 according to the first embodiment, the bending opening/closing wire 35 is connected to the other end 36b of the linking part 36, and the open/close mechanism 10 is operated by advancing and retracting the bending opening/closing wire 35. In this case, as shown in FIG. 8A, the bending opening/closing wire 35 that is connected to the other end 36b of the linking part 36 on the arm member. 8B side has a flexed part 35a that is flexed at a position that is advanced from the sheath front end part 3A. Furthermore, as shown in FIGS. 14 and 15, a flexed part 35a is also provided on the arm member 8A side that flexes at the front end of the guide 41A that houses the bending opening/closing wire 35. For this reason, when opening or closing the arm members 8A and 8B, this flexed part 35a creates sliding resistance, increasing the operating force for bending opening/closing wires 35.

Furthermore, as shown in FIG. 8, the bending opening/closing wire 35 is supported by the flexed part 35a, and has the construction such that the front end side thereof moves along with the opening/closing operation of the arm members 8A and 8B. It is therefore difficult to open the first arm member 8A and the second arm member 8B to an angle greater than 45° with respect to the central axis C1 of the first sheath 3.

Accordingly, in the medical treatment endoscope 200 according to this embodiment, the construction is employed in which the one end 236a of the linking part 236 is connected to the open/close operating part 243 at a position that is further to the front end side of the first arm member 208A and the second arm member 208B than the support part 237, and the pantograph structure that is formed by the two linking parts 236 and the two support parts 237 is altered according to the advance or retraction of the open/close operating part 243. As a result, although a relatively larger operational force is required when initiating the opening operation, the amount of operating force required decreases as the linking part 236 and the support 237 are opened. Therefore, operation of the arm member near the lesion site can be carried out smoothly. Furthermore, since the open/close operating part 243 moves together with the slide member 242 that is disposed at the first sheath 203 side, along the direction of advance and retraction of the bending opening/closing wire 244, there is no change in the direction of operation accompanying the opening/closing operation as in the case of the bending opening/closing wire 35 according to the first embodiment, and the amount of movement of the bending opening/closing wire 242 is communicated without change to the linking part 236. As a result, a more efficient opening/closing movement can be carried out. In this embodiment, opening and closing are carried out by communication of the input on the hand-held side to the pantograph of the open/close mechanism 210 via the bending opening/closing wire 244. However, it is a characteristic of wire driving that the force from pushing the wire is less than the force from pulling the wire. For this reason, the present embodiment is constructed so that operation can be carried out by pulling the bending opening/closing wire 244 when opening the arm members 208A and 208B from a closed state, which requires a relatively large force. Conversely, the present embodiment is constructed so as to employ an arrangement in which the power factor of the pantograph is beneficial when closing arm members that are open, so that only a small force need be communicated from the bending opening/closing wire 244.

Moreover, the more that the bending opening/closing wire 244 is retracted, the further apart the first arm member 208A and the second arm member 208B are spread, such that the first arm member 208A and the second arm member 208B can be spread apart without limit within the parameters of allowable movement of the pantograph. For this reason, the first arm member 208A and the second arm member 208B can be widely spread apart to a position in which the angle exceeds 45° with respect to the central axis C1. As a result, it is possible to prevent the field of view from becoming narrower due to entrance of the first arm member 208A and the second arm member 208B into the field of view of the image pick-up unit 211. In this embodiment, the opening/closing angle of the first arm member 208A and the second arm member 208B is adjusted according to the length of the linking part 236 and the support 237 so that the front end part of the arm member 208A and the front end part of the second arm member 208B form an angle of 50° or greater at the instrument which is 50 to 70 mm distal from the objective lens 223 of the image pick-up unit 211. The angle of opening of the first arm member 208A and the second arm member 208B can be easily adjusted by suitably changing the length of the linking part 236, thereby offering superior freedom of construction.

Furthermore, in this embodiment, openings 203a are provided at the sheath front end part 203A, enabling the bending parts 207 to be advanced outward via these openings 203a. By providing this type of construction, the first arm member 208A and the second arm member 208B can open beyond the objective lens 223 at the base end side of the first sheath 203. As a result, the arm members 208A and 208B are less apt to enter into the field of view of the image pick-up unit 211, making it even easier to see the instrument.

In addition, the open/close operating part 243 and the linking part 236 are disposed to the first arm member 208A and the second arm member 208B on the side of the arm members that is opposite the image pick-up unit 211. As a result, it is possible to prevent the open/close operating part 243 from entering into the field of view of the image pick-up unit 211. Furthermore, since the open/close operating part 243 is pulled toward the hand-held side when opening the first arm member 208A and the second arm member 208B, on this point as well, the construction limits interference with the field of view. In addition, the slide member 242, which restricts the open/close operating part 243 so that it moves only in the direction of the central axis C1 of the first sheath 203, is disposed at the clearance that is formed at the center of the first sheath 203 as a result of disposing the first arm member 208A and the second arm member 208B, which are roughly round in cross-section, adjacent to one another. Accordingly, the construction provides an open/close mechanism 210, while at the same time conserving space inside the first sheath 203.

Furthermore, in the preceding first embodiment, the more that the first arm member 8A and the second arm member 8B are opened, the smaller the angle becomes at flexed part 35a of the bending opening/closing wire 35 and the greater the force required for operation becomes. Moreover, a large force is also required to hold the arms in the open state. In particular, when a force is continuously applied to hold the arms in the open state, there is a chance that the member near the flexed part 35a or the linking part 36 could break. In contrast, in this embodiment, the force required for operation when the first arm member 208A and the second arm member 208B are in the open state is small, and the force for holding the arms in the open state is little. Furthermore, when a plate-shaped member is employed for the linking part 236, the rigidity is increased. For this reason, it is possible to avoid the application of a force on the open/close mechanism 210 when the first arm member 208A and the second arm member 208B are in the open state, so that damage to the linking part 236, etc. is unlikely to occur, and reliability can be improved.

In this embodiment, the bending opening/closing wire 244 is pulled toward the hand-held side when opening the first arm member 208A and the second arm member 208B. Thus, it is possible to adjust the force that is communicated to the bending parts 207, so that the opening angle of the first sheath 203 with respect to the central axis C1 can be finely adjusted. Furthermore, by pulling the open/close handle 155 at once with respect to the open/close operating part main body 153 toward the hand-held side until it comes into contact with a contact point, so that the opening angle between the first arm member 208A and the second arm member 208B with respect to the central axis C1 is set suitable, it is possible to obtain a simplified open/close operation of the first arm member 208A and the second arm member 208B.

Furthermore, the first embodiment had the construction that did not permit changing the rotation or inclination of the front end part. Moreover, by using the medical treatment endoscope according to the first embodiment, there are unreachable points for the instrument since the bending radius of the first sheath 3 is large, resulting from a tube made of a styrene-derived elastomer being employed as the first sheath 3. In this embodiment, a bending part 203B is provided at the front end side of the first sheath 203 that connects the multiple joint wheels 201. By providing the bending part 203B, the bending radius at the front end part becomes smaller, and it is possible to freely direct the sheath front end part 203A in an optional direction. As a result, the approach of the instrument is facilitated and the procedure can be carried out smoothly.

Furthermore, the first arm member 208A and the second arm member 208B are constructed so as not to advance or retract with respect to the sheath front end part 203A due to the supports 237. Therefore, only the high frequency scalpel 205A or other such instrument projecting out from the front end part 215A of the first arm member 208A advances or retracts with respect to the first arm member 208A. In the first embodiment, the state in which the instrument is directed along the central axis of the first sheath 203 is designated as the starting state, regardless of the open/close status of the first arm member 8A and second arm member 8B. Furthermore, based on the idea of being able to move the instrument forward/backward, up/down or left/right from the starting state, the construction was provided to enable the first arm member 8A, which is provided with a bending part 7, to advance and retract with respect to the first sheath 3. However, defining the state in which the first arm member 208A and the second arm member 208B are opened by the open/close mechanism 210, and the instrument at the front end is directed inward so that the front end and the affected part come into the field of view of the image pick-up unit 211, to be the starting state of the first arm member 208A and the second arm member 208B is natural. In this starting state, the construction is employed in which only the instrument projecting out from the front end part 215A, and not the first arm member 208A, is advanced and retracted, so as to enable advance and retract of the instrument with respect to the affected part.

Next, the bending operation of the first arm member 208A and the second arm member 208B via operation of the instrument operating parts 131A and 131B can be carried out with an even smaller amount of force at the operating part 151 of the medical treatment endoscope 200 according to this embodiment.

In the preceding first embodiment, the attachment part 58 is supported in a manner to enable relatively free movement within the frames of the rectangular, plate-shaped first movement restricting member 60 and the second movement restricting member 61. The construction is provided in which the operational input to the forceps operating part 31 that is attached to the attachment part 58 is communicated via the first movement restricting member 60 and the second movement restricting member 61 to the first belt member 65, which is connected to the end part of the first movement restricting member 60, and the second belt member 72, which is connected to the end part of the second movement restricting member 61. In this construction, in the case of an operational input to grip the forceps operating part main body 32 and move it vertically or horizontally, when the forceps operating part main body 32 is inclined in the direction of input of the operation, with the attachment part 58 employed as a fulcrum, then the attachment part 58 is pressed against the first movement restricting member 60 and the second movement restricting member 61, leading to resistance. As a result, there is an undesirable increase in the force required for operation.

In addition, the first belt member 65 and the second belt member 72 are connected to the one end 60a of the first movement restricting member 60 and the one end 61a of the second movement restricting member 61, respectively. For this reason, the force for moving the first belt member 65 and the second belt member 72 becomes focused at the end part of the first movement restricting member 60 and the second movement restricting member 61. A movement is generated as a result, leading to resistance in the movement. As a result, there is an undesirable increase in the force required for operation.

Accordingly, in this embodiment, the construction is provided in which the first movement restricting member 160 and the second movement restricting member 161 are composed of the slide rails 160a and 161a, respectively, and the slide blocks 158A and 158B of the attachment part 158 engage with these respective slide rails 160a and 161a to permit sliding. According to this construction, when there is an operational input to the instrument operating parts 131A and 131B, the attachment part 158 can be smoothly displaced with a light amount of operating force, without inclining resulting from the employment of the attachment part 158 as a fulcrum. Furthermore, the first belt member 165 is connected to the first die parts 160b that are provided at the longitudinal center of the slide rails 160a. The first movement restricting member 160 is disposed on the frame member 170 via the first bending guide 196, which has the slide rail 196a and the slide block 196b that engages with the slide rail 196a in a manner to enable sliding. According to this construction, it is possible to reduce generation of a movement during the communication of the operational input from the first movement restricting member 160 to the first belt member 165 regardless of the position of the attachment part 158 on the first movement restricting member 160. This also applies to the connection between the second movement restricting member 161 and the second belt member 172. As a result, it becomes possible to realize an even greater reduction in the amount of operating force required.

Furthermore, by sliding the moving frame 145A with respect to the fixed frame 145B via the slide mechanisms 148 and 190, the instrument insertion part 125, which is inserted into the first arm member 208A, is made to advance and retract with respect to the first arm member 208A and the first sheath 203. As a result, the high frequency scalpel 205A or other such instrument can be made to project out or retract back from the front end part 215A of the first arm member 208A. Accordingly, it is possible to increase the procedure limits for the instrument for the first arm member 208A and the first sheath 203. Furthermore, the construction is provided in which the advance and retraction of the instrument is carried out by varying the length of the instrument insertion part 125 with respect to the first arm member 208A, enabling the advance and retraction of the instrument to be carried out smoothly. This type of construction provides the benefit of enabling the advance/retract mechanism for the instrument to be provided at an optional position. Furthermore, in the operating part 151 in this embodiment, the sheath advance/retract part 191 is provided at the perpendicular part that extends from the first sheath 203 to the bending operating part 147, which is essential basically. As a result, this construction succeeds in shortening the overall length of the operating part 151 while at the same time providing an instrument advance/retract mechanism. Moreover, since the sheath advance/retract part 191 is provided farther toward the first sheath 203 side than the part bending the instrument insertion part 125, the resistance between the instrument sheath 192 and the instrument insertion part 125 which is generated at the bent part of the instrument insertion part 125 is not received during operations to advance and retract the instrument. As a result, the operation of advancing and retracting the instrument can be accomplished with a light force.

Moreover, the first tubular member 191*a* and the second tubular member 191*b* that are disposed in a nesting manner are relatively long, so that it is possible to greatly adjust the length of the instrument insertion part 125. As a result, in addition to being able to increase the advance/retract width of the instrument, the sheath advance/retract part 191 can also be used to absorb differences in the length of the instrument insertion part 125 when exchanging instruments.

Furthermore, the sheath operating part 194 which is provided with a bending knob 195 for operating the bending part 203B can be freely attached to and released from the stand part 194A that is attached to the gear box 157*a* of the fixed frame 145B. According to this construction, when inserting the inserted part of the medical treatment endoscope 200 into a body cavity, the sheath operating part 194 can be operated after being detached from the stand part 194A, thereby improving operability during insertion. The sheath operating part 194 is constructed to attach to the stand part 194A when performing a treatment, to enable fine adjustment of the bending angle of the bending part 203B by rotational operation of the bending knob 195.

In this embodiment as well, the open/close mechanism 210 can be operated by operating the open/close operating part 146 of the operating part 151 to advance and retract the bending opening/closing wires 244 with respect to the first sheath 203. Furthermore, by performing operations in the state of the instrument operating part 131B of the gripping forceps 205B attached to the bending operating part 147, not only can open/close operation of the paired forceps pieces 226A and 226B of the gripping forceps 205B be performed, but it is also possible to carry out bending operation of the bending part 207. Thus, the procedure is facilitated. Moreover, by rotating the instrument operating part 131A with respect to the attachment part 158, the instrument can be rotated to the desired state. Moreover, since the bending part 207 is employed only for bending an instrument such as gripping forceps 205B, greater bending is possible, and a larger force can be output, as compared to conventional endoscopes in which there is a structure that is required to bend a plurality of apparatuses such as instruments, video cable (the image guide in an optical endoscope), light guides and the like.

[Fourth Embodiment]

A fourth embodiment will now be explained with reference to the figures. The medical treatment endoscope according to the present embodiment represents a further improvement over the medical treatment endoscope according to the first embodiment.

Figure 43:
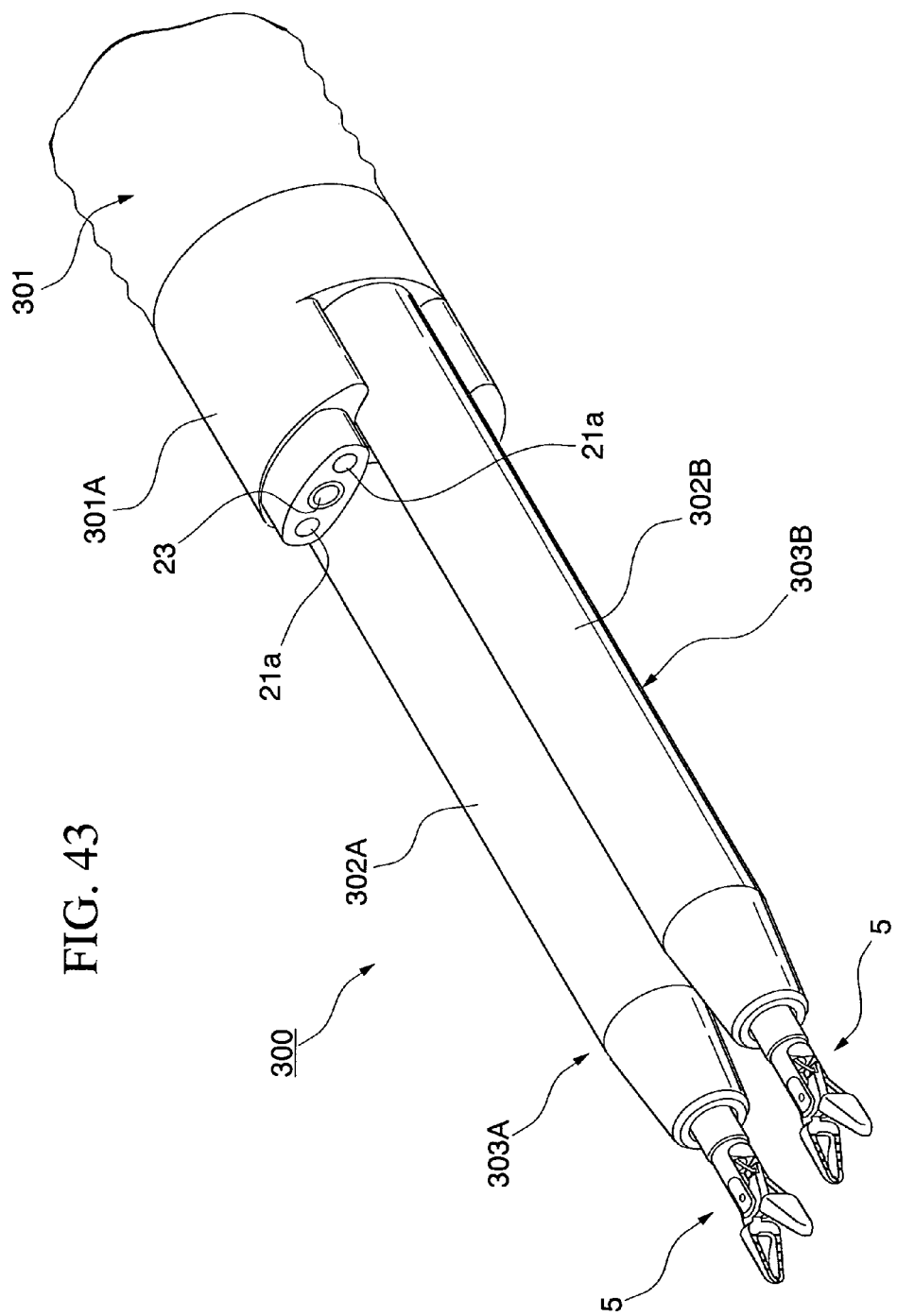
FIG. 43 is a view showing the structure of the tip of the medical treatment endoscope according to a fourth embodiment.
Figure 44:
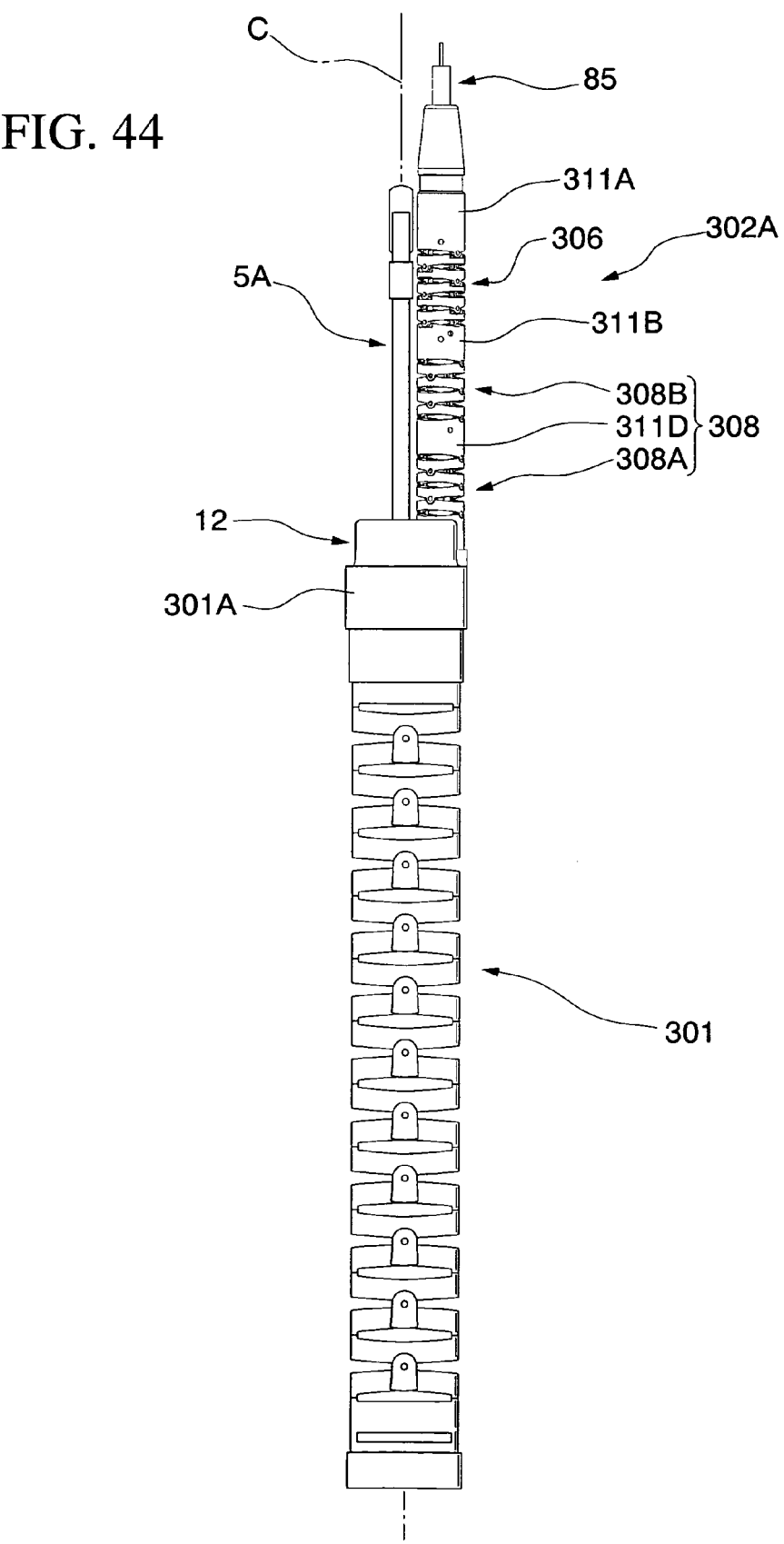
FIG. 44 shows an initial state of an arm member of the medical treatment endoscope in perspective.
Figure 45:
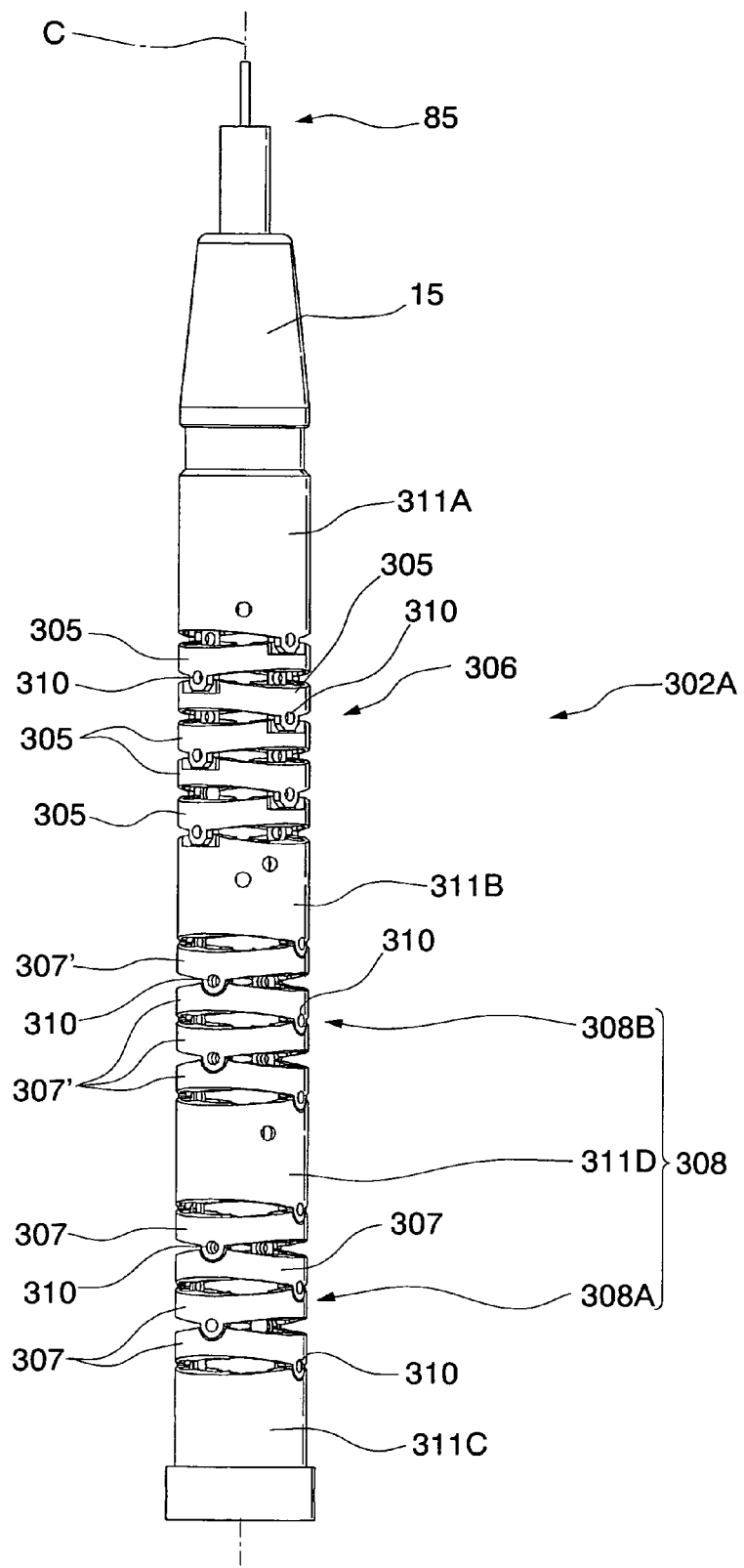
FIG. 45 shows an enlarged initial state of the arm member of the medical treatment endoscope in perspective.
Figure 46:
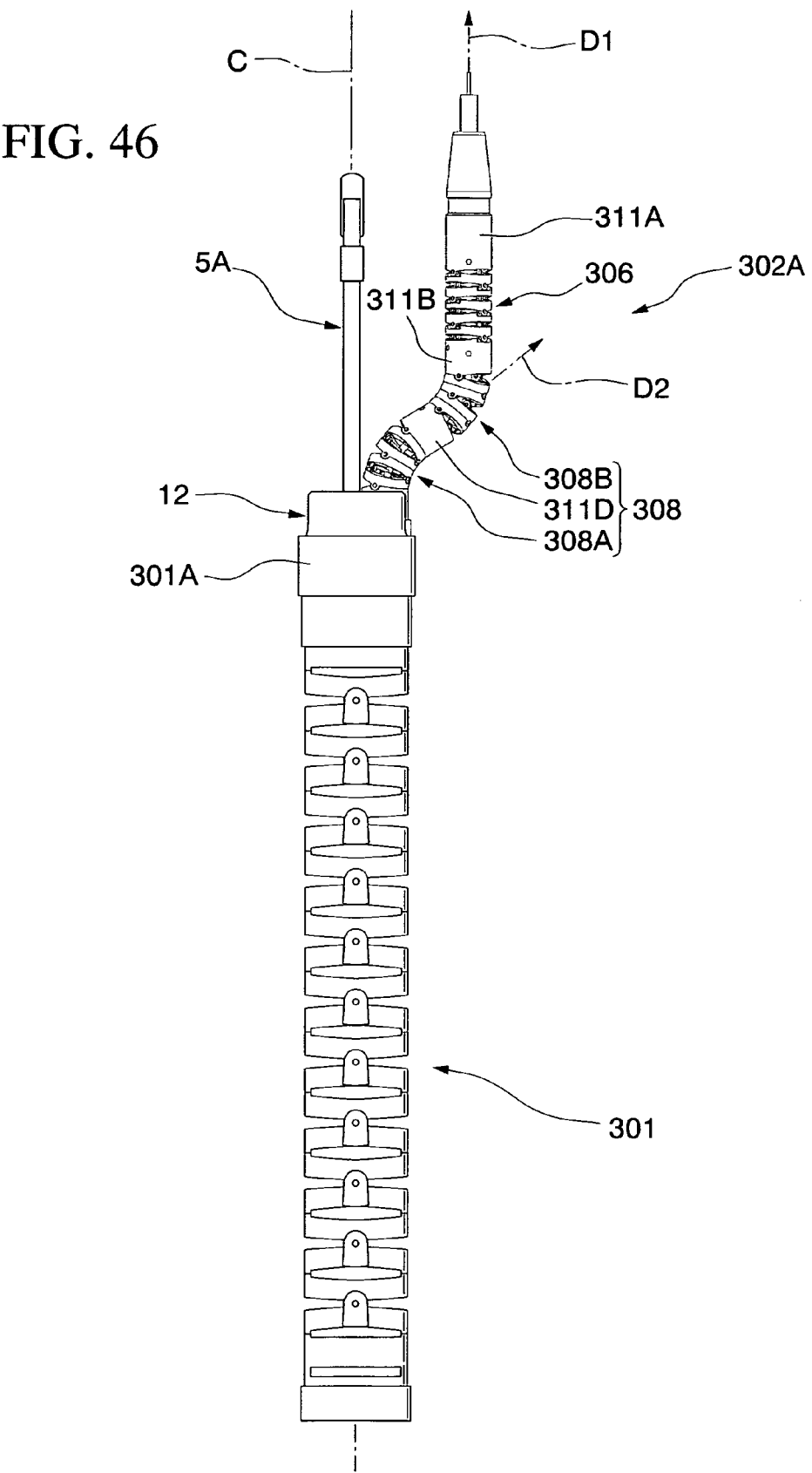
FIG. 46 shows an open state of the arm member of the medical treatment endoscope in perspective.
Figure 47:
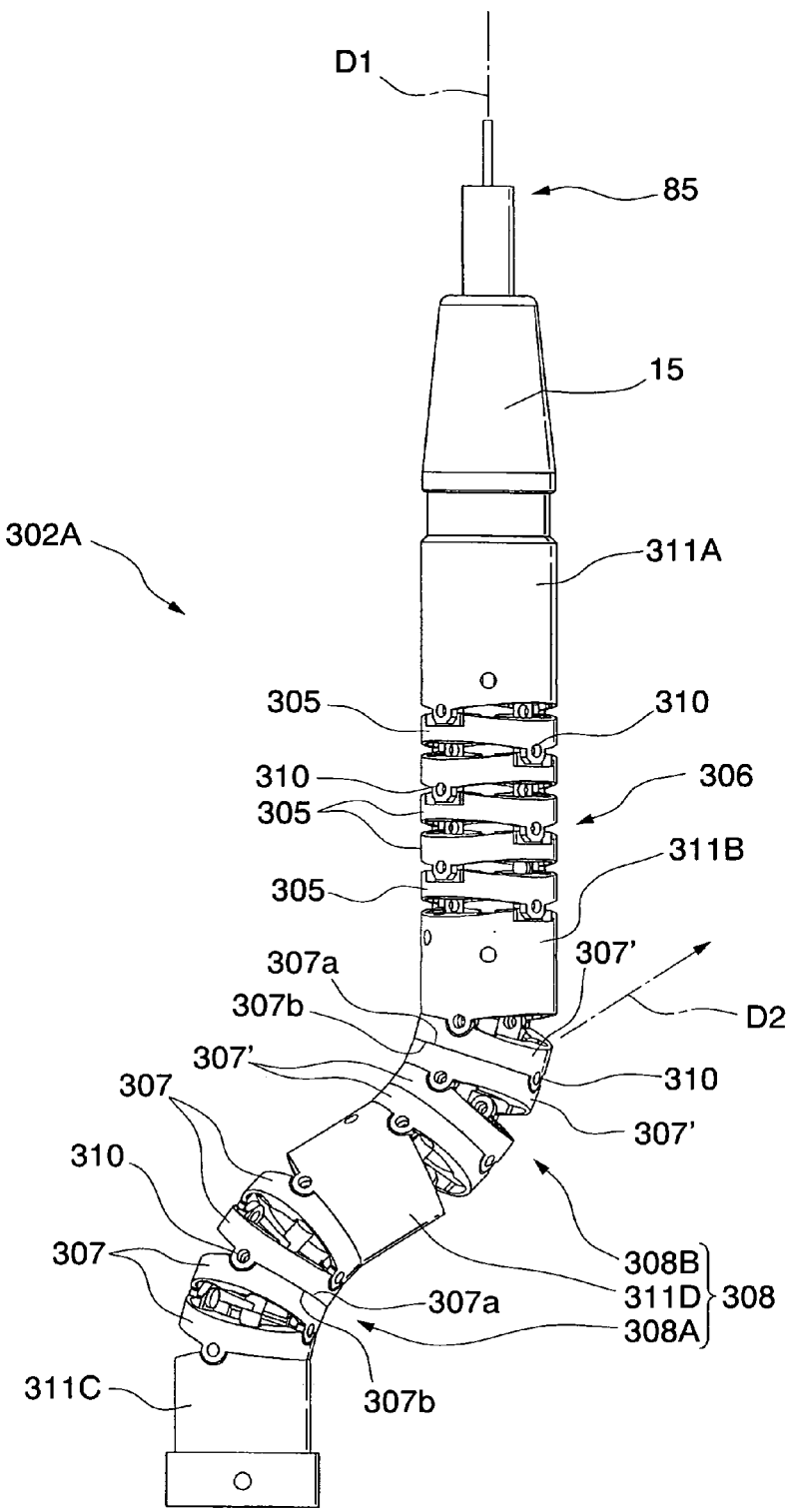
FIG. 47 shows an enlarged open state of the arm member of the medical treatment endoscope in perspective.
Figure 48:
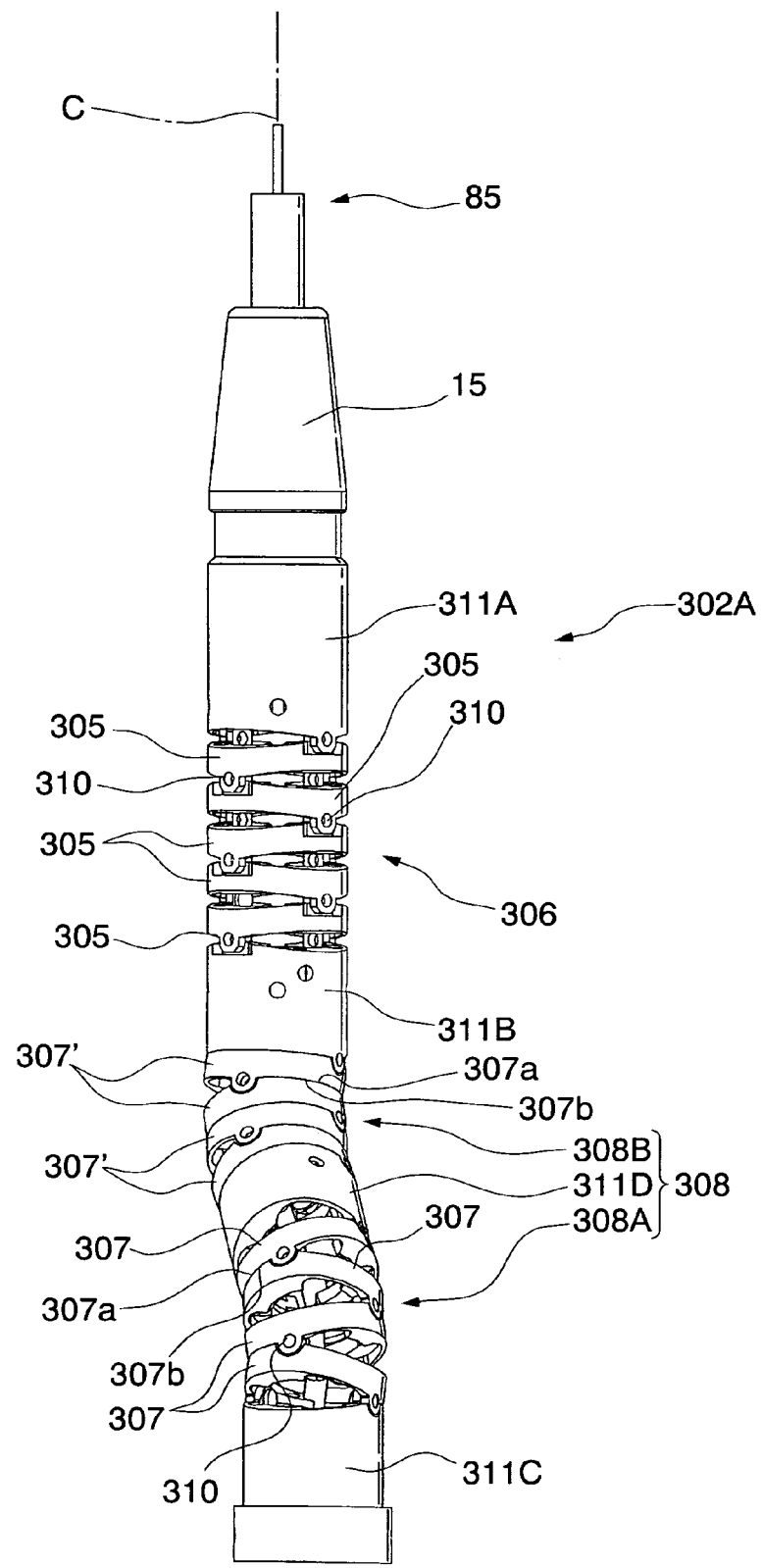
FIG. 48 shows an enlarged open state of the arm member of the medical treatment endoscope in perspective.
Figure 49:
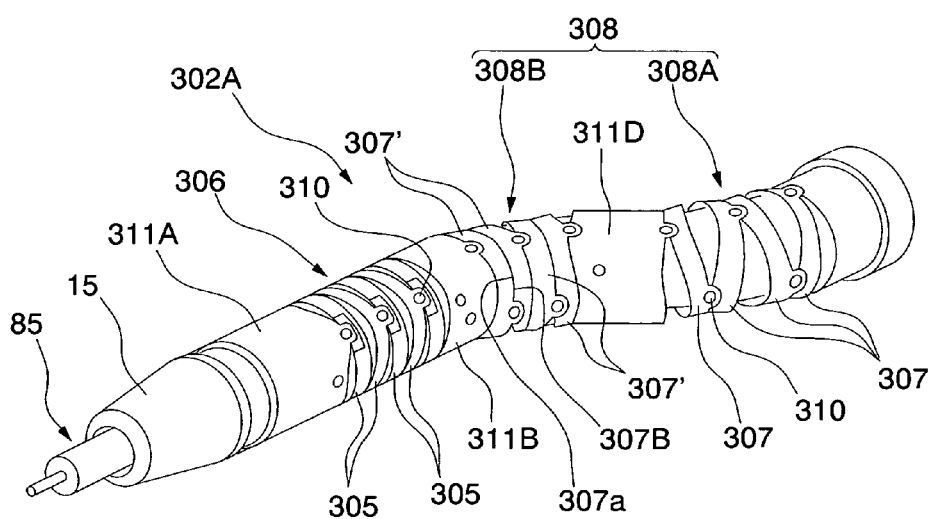
FIG. 49 shows an enlarged open state of the arm member of the medical treatment endoscope in perspective.
Figure 50:
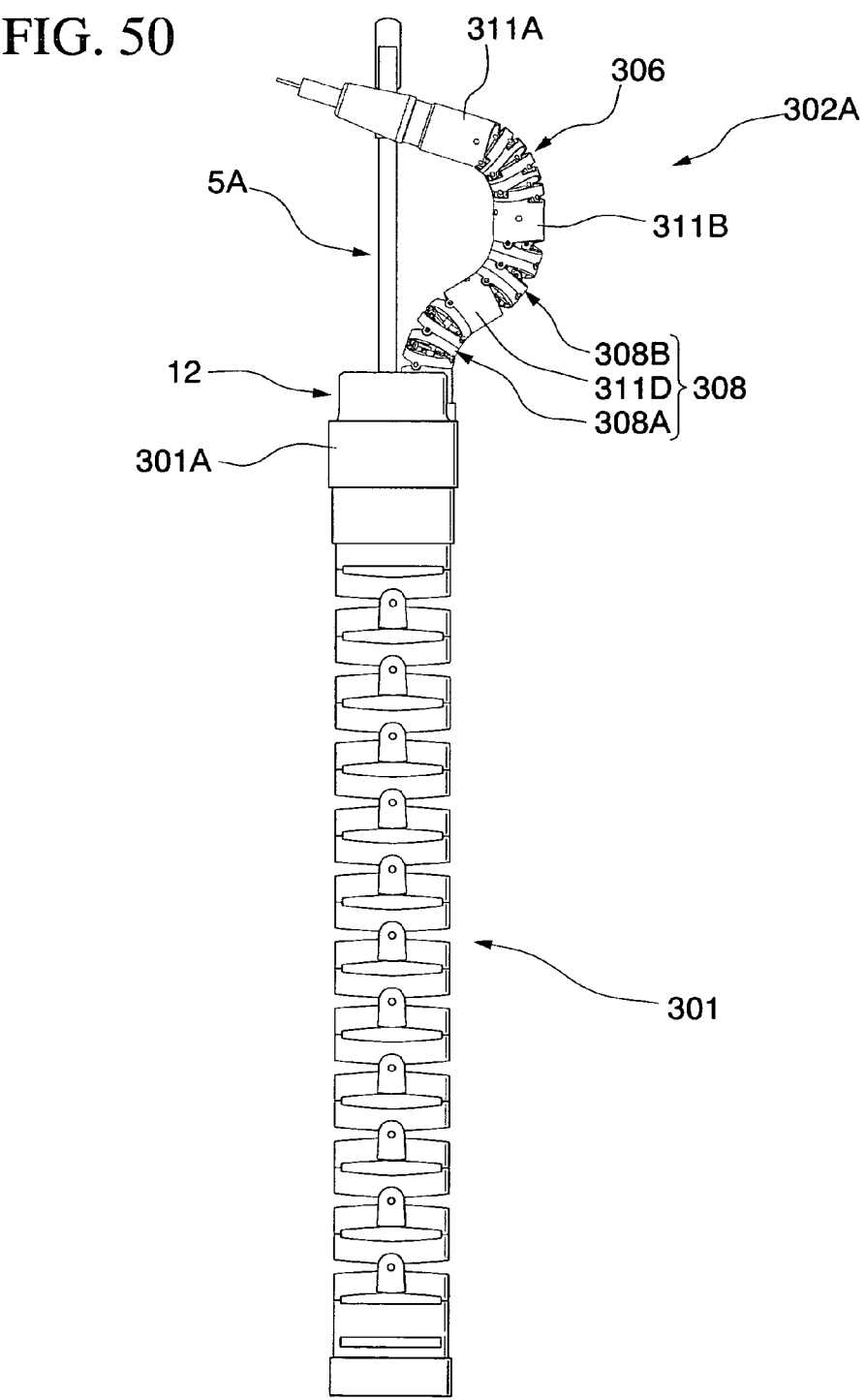
FIG. 50 shows a bending state of the arm member of the medical treatment endoscope in perspective.
Figure 51:
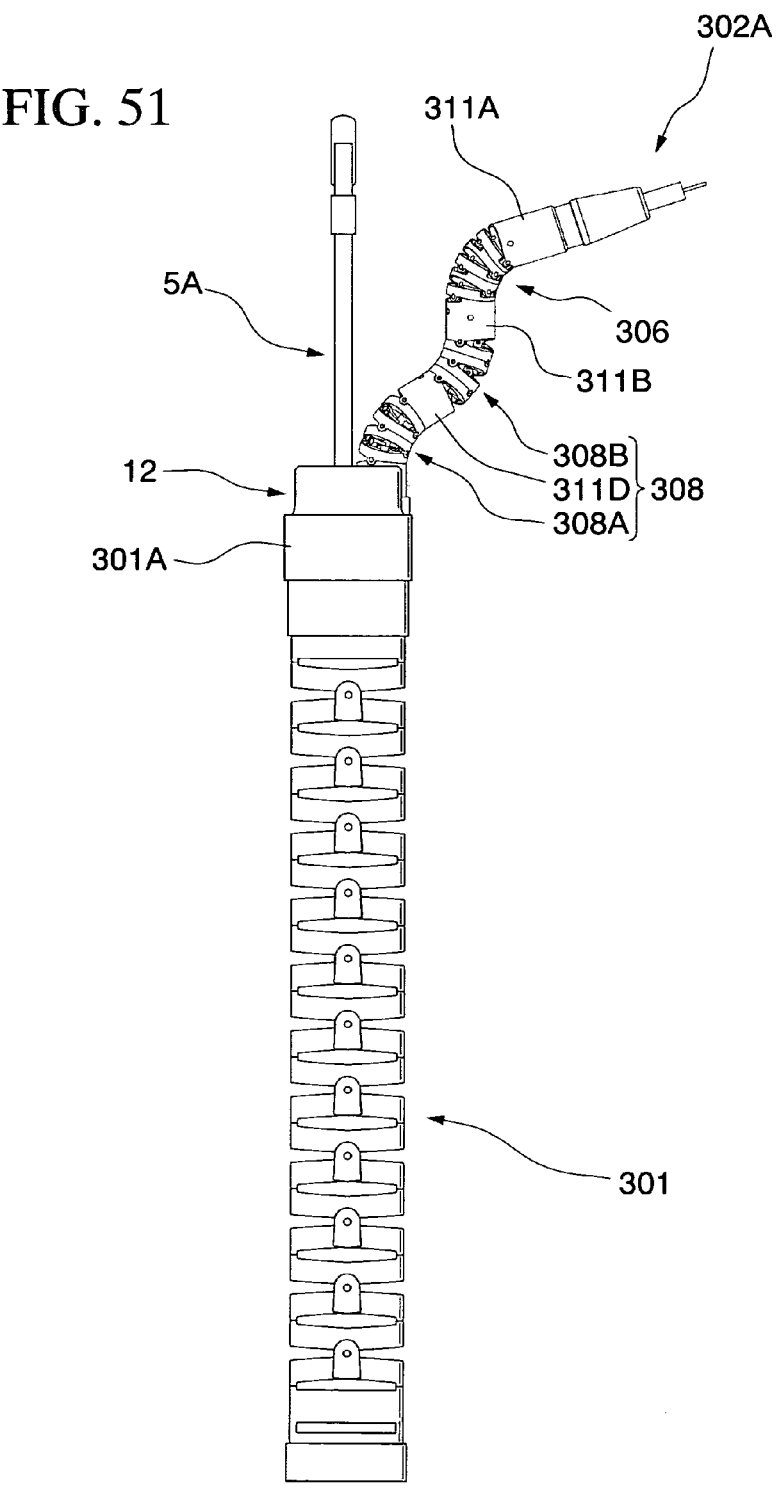
FIG. 51 shows a bending state of the arm member of the medical treatment endoscope in perspective.
Figure 52:
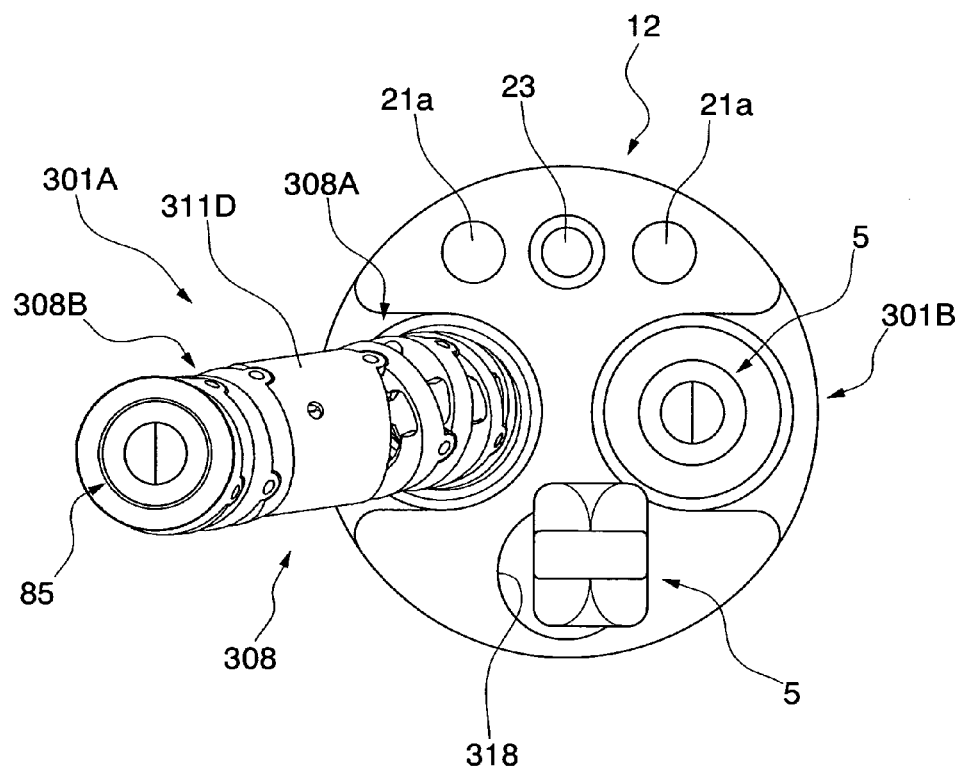
FIG. 52 is a front elevation describing a bending state of the arm member of the medical treatment endoscope in perspective diagram.
Figure 53:
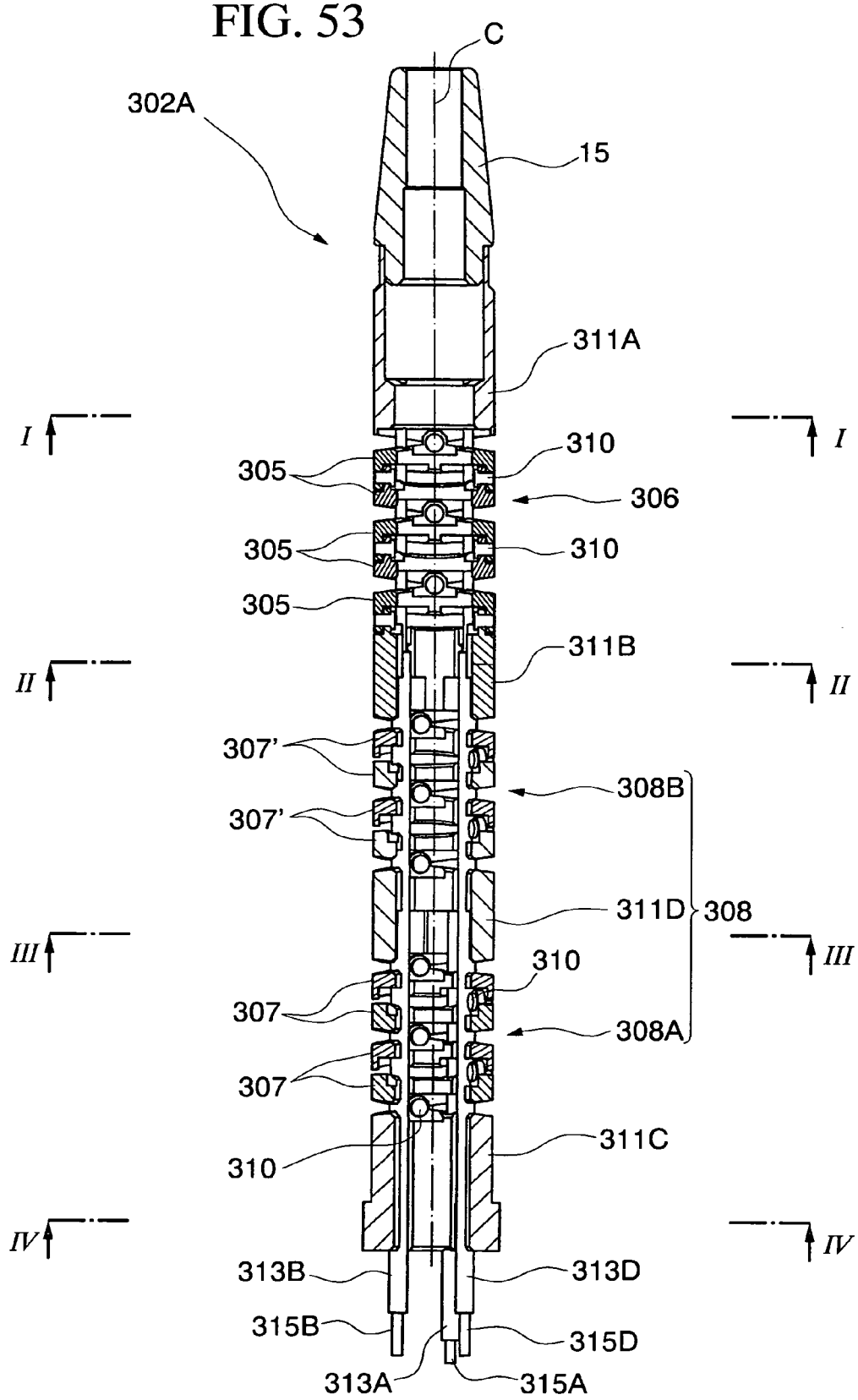
FIG. 53 shows an initial state of the arm member of the medical treatment endoscope in crosssectional view.
Figure 54:
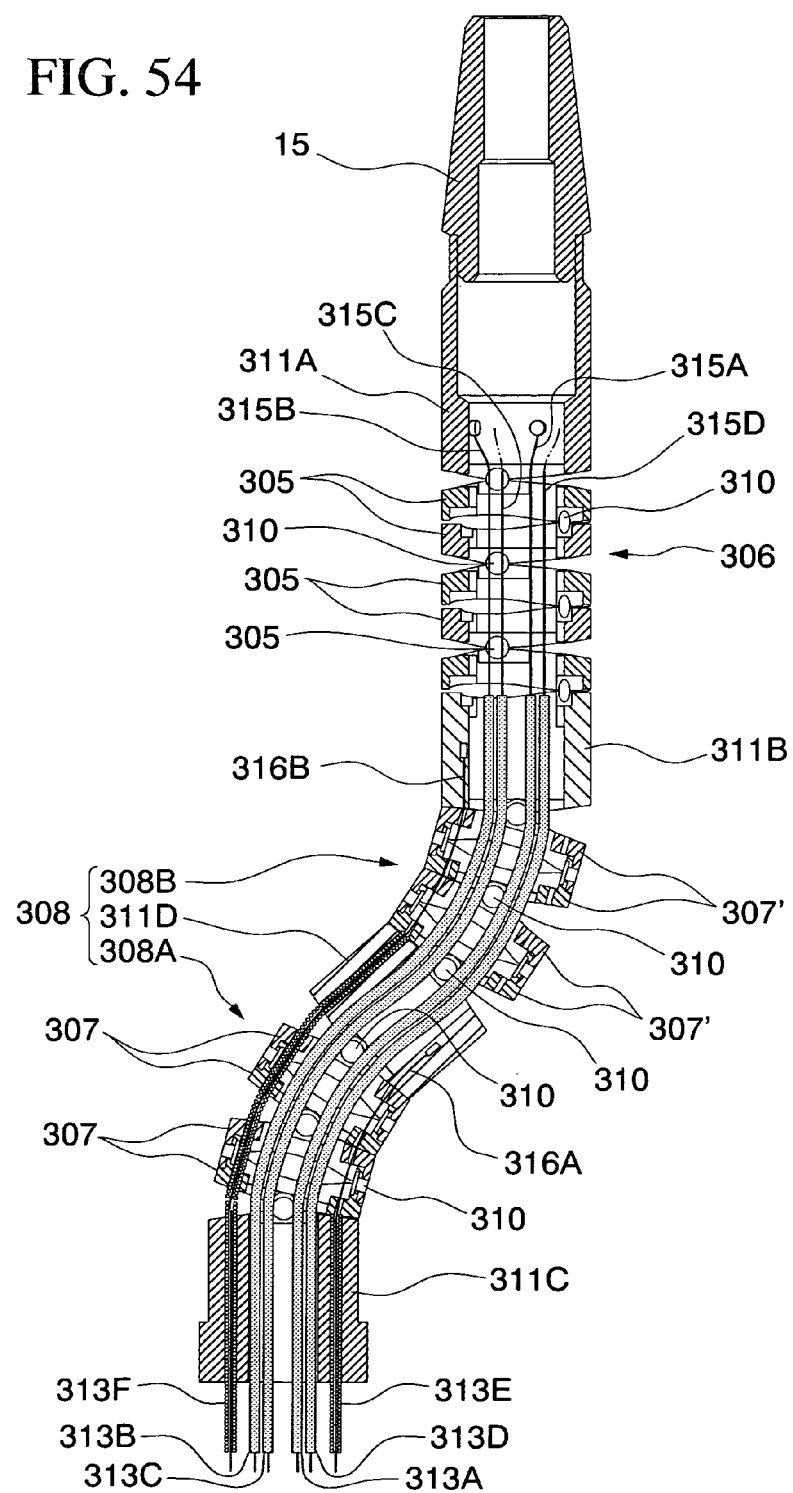
FIG. 54 shows a bending state of the arm member of the medical treatment endoscope in crosssectional view.
Figure 55:
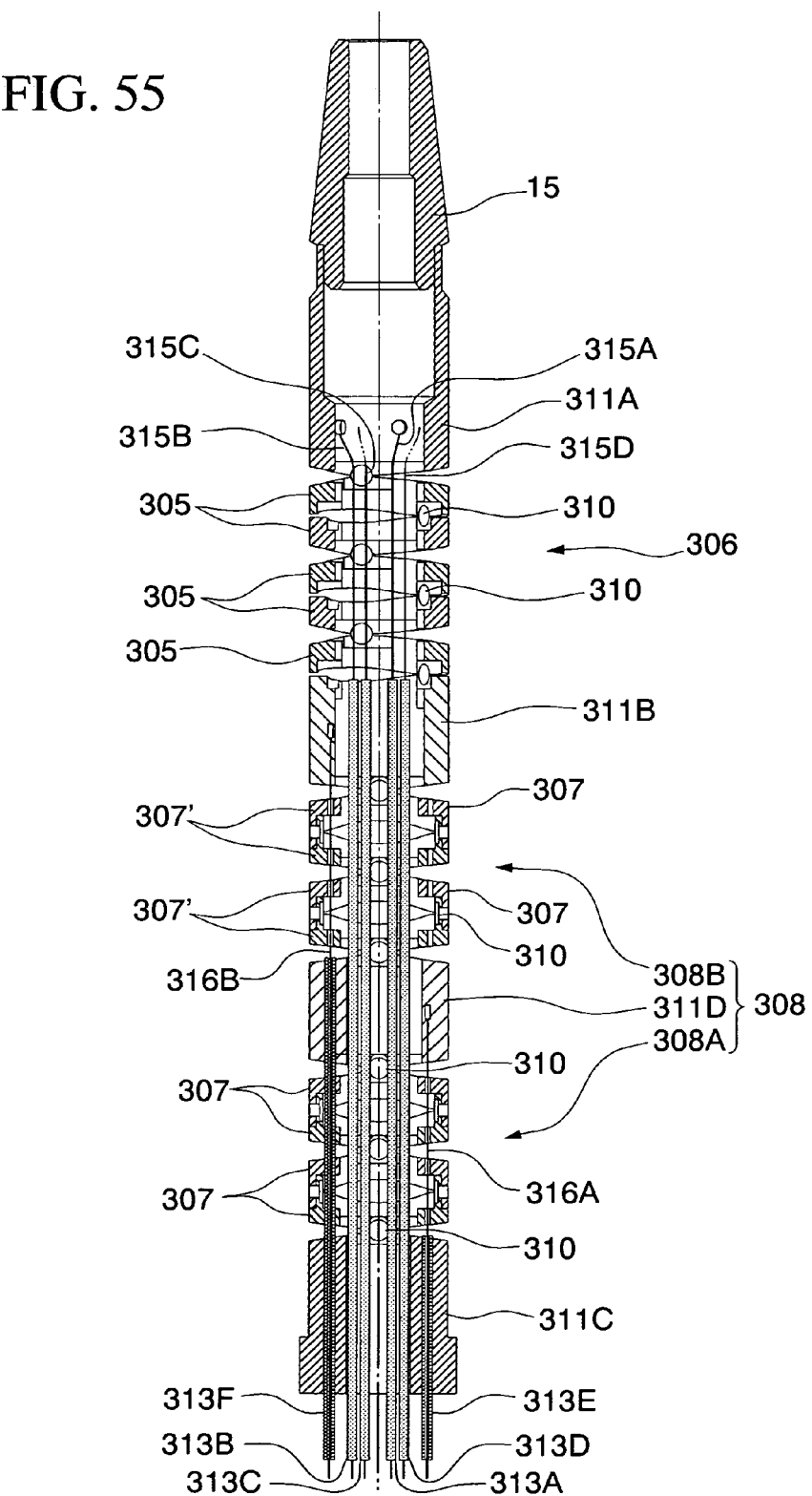
FIG. 55 shows an initial state of the arm member of the medical treatment endoscope in crosssectional view.

As illustrated in FIG. 43, a medical treatment endoscope 300 includes a first sheath 301 similarly configured to the medical treatment endoscope 1 according to the first embodiment; a second sheath 303A having a first arm member 302A and protruding from the first sheath 301; and a third sheath 303B having a second arm member 302B and protruding from the first sheath 301. Since the first arm member 302A and the second arm member 302B have approximately the same configuration, the first arm member 302A will be mainly explained hereafter.

As illustrated in FIGS. 44 to 52, the first arm member 302A includes: a first bending part 306 having a first joint ring 305 pivotally attached thereto; and a second bending part 308 where the first joint ring 305 bends in a first bending direction and in a second bending direction crossing with the first bending direction around the center of a first direction D1 that is parallel with a longitudinal direction (central axis direction) C of the first sheath 301, a second joint ring 307 which bends in the second direction D2 away from the longitudinal direction of the first sheath 301 is pivotally attached to the second base end bending part 308A, the base end of the second base end bending part 308A is joined to the sheath front end part 301A of the first sheath 301, the second joint ring 307 bending in the first direction D1 from the second direction D2 is pivotally attached to the second bending part 308, and the tip of the second tip end bending part 308B is joined to the base end of the first bending part 306.

As illustrated in FIGS. 53 to 60, the first joint ring 305 is pivotally supported at four points by support axis parts 310 which are disposed on a plane defined by a vertical direction of an image observed with a viewing device 12 (up and down direction in FIG. 56) and by a horizontal direction (right and left direction in FIG. 56) so that the vertical and horizontal direction are orthogonal (AX1 direction and AX2 direction in FIG. 56) and 45 degrees offset.

The second joint ring 307 and a second joint ring 307' are pivotally supported by four support axis parts 310 that are disposed on a plane defined by two directional lines (AX3 and AX4 illustrated in FIG. 56) rotatively offset by a predetermined angle with respect to the directions AX1 and AX2. The second bending part 308 therefore bends in the direction which passes through an object lens (objective optical system) 23 provided at the viewing device 12 and inclines relative to a plane orthogonal to the longitudinal direction C of the first sheath 301, and the tip of the second bending part 308 separates away from the perspective field of the viewing device 12.

The second joint rings 307 and 307' are pivotally attached to each other and urged in a direction so that a linear state of the second bending part 308 is maintained. A tip end surface 307*a* and a base end surface 307*b* are formed on the second joint rings 307 and 307' so that the tip end surface 307*a* and the base end surface 307*b* make contact with each other with the maximum bent state of the second bending part 308, and so that the tip end surface 307*a* and the base end surface 307*b* incline by a predetermined angle so as to be able to separate from each other according to deformation of the second bending part 308 into linear state.

A tip part 15 and the first bending part 306 are pivotally attached to each other via a solid short pipe 311A. The first bending part 306 and the second bending part 308 are pivotally attached to each other via a solid short pipe 311B. The second bending part 308 and the sheath front end part 301A are pivotally attached to each other via a solid short pipe 311C. The second base end bending part 308A and the second tip end bending part 308B are pivotally attached to each other via a solid short pipe 311D.

Notches 312 extending in the longitudinal directions of the first bending part 306 and second bending part 308 are provided to the second joint rings 307 and 307' and the short pipes 311B, 311C, 311D. Provided on the short pipe 311B are the notches 312' at four points in the up-down direction and right-left direction. Provided on the short pipe 311D is a notch 312' having an enlarged open end so that two neighboring coil tubes can be inserted. Provided on the short pipe 311C is a similar notch 312' at the position 180 degrees rotated from there.

Fitted to the notch 312 of the short pipe 311B are the tips of coil tubes 313A, 313B, 313C, 313D. The tip of the coil tube 313E is fitted to the notches 312 and 312' of the short pipe 311D, and the coil tubes 313A, 313B, 313C, 313D are inserted therethrough. The tip of the coil tube 313F is fitted to the notches 312 and 312' of the short pipe 311C, and the coil tubes 313A, 313B, 313C, 313D, and 313E are inserted therethrough.

In addition, the medical treatment endoscope 300 includes first bending wires (first operating members) 315A, 315B, 315C, and 315D, inserted through the first bending part 306 and the second bending part 308, for bending the first bending part 306; and second bending wires (second operating members) 316A and 316B, inserted through the second bending part 308, for bending the second bending part 308.

The tips of the first bending wires 315A, 315B, 315C, 315D are connected to the short pipe 311A. The first bending wires 315A, 315B, 315C, 315D are retractably inserted through the coil tubes 313A, 313B, 313C, 313D respectively between the short pipe 311B and a manipulation side of the operation part which is not shown in the drawings. That is, they are inserted in the up-down direction and in the right-left direction of FIG. 56.

The first bending wires 315A, 315C in this state are connected to a vertical bending operating part of the operation part which is not shown in the drawings. The first bending wires 315B, 315D are connected to a horizontal bending operating part of the operation part which is not shown in the drawings. Operating these operation parts extends and retracts the first bending wires 315A, 315B, 315C, 315D respectively; thereby bending the first bending part 306 in the desirable direction.

Figure 56:
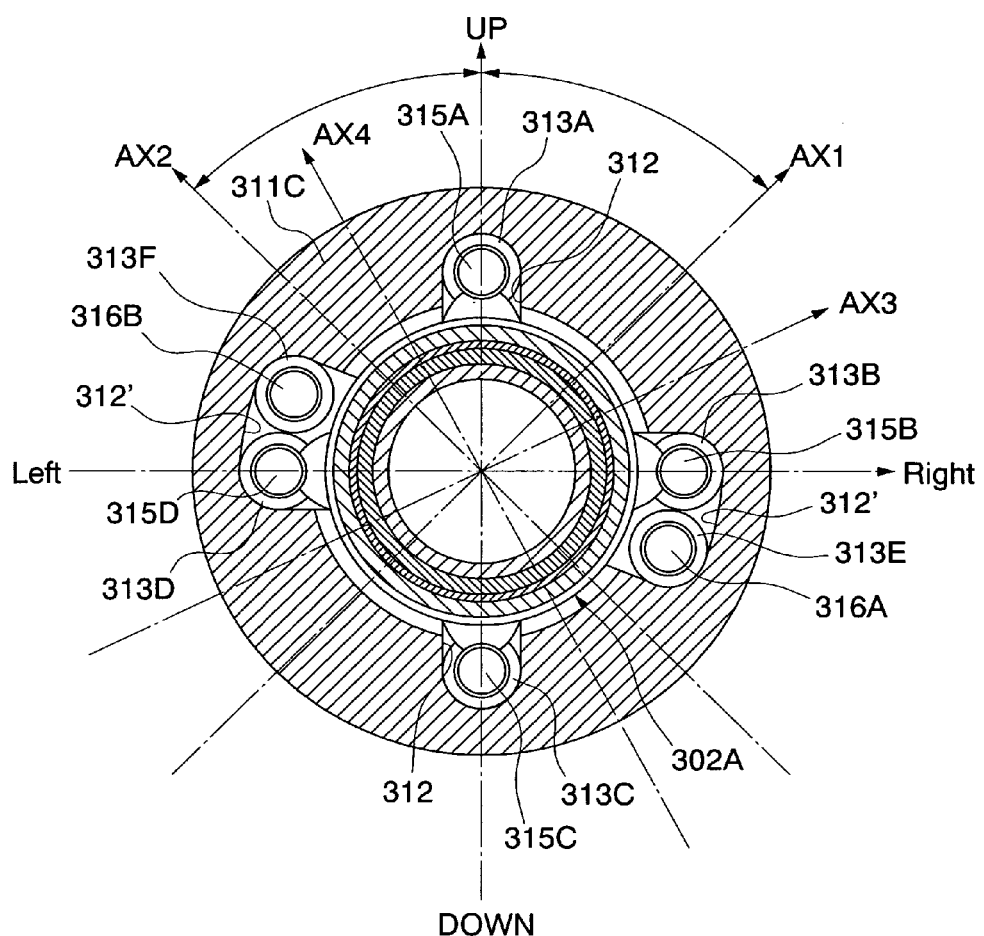
FIG. 56 shows the arm member of the medical treatment endoscope in crosssectional view.
Figure 57:
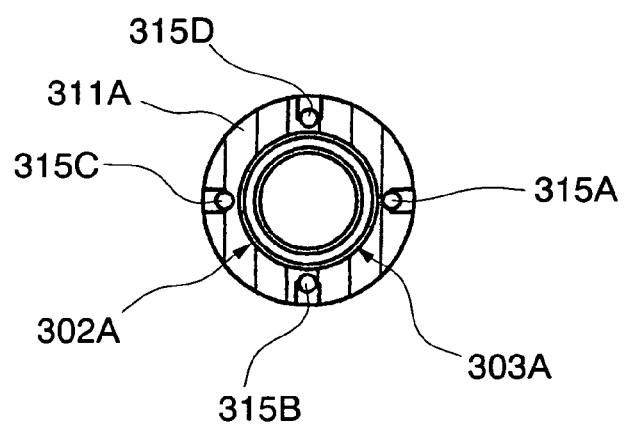
FIG. 57 is a cross-sectional view along the line I-I in FIG. 53.
Figure 58:
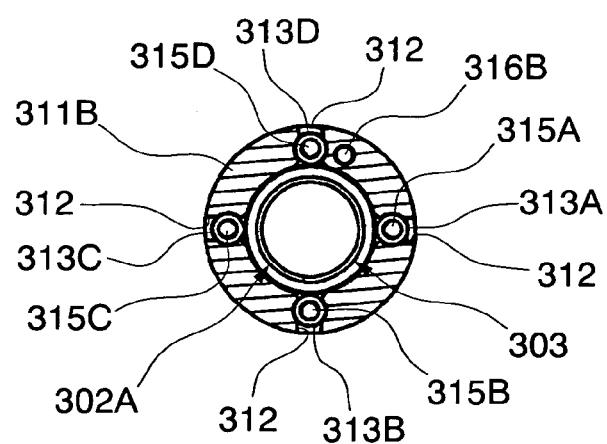
FIG. 58 is a cross-sectional view along the line II-II in FIG. 53.
Figure 59:
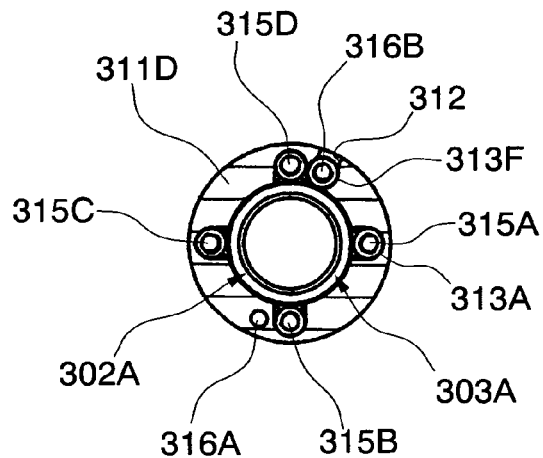
FIG. 59 is a cross-sectional view along the line III-III in FIG. 53.
Figure 60:
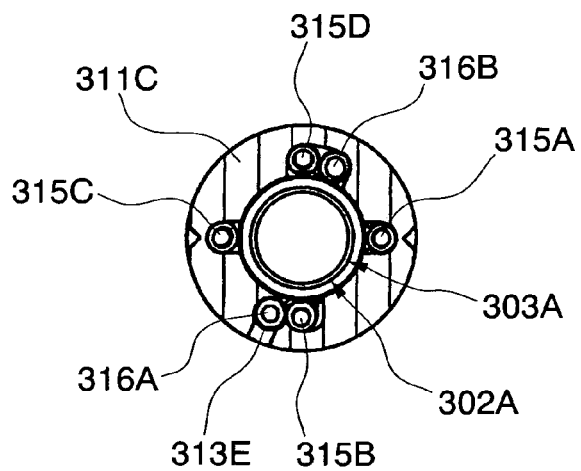
FIG. 60 is a cross-sectional view along the line IV-IV in FIG. 53.

The tip of the second bending wire 316A is connected to the short pipe 311D and retractably inserted through the coil tube 313E between the short pipe 311C and the operation part for manipulation. The tip of the coil tube 313E is connected to the short pipe 311C. That is, the coil tube 313E is inserted at a clockwise offset position by 45 degrees relative to the direction AX3 as illustrated in FIG. 56. The base end of the second bending wire 316A is connected to an open/close operating part which is not shown in the drawings. Operating the open/close operating part extends and retracts the second bending wire 316A; thereby bending the second base end bending part 308A.

The tip of the second bending wire 316B is connected to the short pipe 311B and retractably inserted through the coil tube 313F between the short pipe 311D and the operation part for manipulation. The tip of the coil tube 313F is connected to the short pipe 311D. That is, the coil tube 313F is inserted at a counter clockwise offset position by approximately 45 degrees relative to the direction AX4 as illustrated in FIG. 56. The base end of the second bending wire 316B is connected to the open/close operating part which is not shown in the drawings. Operating the open/close operating part extends and retracts the second bending wire 316B; thereby bending the second tip end bending part 308B.

The diameter of first bending wires 315A, 315B, 315C, 315D and the second bending wires 316A, 316B is 0.45 mm, which is greater than that of 0.36 mm for bending wires 17A, 17B, 17C, and 17D in the medical treatment endoscope 1 according to the first embodiment. Applied on the surfaces of the first bending wires 315A, 315B, 315C, 315D and the second bending wires 316A, 316B are a PTFE (polytetrafluoroethylene) coating for reducing friction resistance.

Figure 61:
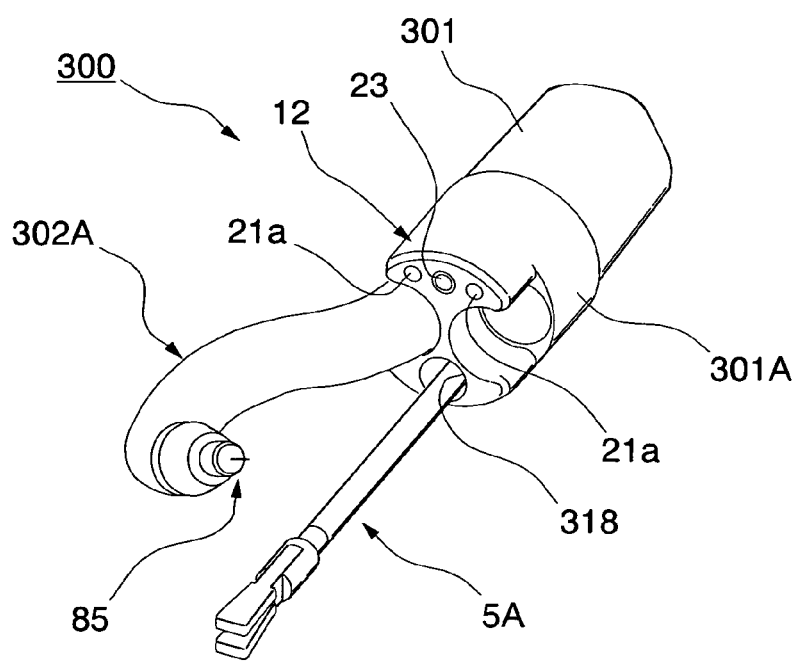
FIG. 61 is a perspective view of a tip of the medical treatment endoscope.

As shown in FIG. 61, provided through the first sheath 301 and sheath front end part 301A is a channel 318 that allows an endoscopic treatment instruments, e.g., a grasping forceps 5A to be freely inserted therethrough.

Figure 62:
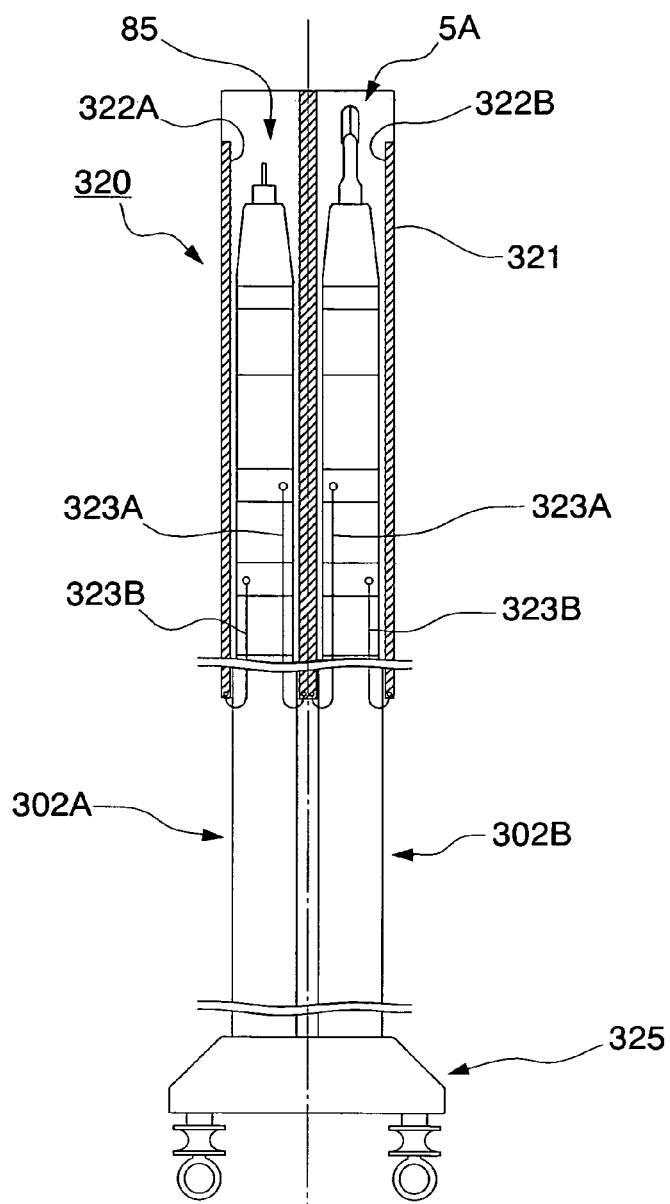
FIG. 62 is a schematic representation of a modified example of the medical treatment endoscope.
Figure 63:
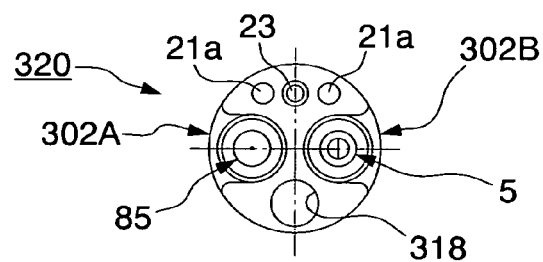
FIG. 63 shows the medical treatment endoscope of FIG. 62 in front view.
Figure 64:
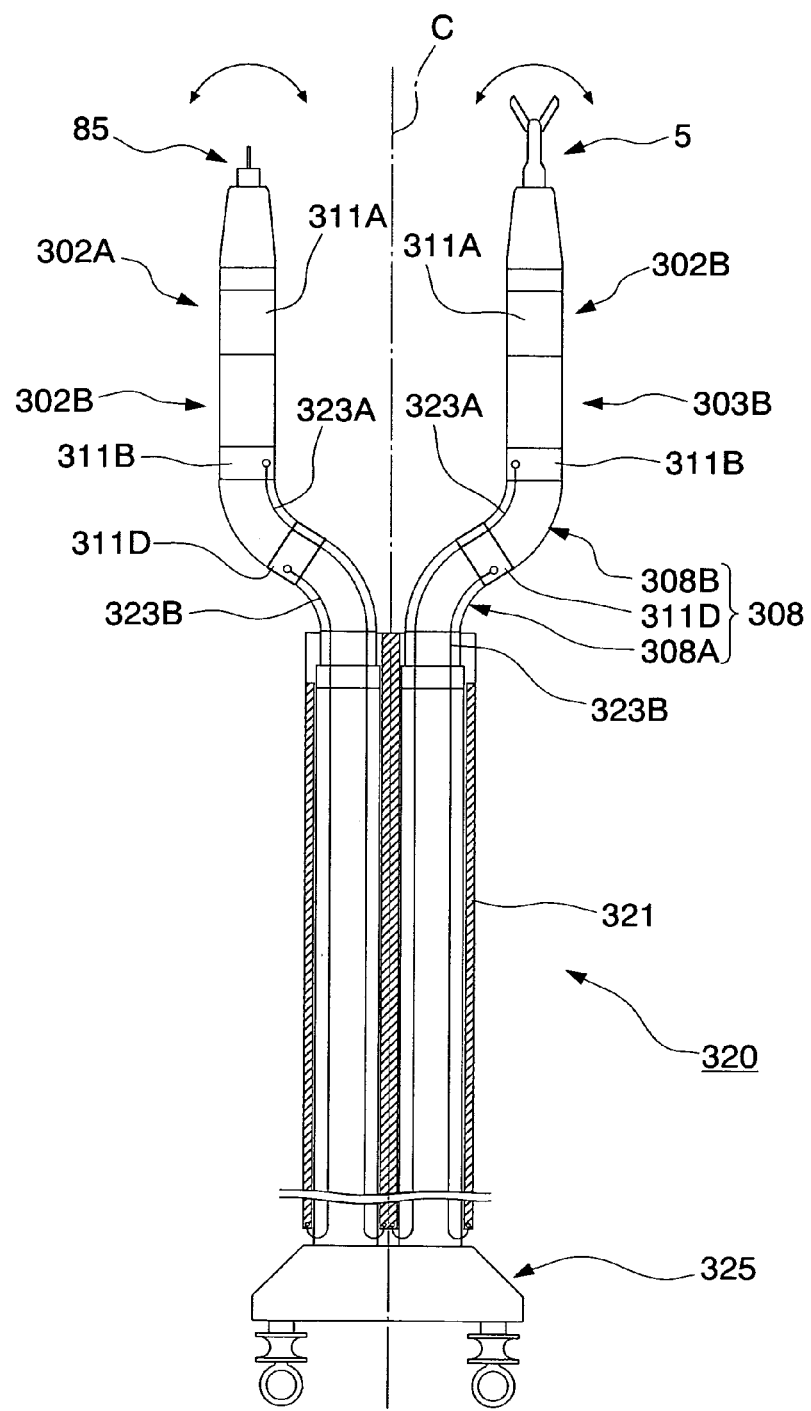
FIG. 64 shows a bending state of the medical treatment endoscope of FIG. 62.

In addition, as illustrated in FIGS. 62 to 64, the medical treatment endoscope 320 may further include a flexible storage sheath 321 for containing the tip portions of the first arm member 302A and second arm member 302B in an extended condition. Provided in the storage sheath 321 are a first arm member lumen 322A which allows the first arm member 302A to be inserted therethrough; a second arm lumen 322B which allows the second arm member 302B to be inserted therethrough; and extension/retraction operating wires 323A and 323B for bending the second bending part 308 while protruding and retracting the arm members 302A and 302B from each lumen 322A, 322B. The tip of the extension/retraction operating wire 323A connected to the short pipe 311B is inserted through the first arm member lumen 322A or the second arm lumen 322B, and is connected to the base end of the first arm member lumen 322A or the second arm lumen 322B.

The tip of the extension/retraction operating wire 323B connected to the short pipe 311D is inserted through the first arm member lumen 322A or the second arm lumen 322B, and is connected to the base end of the first arm member lumen 322A or the second arm lumen 322B.

A drawing force is applied to the extension/retraction operating wires 323A and 323B according to the protrusion of the first arm member 302A and second arm member 302B from the tip of the storage sheath 321 caused by the movement of the storage sheath 321 toward the operating part 325. This results in bending the second bending part 308 into a desirable direction since the extension/retraction operating wires 323A and 323B act similarly to the second bending wires 316A, 316B.

Next, the operation of the medical treatment endoscope 300 according to the present embodiment will be explained.

Figure 65:
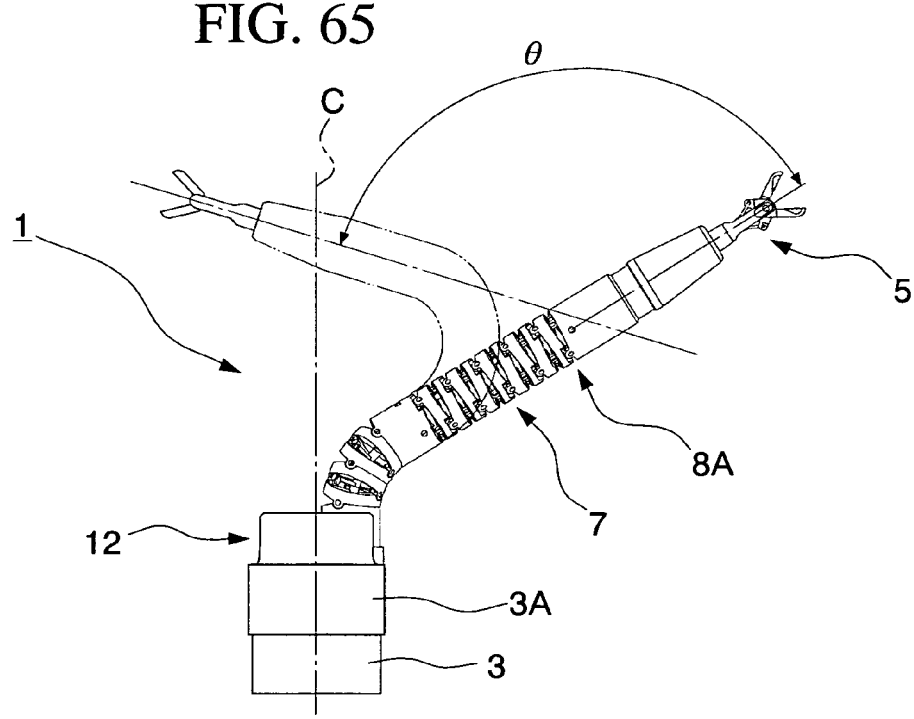
FIG. 65 is a perspective diagram illustrating a bending state of the arm member of the medical treatment endoscope according to the first embodiment.

As illustrated in FIG. 65, a bending part 7 of the medical treatment endoscope according to the first embodiment must swing in a range of angle θ for conducting a predetermined treatment by opening the first arm member 8A and the second arm member 8B relative to the first sheath 301. Some axial force caused by the extending and retracting bending wire is therefore used for bending the bending part 7. Therefore, a sufficient force may not be generated sometimes at the tip of the treatment instruments while maintaining the bending state of the bending part 7 if the first arm member 8A and the second arm member 8B are in a bending state.

Figure 66:
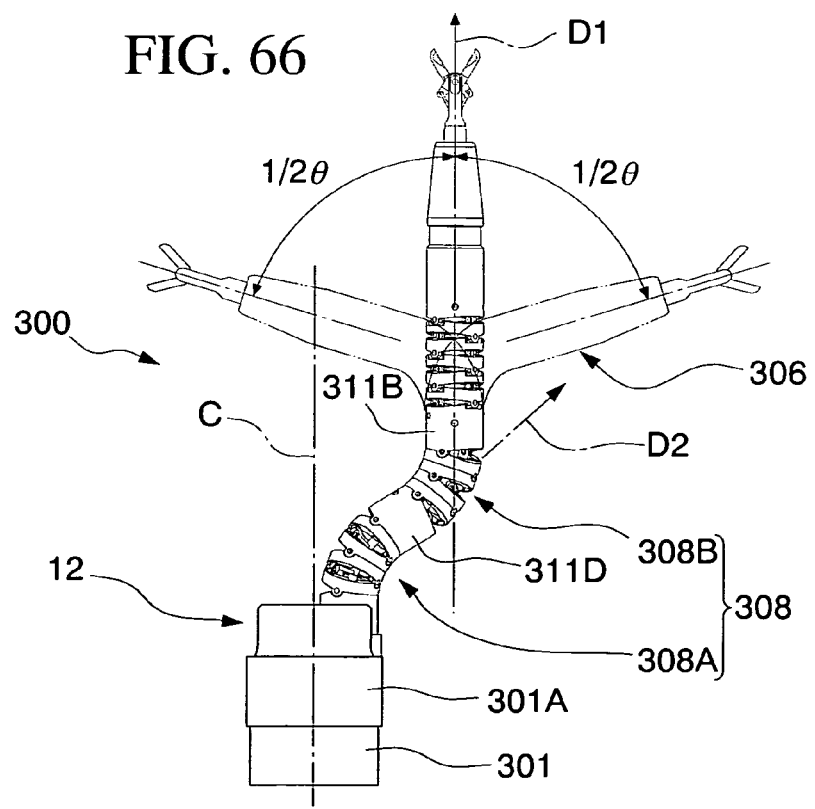
FIG. 66 is a perspective diagram illustrating a bending state of the arm member of the medical treatment endoscope according to the fourth embodiment.

In contrast, as illustrated in FIG. 66, the second base end bending part 308A of the medical treatment endoscope 300 according to the present embodiment bends in the second direction D2 which separates away from the longitudinal direction C of the first sheath 301 and bends the second tip end bending part 308B in the first direction D1. This allows the first bending part 306 in the vicinity of the tip of the short pipe 311B to bend in a range of angle θ that is the same as that of the first embodiment by a stepwise swing by approximately ½θ around the first direction D1. Therefore a smaller axial force generated in the first bending wires 315A, 315B, 315C, 315D can bend the bending part 7, thereby allowing the tip of the treatment instruments to generate a greater force.

Retracting the second bending wires 316A, 316B fixes the bending state of the second bending wires 316A, 316B at the second bending part 308 because a tip end surface 307a of the second joint ring 307 in the second bending part 308 makes contact with a base end surface 307b of the neighboring second joint ring 307 disposed separately. The continuous retraction of the second bending wires 316A, 316B thereby desirably maintains the bending state of the second bending part 308.

Instead, slacking the second bending wires 316A, 316B releases the bending state of the second bending part 308. The restoration (resilience) in this state of the second bending part 308 into the linear state increases while bending the second bending part 308 from the linear extending state. Therefore, slacking, i.e., stopping the retraction of the second bending wires 316A, 316B, releases the bending state of the second bending part 308.

Figure 67:
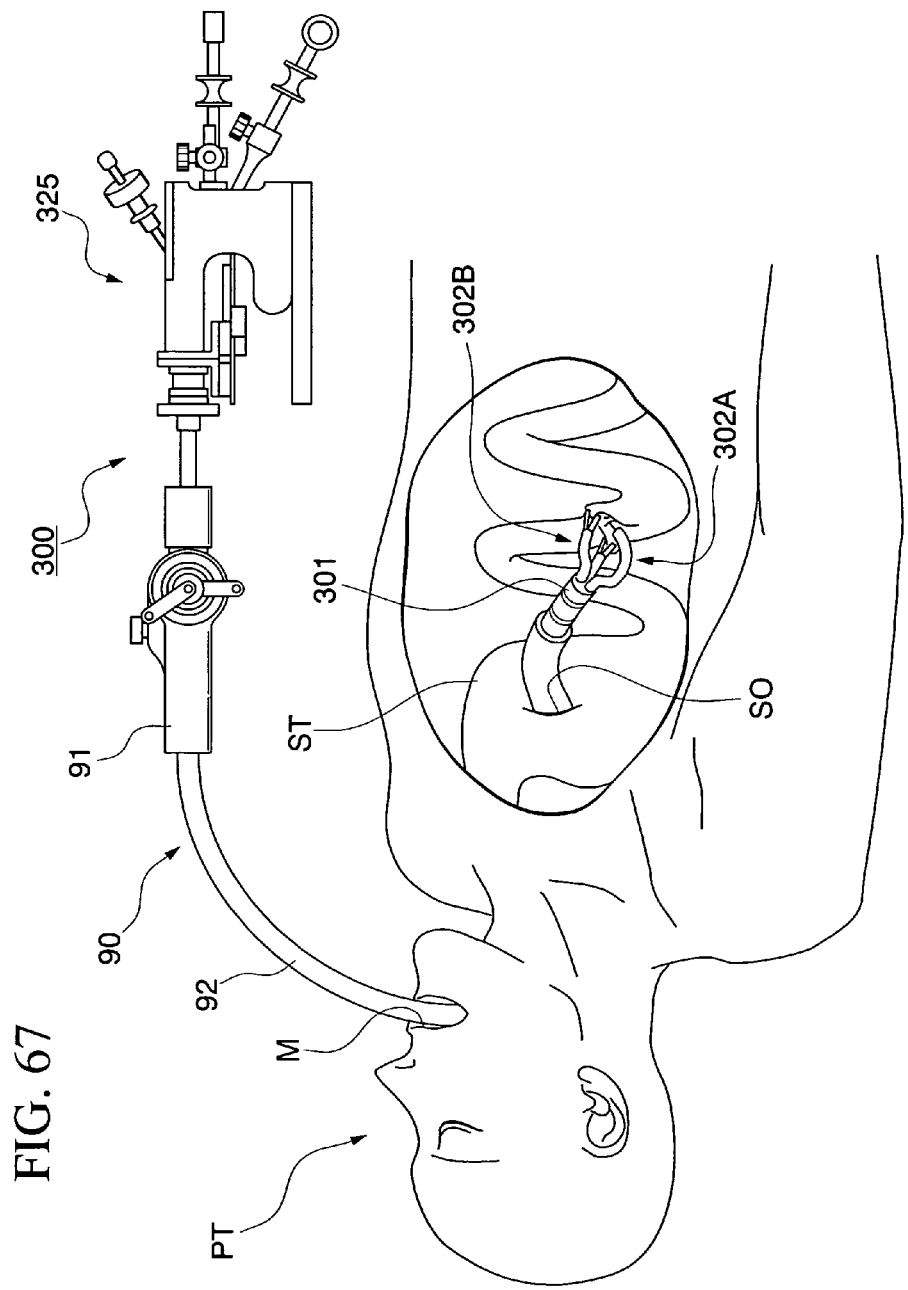
FIG. 67 is a view explaining the state where an overtube having the medical treatment endoscope according to the fourth embodiment inserted therethrough is inserted into an abdominal cavity via a stomach during medical procedure.
Figure 68:
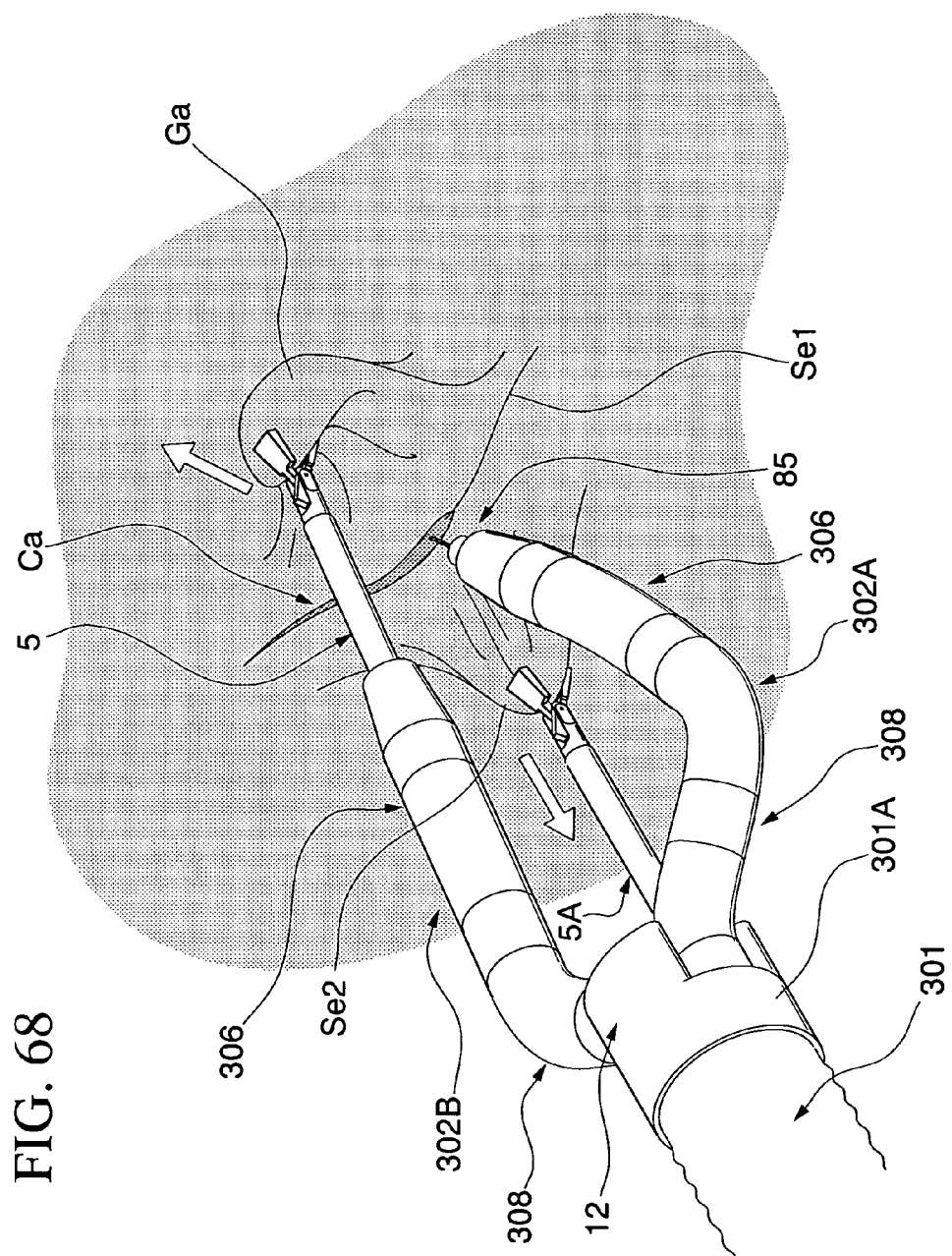
FIG. 68 illustrates a manipulation procedure using a medical treatment endoscope.

A natural orifice medical procedure using the medical treatment endoscope 300 according to the present embodiment will be explained with reference to a case as shown in FIGS. 67 and 68 where a gallbladder extraction is conducted similarly to the first embodiment by inserting the medical treatment endoscope from the mouth M of the patient PT into the stomach ST, forming an opening on the stomach wall, and inserting a first sheath 301 of the medical treatment endoscope into the abdominal cavity AC.

The medical procedure according to the present embodiment includes: a step of inserting a medical treatment endoscope 300 in the vicinity of an affected part; a step including disposing a high frequency knife (first endoscopic treatment instrument) 85 via the first arm member 302A, disposing a grasping forceps (second endoscopic treatment instrument) 5 in the vicinity of the affected part via the second arm member 302B, and disposing a grasping forceps (third endoscopic treatment instrument) 5A in the vicinity of the affected part via a channel 318 of the first sheath 301; a step of bending the first arm member 302A and the second arm member 302B into different directions respectively; and a step of conducting treatment to the affected part with the grasping forceps 5, the high frequency knife 85, and the grasping forceps 5A.

In the insertion step, an overtube 90 is introduced into an abdominal cavity AC via an opening SO formed on a stomach ST similarly to the first embodiment.

Consequently inserted through a lumen 88 of the overtube 90 are a first sheath 301, a second sheath 303A, and a third sheath 303B. The first arm member 302A and the second arm member 302B are protruded from the tip of the overtube 90.

The high frequency knife 85 is inserted into the second sheath 303A and the first arm member 302A similarly to the first embodiment, and the grasping forceps 5 is inserted into the third sheath 303B and the second arm member 302B similarly to the case of the high frequency knife 85. In addition, the grasping forceps 5A is inserted into a channel 318 provided in the first sheath 301.

The medical procedure transfers to the next step, i.e., the disposing step. The second arm member 302B is positioned to grasp the affected part with the grasping forceps 5.

Operating an open/close operating part retracts a second bending wire 316A until a tip end surface 307a of a second joint ring 307 makes contact with a base end surface 307b, thereby bending the second base end bending part 308A from a longitudinal direction C to a second direction D2. Retracting further the second bending wire 316B until the tip end surface 307a of the second joint ring 307 makes contact with the base end surface 307b bends a second tip end bending part 308B from a second direction D2 to a first direction D1. The direction of the second bending part 308 is thus fixed. Note that the second bending wires 316A, 316B may be retracted simultaneously.

The bending operating part is consequently operated to swing the first bending part 306 around the first direction D1 in order to inspect the affected part with the viewing device 12. Operating a forceps-operating part which is not shown in the drawings extends, for example, the grasping forceps 5 toward the second arm member 302B, thereby grasping and retracting a cervical part Ga of the gallbladder to expose a Calot trigone Ca.

The medical procedure in this state transfers to the treatment step.

A serosal membrane Se1 is incised a little at a time with the high frequency knife 85 inserted in the first arm member 302A by operating the bending operating part. Conducted so as to apply adequate tension to the incised part are picking the incised part with the grasping forceps 5A inserted through the channel 318 while grasping the cervical part Ga of the gallbladder with the grasping forceps 5; grasping a serosal membrane Se2 opposite the cervical part Ga of the gallbladder; drawing the grasped serosal membrane Se2 toward the endoscopist; bending the first bending part 306 of the second arm member 302B away from the grasping forceps 5A; and adjusting the drawing direction. Meanwhile, adipose tissue and fiber tissue including serous membrane are peeled with the high frequency knife 85 while bending the first bending part 306 of the first arm member 302A.

The gallbladder extraction is conducted by the operation similar to the first embodiment after identifying the gallbladder in this manner.

In addition to the previously explained gallbladder extraction, the medical treatment endoscope according to the present invention can be used for various manipulations, e.g., appendectomy, gastroduodenal bypass, liver biopsy, biopsy of the pancreas, tubal interruption, and hysterectomy.

In the medical treatment endoscope 300, provided instead of the solid open/close mechanism provided at the medical treatment endoscope according to the first embodiment are flexible second bending parts 308 disposed at root parts of the first arm member 302A and the second arm member 302B. The length of the solid portions in the first arm member 302A and the second arm member 302B shorter than that of the medical treatment endoscope provides higher flexibility, thereby improving insertability. The tip end surface 307a and the base end surface 307b formed in the second joint ring 307 incline so that the tip end surface 307a and the base end surface 307b make contact with each other in the second joint ring 307 at the second bending part 308 when the second bending wires 316A, 316B are drawn. Drawing the wires continuously to maintain the contact between the tip end surface 307a and the base end surface 307b allows the second bending part 308 to be fixed in the predetermined bending state.

The first bending part 306 in this state can be bent with respect to the first direction D1. The bending range of the first bending part 306 while using treatment instruments can be narrower than in the case of the medical treatment endoscope according to the first embodiment. In addition, it is possible to reduce a force necessary to bend the first bending part 306 and increase an operation force at the tip of the first arm member 302A and the tip of the second arm member 302B.

Also, since the first bending wires 315A, 315B, 315C, 315D are inserted at positions conforming in the vertical and horizontal directions defined on an image observed with the viewing device, intuitive operation while observing the image can be conducted. In addition, the second bending wires 316A, 316B inserted at the positions rotated by a predetermined degree relative to the positions of the first bending wires 315A, 315B, 315C, 315D allow the second base end bending part 308A to be directed outward and downward relative to the center of the first sheath 301 when the second bending part 308 is bent. The affected part, the first arm member 302A, or the second arm member 302B that is captured by the viewing device 12 can be viewed or treated from above since the central axis of the first bending part 306 is beneath the central axis of the first sheath 301.

In addition, formed at the first joint ring 305 and the second joint ring 307 are notches 312, 312' extending in the longitudinal directions of the first bending part 306 and the second bending part 308. The coil tubes 313A, 313B, 313C, 313D, 313E, and 313F are inserted through the notches 312 and 312'. The outer diameters of the first joint ring 305 and the second joint ring 307 may be desirably maintained if the thickness of the wall of these joint rings is increased.

The dispositions of the second bending wires 316A, 316B inserted through the second joint ring 307 are offset rotated by approximately 45 degrees relative to the pivotally attached second joint ring 307. Therefore, retracting the second bending wire 316A to bend the second base end bending part 308A, or retracting the second bending wire 316B to bend the second tip end bending part 308B rotates the neighboring second joint rings 307 or the joint rings 307' around the axes AX3 and Ax4, thereby abutting the neighboring second joint rings 307 or 307'. The second bending part 308 can be restored to a linear state by releasing the bending state of the second bending part 308 retracted by the second bending wires 316A, 316B since the pivotally attached second joint rings 307 and 307' are urged in a direction in which the linear state of the second bending part 308 is maintained. Therefore, a smaller outer diameter of the bending part can be maintained.

The outer diameter of each bending wire greater than the diameter of the bending wire in the medical treatment endoscope can increase the wire-breaking force, thereby allowing retraction with a greater force. The PTFE coating applied on the wire surface can reduce the friction resistance, thereby providing greater force at the tips of the wires.

Also, the channel 318 provided at the sheath front end part 301A of the first sheath 301 allows treatment instruments to be disposed in the channel 318, thereby allowing more complex procedures to be conducted. Furthermore, the number of exchanges of the treatment instruments can be reduced.

A drawing force can be applied to the extension/retraction operating wires 323A and 323B according to the protrusion of the first arm member 302A and second arm member 302B from the tip of the storage sheath 321. The second bending part 308 can therefore be bent in a desired direction simply by protruding the first arm member 302A and the second arm member 302B from the tip of the storage sheath 321 since the extension/retraction operating wires 323A and 323B have similar functions as those of the second bending wires 316A, 316B.

Figure 69:
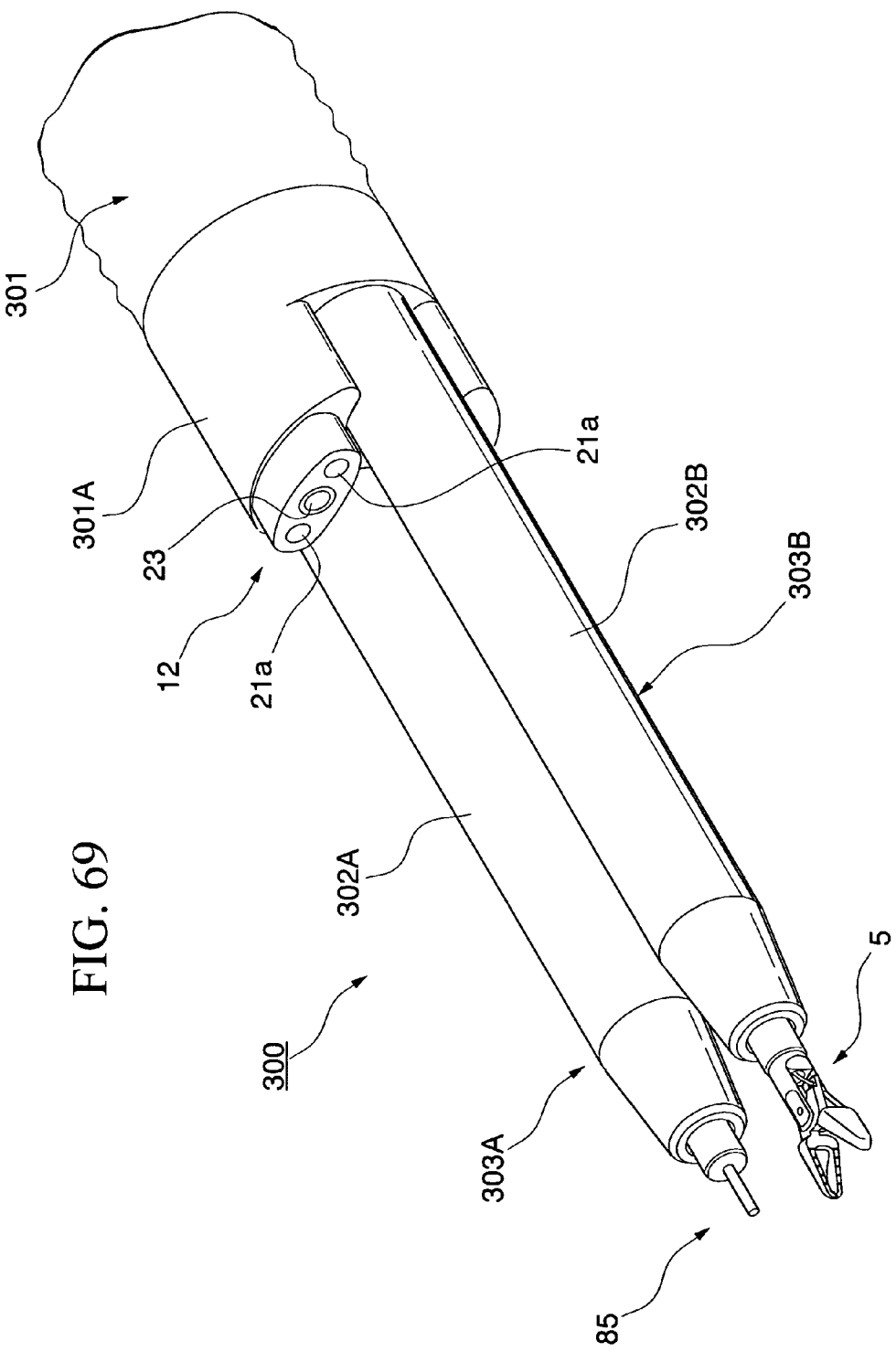
FIG. 69 is a view showing the structure of a modified example of the tip of the medical treatment endoscope according to the fourth embodiment.

Note that the second sheath 303A having the grasping forceps 5 therethrough may be used as illustrated in FIG. 69.

In addition, the high frequency knife 85 is inserted into the channel 318 provided in the first sheath 301 in this case.

Figure 70:
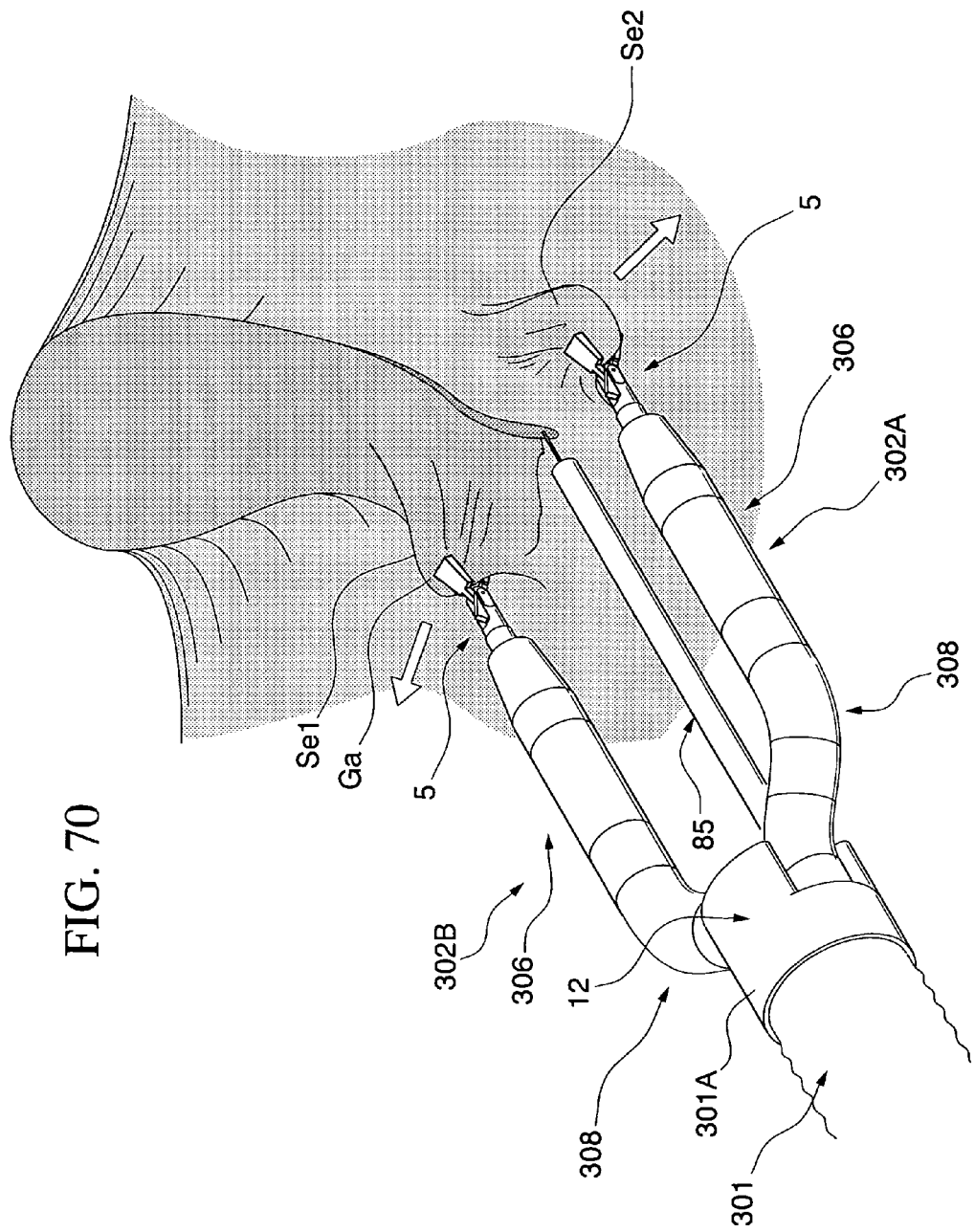
FIG. 70 illustrates a manipulation procedure using the medical treatment endoscope shown in FIG. 69.
Figure 71:
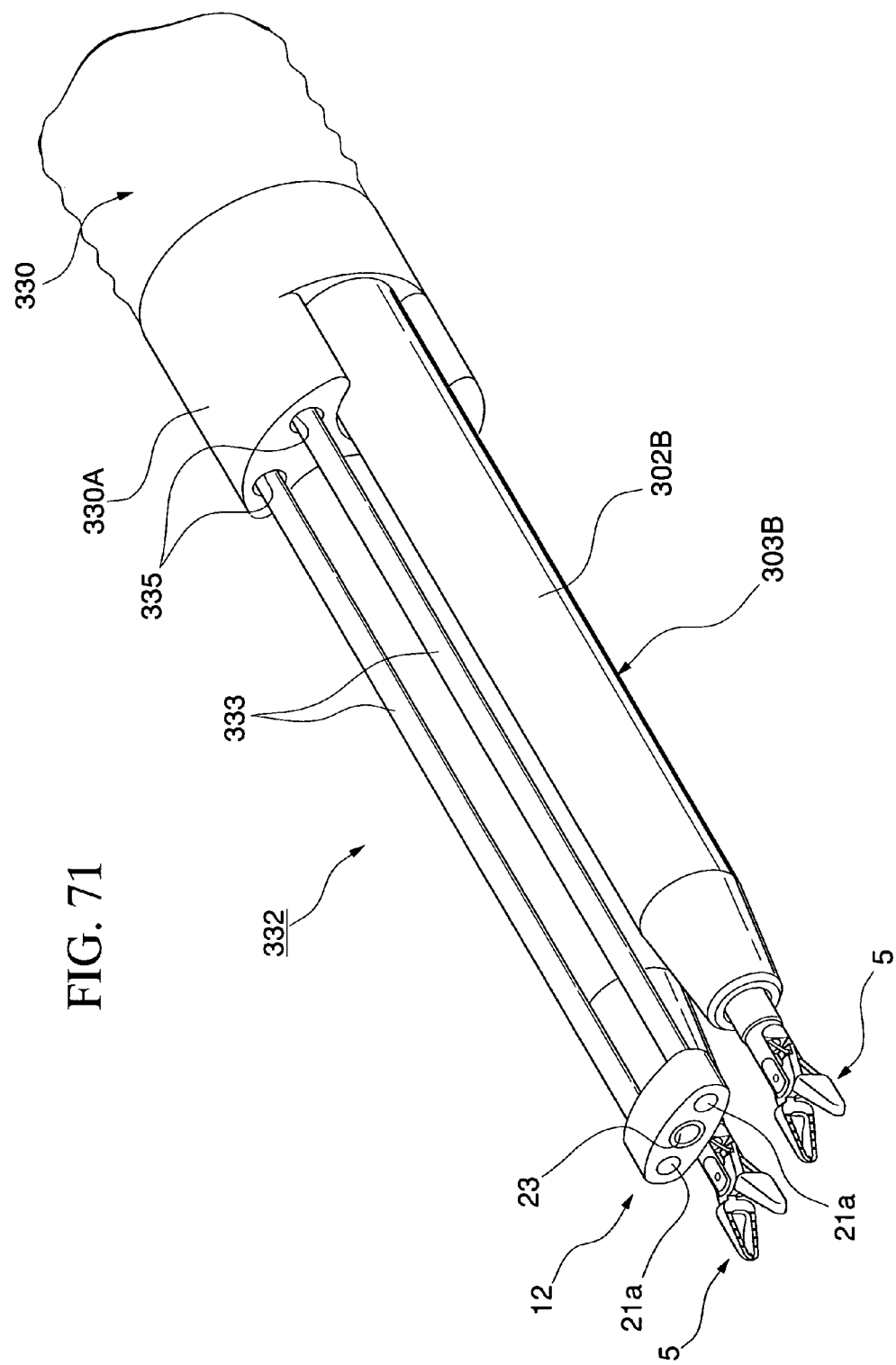
FIG. 71 is a view showing the structure of a modified example of the tip of the medical treatment endoscope according to the fourth embodiment.

The serosal membrane Se1 of the gallbladder is incised a little at a time with the high frequency knife 85 inserted through the channel 318 in the treatment step conducted during the medical procedure explained above. As illustrated in FIGS. 70 and 71, conducted in order to apply an appropriate tension to the incised part are grasping the cervical part Ga of the gallbladder with the grasping forceps 5 disposed at the second arm member 302B; picking up the incised part with the grasping forceps 5 disposed to the first arm member 302A; and grasping the serosal membrane Se2 opposite the cervical part Ga of the gallbladder. The first bending parts 306 of the first arm member 302A and the second arm member 302B are bent away in separate directions to adjust the retraction direction. Meanwhile, adipose tissue and fiber tissue including serous membrane can be peeled by extending and retracting the high frequency knife 85 inserted through the channel 318. Note that, in addition to the above explanation, the first arm member 302A, the second arm member 302B, and the channel 318 are variously combined regardless of the above explanation.

Also, a medical treatment endoscope 332 may include a viewing unit 331 having an illuminating lens 21a and an object lens 23 that is extendable away from a sheath front end part 330A toward the tips of the first arm member 302A and the second arm member 302B as illustrated in FIG. 71.

In this case, a flexible protection tube 333 is configured to extend from the viewing unit 331 for containing and protecting an observation optical system including the object lens 23 and the illuminating optical system for introducing a light beam into the object lens 21a. Note that these optical systems are not shown in the drawings. The protection tube 333 is configured to be extendable relative to the storage lumen 335 disposed in the first sheath 330.

The inserted state of the medical treatment endoscope 332 provides a wide perspective since the viewing unit 331 is extendable to the vicinity of the tips of the first arm member 302A and the second arm member 302B when the first arm member 302A and the second arm member 302B are inserted.

What is claimed is:

1. A medical treatment endoscope comprising:
   a longitudinal member including a longitudinal axis and comprising a channel along the longitudinal axis;
   an arm section disposed to be free to be protruded from and inserted into a distal end of the channel;
   a bending part disposed to a proximal end of the arm section and capable of bending;
   a wire member for bending the bending part;
   an one-end-connecting part disposed at the bending part and connected to the wire member;
   an other-end-connecting part disposed at the longitudinal member and connected to the wire member; and
   an operating part for the arm section moving relative to the longitudinal member in a protruding direction of the arm section,
   wherein an operation of the operating part configured to cause a drawing tension of the wire member to generate in a direction from the one-end-connecting part to the other-end-connecting part by the arm section moving relative to the longitudinal member in the protruding direction of the arm section such that the bending part is bent, and
   wherein the bending part includes:
      a first bending part to which pivotal joint rings are attached;
      a second bending part which is connected to a proximal end of the first bending part at a distal end thereof, and pivotal second joint rings attached thereto;
      a plurality of first operating members inserted through the first bending part and the second bending part for bending the first bending part; and
      a plurality of second operating members inserted through the second bending part for bending the second bending part;
   a viewing device disposed at a tip of the longitudinal member independent from the arm section for observing an object;
   an illuminating member, for illuminating light onto the object, disposed at the tip of the longitudinal member independently from the arm section;

in a cross-sectional surface of the second bending part, a first axis line and a second axis line, provided at the second bending part, normal to each other, and the plurality of the first operating members are each inserted therebetween for rotating the first bending part; and in a cross-sectional surface of the second bending part, a third axis line and fourth axis line, provided at the second bending part, normal to each other, and the plurality of the second operating members are each inserted therebetween for rotating the second bending part; wherein:

the third and fourth axis lines are disposed from a first predetermined angle with respect to the first and second axis lines in a circumferential direction of the second bending part;

the plurality of first operating members are inserted at positions conforming in the vertical and horizontal directions defined on an image observed with the viewing device, the plurality of second operating members are inserted at positions rotated by the first predetermined angle relative to the positions of the plurality of first operating members;

the second joint rings have contact faces allowing all of the neighboring second joint rings to be abutted while the plurality of second joint rings which are constituted of the second bending part is capable of rotating around the third and fourth axis lines at a time;

each second joint ring has a tip surface and a base end surface that are inclined so that the second joint rings are capable of making contact under a maximum bending condition of the second bending part; and the second joint rings are capable of separating from each other along with deformation of the second bending part to the linear state.

2. The medical treatment endoscope according to claim 1, wherein the first operating members are disposed at positions conforming to the vertical and horizontal directions of an image observed with the viewing device; and the second operating members are inserted at positions rotatively offset from the first operating members by a predetermined angle.

3. The medical treatment endoscope according to claim 1, wherein notches extending along longitudinal directions of the first bending part and the second bending part are formed in each second joint ring, and a coil tube is inserted through each notch.

4. The medical treatment endoscope according to claim 1, wherein the first bending part bends in a first bending direction and a second bending direction which crosses the first bending direction, and the second bending part passes through an objective optical system disposed to the viewing device, the second bending part is inclined relative to a plane orthogonal to an axis orthogonal to a longitudinal direction of the longitudinal member, and the tip of the second bending part bends in a direction away from a perspective range of the viewing device.

5. The medical treatment endoscope according to claim 1, wherein the second operating member is disposed to be inserted through the second joint rings at positions rotatively offset by approximately 45 degrees relative to pivotal positions of the second joint rings.

6. The medical treatment endoscope according to claim 1, wherein the second joint rings are pivotally attached to each other so that the second joint rings are urged in a direction where the second bending part is maintained in a linear state.

7. The medical treatment endoscope according to claim 1, wherein a central axis line of the tip surface of the second bending part is approximately parallel with a longitudinal direction of the longitudinal member in the maximum bending state of the second bending part.

8. The medical treatment endoscope according to claim 7, wherein a distance between the central axis line of the tip surface of the second bending part in the maximum bending state and a central axis line of the longitudinal member is approximately half a distance between the central axis line of the longitudinal member and a tip of the first bending part while the first bending part and the second bending part are in maximum bending condition in directions separate from the longitudinal member.

9. The medical treatment endoscope according to claim 1, wherein the second bending part includes a second base end bending part and a second tip end bending part, the second base end bending part has a base end connected to the longitudinal member and a tip end bending in a second direction separate from a first direction parallel to a longitudinal direction of the longitudinal member, the second joint rings of the second bending part are pivotally attached to each other so that the second joint rings bend in the second direction, the second tip end bending part has a base end connected to the tip of the second base end bending part and a tip connected to the base end of the first bending part, and the second joint rings of the second tip end bending part are pivotally attached to each other so that the second joint rings bend from the second direction to the first direction.

10. The medical treatment endoscope according to claim 1, wherein the first predetermined angle is determined so that a distance between the third axis line and one of the plurality of the second operating members and a distance between the fourth axis line and another of the plurality of the second operating members are maximized.

11. The medical treatment endoscope according to claim 1, further comprising:

a third sheath having a second arm section having the first bending part and the second bending part, the third sheath being disposed to protrude from the longitudinal member, wherein the viewing device and the illuminating member are disposed at the tip of the longitudinal member independently of the third sheath.

\* \* \* \* \*